(12) United States Patent
Scheib et al.

(10) Patent No.: US 10,342,535 B2
(45) Date of Patent: Jul. 9, 2019

(54) METHOD OF APPLYING STAPLES TO LIVER AND OTHER ORGANS

(71) Applicant: Ethicon Endo-Surgery, LLC, Guaynabo, PR (US)

(72) Inventors: Charles J. Scheib, Loveland, OH (US); Frederick E. Shelton, IV, Hillsboro, OH (US); Nicholas Fanelli, Morrow, OH (US)

(73) Assignee: Ethicon LLC, Guaynabo, PR (US)

( * ) Notice: Subject to any disclaimer, the term of this patent is extended or adjusted under 35 U.S.C. 154(b) by 475 days.

(21) Appl. No.: 14/884,272

(22) Filed: Oct. 15, 2015

(65) Prior Publication Data

US 2017/0105725 A1 Apr. 20, 2017

(51) Int. Cl.
*A61B 17/072* (2006.01)
*A61B 17/3209* (2006.01)
*A61B 17/3201* (2006.01)

(52) U.S. Cl.
CPC .... *A61B 17/07207* (2013.01); *A61B 17/3201* (2013.01); *A61B 17/3209* (2013.01); *A61B 2017/07221* (2013.01); *A61B 2017/07271* (2013.01); *A61B 2017/07285* (2013.01)

(58) Field of Classification Search
None
See application file for complete search history.

(56) References Cited

U.S. PATENT DOCUMENTS

| 2,224,461 A | 12/1940 | Obstfeld |
| 4,319,576 A | 3/1982 | Rothfuss |
| 4,805,823 A | 2/1989 | Rothfuss |
| 4,925,082 A | 5/1990 | Kim |

(Continued)

FOREIGN PATENT DOCUMENTS

| CN | 202 313 537 U | 7/2012 |
| CN | 202 982 106 U | 6/2013 |

(Continued)

OTHER PUBLICATIONS

Randomized clinical trial of stapler versus clamp-crushing transection in elective liver resection. Rahbari, N.N. et al. British Journal of Surgery. 2014; 101: 200-207. Published online Jan. 8, 2014.*

(Continued)

*Primary Examiner* — Shaun David
(74) *Attorney, Agent, or Firm* — Frost Brown Todd LLC

(57) ABSTRACT

A method for treating a patient includes a surgical instrument having a handle assembly, a shaft assembly, and an end effector. The end effector includes an upper jaw and a lower jaw configured to pivot to receive a tissue of the patient therebetween. The upper and lower jaws respectively have upper and lower crush surfaces, which extends generally parallel with a centerline and are configured to receive the tissue thereagainst. The upper jaw also includes an anvil, whereas the lower jaw includes a staple cartridge and a deck facing the anvil. In addition, the lower jaw has a plurality of staple opening formed through the deck with a plurality of staples received therein. The upper and lower crush surfaces are configured to compress the tissue therebetween with a crush pressure configured to sever the tissue along the upper and lower crush surfaces.

19 Claims, 33 Drawing Sheets

(56) References Cited

U.S. PATENT DOCUMENTS

| | | | |
|---|---|---|---|
| 5,040,715 A * | 8/1991 | Green | A61B 17/07207 227/176.1 |
| 5,156,315 A | 10/1992 | Green et al. | |
| 5,282,807 A * | 2/1994 | Knoepfler | A61B 17/0682 227/180.1 |
| 5,307,976 A * | 5/1994 | Olson | A61B 17/07207 227/175.3 |
| 5,312,023 A * | 5/1994 | Green | A61B 17/07207 227/175.1 |
| 5,318,221 A * | 6/1994 | Green | A61B 17/07207 227/178.1 |
| 5,326,013 A * | 7/1994 | Green | A61B 17/07207 227/176.1 |
| 5,364,001 A | 11/1994 | Bryan | |
| 5,364,003 A | 11/1994 | Williamson, IV | |
| 5,389,098 A | 2/1995 | Tsuruta et al. | |
| 5,397,324 A * | 3/1995 | Carroll | A61B 17/07207 128/898 |
| 5,403,312 A | 4/1995 | Yates et al. | |
| 5,415,334 A | 5/1995 | Williamson et al. | |
| 5,417,361 A | 5/1995 | Williamson, IV | |
| 5,427,298 A | 6/1995 | Tegtmeier | |
| 5,452,837 A | 9/1995 | Williamson, IV et al. | |
| 5,465,895 A | 11/1995 | Knodel et al. | |
| 5,551,622 A * | 9/1996 | Yoon | A61B 17/072 227/176.1 |
| 5,597,107 A | 1/1997 | Knodel et al. | |
| 5,632,432 A | 5/1997 | Schulze et al. | |
| 5,673,840 A | 10/1997 | Schulze et al. | |
| 5,704,534 A | 1/1998 | Huitema et al. | |
| 5,709,335 A | 1/1998 | Heck | |
| 5,752,644 A | 5/1998 | Bolanos et al. | |
| 5,792,135 A | 8/1998 | Madhani et al. | |
| 5,814,055 A | 9/1998 | Knodel et al. | |
| 5,816,471 A | 10/1998 | Plyley et al. | |
| 5,817,084 A | 10/1998 | Jensen | |
| 5,878,193 A | 3/1999 | Wang et al. | |
| 6,003,517 A * | 12/1999 | Sheffield | A61B 18/1447 128/898 |
| 6,079,606 A * | 6/2000 | Milliman | A61B 17/07207 227/175.2 |
| 6,231,565 B1 | 5/2001 | Tovey et al. | |
| 6,264,089 B1 | 7/2001 | Hasegawa et al. | |
| 6,364,888 B1 | 4/2002 | Niemeyer et al. | |
| 6,443,970 B1 | 9/2002 | Schulze et al. | |
| 6,669,073 B2 * | 12/2003 | Milliman | A61B 17/07207 227/175.2 |
| 6,783,524 B2 | 8/2004 | Anderson et al. | |
| 6,978,921 B2 | 12/2005 | Shelton, IV et al. | |
| 7,000,818 B2 | 2/2006 | Shelton, IV et al. | |
| 7,143,923 B2 | 12/2006 | Shelton, IV et al. | |
| 7,235,089 B1 | 6/2007 | McGuckin, Jr. | |
| 7,237,708 B1 | 7/2007 | Guy et al. | |
| 7,303,108 B2 | 12/2007 | Shelton, IV | |
| 7,367,485 B2 | 5/2008 | Shelton, IV et al. | |
| 7,380,695 B2 | 6/2008 | Doll et al. | |
| 7,380,696 B2 | 6/2008 | Shelton, IV et al. | |
| 7,404,508 B2 | 7/2008 | Smith et al. | |
| 7,434,715 B2 | 10/2008 | Shelton, IV et al. | |
| 7,524,320 B2 | 4/2009 | Tierney | |
| 7,635,074 B2 | 12/2009 | Olson et al. | |
| 7,651,017 B2 | 1/2010 | Ortiz et al. | |
| 7,691,098 B2 | 4/2010 | Wallace | |
| 7,721,930 B2 | 5/2010 | McKenna et al. | |
| 7,806,891 B2 | 10/2010 | Nowlin et al. | |
| 7,954,687 B2 | 6/2011 | Zemlok et al. | |
| 7,980,443 B2 | 7/2011 | Scheib et al. | |
| 8,011,555 B2 | 9/2011 | Tarinelli et al. | |
| 8,210,411 B2 | 7/2012 | Yates et al. | |
| 8,342,377 B2 * | 1/2013 | Milliman | A61B 17/07207 227/175.2 |
| 8,360,298 B2 | 1/2013 | Farascioni et al. | |
| 8,393,516 B2 | 3/2013 | Kostrzewski | |
| 8,408,439 B2 | 4/2013 | Huang et al. | |
| 8,418,908 B1 | 4/2013 | Beardsley | |
| 8,453,914 B2 | 6/2013 | Laurent et al. | |
| 8,479,969 B2 | 7/2013 | Shelton, IV | |
| 8,485,412 B2 | 7/2013 | Shelton, IV et al. | |
| 8,573,461 B2 | 11/2013 | Shelton, IV et al. | |
| 8,573,465 B2 | 11/2013 | Shelton, IV | |
| 8,602,288 B2 | 12/2013 | Shelton, IV et al. | |
| 8,616,431 B2 | 12/2013 | Timm et al. | |
| 8,783,541 B2 | 7/2014 | Shelton, IV et al. | |
| 8,800,838 B2 | 8/2014 | Shelton, IV | |
| 8,820,605 B2 | 9/2014 | Shelton, IV | |
| 8,833,632 B2 | 9/2014 | Swensgard | |
| 8,844,789 B2 | 9/2014 | Shelton, IV et al. | |
| 8,940,000 B2 | 1/2015 | Kasvikis et al. | |
| 9,050,084 B2 | 6/2015 | Schmid et al. | |
| 9,186,142 B2 | 11/2015 | Fanelli et al. | |
| 9,237,890 B2 | 1/2016 | Kostrzewski | |
| 9,272,406 B2 | 3/2016 | Aronhalt et al. | |
| 9,301,759 B2 | 4/2016 | Spivey et al. | |
| 9,386,984 B2 | 7/2016 | Aronhalt et al. | |
| 9,492,146 B2 | 11/2016 | Kostrzewski et al. | |
| 9,498,215 B2 | 11/2016 | Duque et al. | |
| 9,517,065 B2 | 12/2016 | Simms et al. | |
| 9,572,577 B2 | 2/2017 | Lloyd et al. | |
| 9,615,826 B2 | 4/2017 | Shelton, IV et al. | |
| 9,724,091 B2 | 8/2017 | Shelton, IV et al. | |
| 9,750,502 B2 | 9/2017 | Scirica et al. | |
| 9,775,613 B2 | 10/2017 | Shelton, IV et al. | |
| 9,801,627 B2 | 10/2017 | Harris et al. | |
| 9,827,002 B2 | 11/2017 | Hausen et al. | |
| 2002/0156511 A1 * | 10/2002 | Habib | A61B 18/14 607/113 |
| 2007/0075115 A1 * | 4/2007 | Olson | A61B 17/07207 227/175.1 |
| 2007/0175949 A1 * | 8/2007 | Shelton, IV | A61B 17/07207 227/176.1 |
| 2008/0169327 A1 * | 7/2008 | Shelton | A61B 17/105 227/176.1 |
| 2008/0169328 A1 | 7/2008 | Shelton, IV | |
| 2008/0169332 A1 | 7/2008 | Shelton, IV et al. | |
| 2008/0237297 A1 * | 10/2008 | Demmy | A61B 17/07207 227/176.1 |
| 2009/0048589 A1 | 2/2009 | Takashino et al. | |
| 2009/0101692 A1 * | 4/2009 | Whitman | A61B 17/07207 227/175.1 |
| 2009/0206131 A1 | 8/2009 | Weisenburgh, II et al. | |
| 2009/0206144 A1 * | 8/2009 | Doll | A61B 17/07207 227/177.1 |
| 2010/0069942 A1 | 3/2010 | Shelton, IV | |
| 2010/0072258 A1 * | 3/2010 | Farascioni | A61B 17/07207 227/180.1 |
| 2010/0270355 A1 * | 10/2010 | Whitman | A61B 17/068 227/176.1 |
| 2011/0036891 A1 * | 2/2011 | Zemlok | A61B 17/07207 227/176.1 |
| 2013/0092719 A1 * | 4/2013 | Kostrzewski | A61B 17/07207 227/177.1 |
| 2013/0186931 A1 * | 7/2013 | Beardsley | A61B 17/0644 227/176.1 |
| 2013/0334284 A1 | 12/2013 | Swayze | |
| 2014/0081176 A1 | 3/2014 | Hassan | |
| 2014/0239036 A1 | 8/2014 | Zerkle et al. | |
| 2014/0239037 A1 | 8/2014 | Boudreaux et al. | |
| 2014/0239038 A1 | 8/2014 | Leimbach et al. | |
| 2014/0239040 A1 | 8/2014 | Fanelli et al. | |
| 2014/0239041 A1 | 8/2014 | Zerkle et al. | |
| 2014/0239043 A1 | 8/2014 | Simms et al. | |
| 2014/0239044 A1 | 8/2014 | Hoffman | |
| 2014/0299648 A1 | 10/2014 | Shelton, IV et al. | |
| 2015/0108198 A1 | 4/2015 | Estrella | |
| 2015/0150620 A1 | 6/2015 | Miyamoto et al. | |
| 2015/0272575 A1 | 10/2015 | Leimbach et al. | |
| 2015/0374360 A1 | 12/2015 | Scheib et al. | |
| 2015/0374373 A1 | 12/2015 | Rector et al. | |
| 2016/0302792 A1 * | 10/2016 | Motai | A61B 17/00234 |
| 2017/0105727 A1 | 4/2017 | Scheib et al. | |
| 2017/0105728 A1 | 4/2017 | Scheib et al. | |
| 2017/0105729 A1 | 4/2017 | Scheib et al. | |

(56) References Cited

U.S. PATENT DOCUMENTS

| | | | |
|---|---|---|---|
| 2017/0105730 A1 | 4/2017 | Scheib et al. | |
| 2017/0105731 A1 | 4/2017 | Scheib et al. | |
| 2017/0105732 A1 | 4/2017 | Scheib et al. | |
| 2017/0105733 A1 | 4/2017 | Scheib et al. | |

FOREIGN PATENT DOCUMENTS

| | | |
|---|---|---|
| CN | 204 158 440 U | 2/2015 |
| CN | 204 158 441 U | 2/2015 |
| EP | 0 623 311 A2 | 11/1994 |
| EP | 0 878 169 A1 | 11/1998 |
| EP | 1 790 293 A2 | 5/2007 |
| EP | 2 090 255 A1 | 8/2009 |
| EP | 2 098 170 A2 | 9/2009 |
| EP | 2 283 779 A1 | 2/2011 |
| EP | 2 386 253 A2 | 11/2011 |
| EP | 2 583 630 A2 | 4/2013 |
| EP | 2 586 379 A1 | 5/2013 |
| EP | 2 886 070 A1 | 6/2015 |
| WO | WO 94/24943 A1 | 11/1994 |
| WO | WO 96/18344 A2 | 6/1996 |
| WO | WO 2009/022614 A1 | 2/2009 |
| WO | WO 2012/141679 A1 | 10/2012 |
| WO | WO 2013/109445 A2 | 7/2013 |
| WO | WO 2015/137181 A1 | 9/2015 |
| WO | WO 2015/153324 A1 | 10/2015 |

OTHER PUBLICATIONS

Liver transection using vascular stapler: a review. Schemmer, Peter et al. HPB, 2008; 10: 249-252.*
Laparoscopic liver resection: when to use the laparoscopic stapler device. Gumbs, Andrew et al. HPB, 2008; 10: 296-303.*
US FDA 510K Application #K061095 for Endo GIA Stapler, indicated use for transection/resection of liver substance, hepatic vasculature, and biliary structures. Stamped May 31, 2006.*
U.S. Appl. No. 14/810,786, filed Jul. 28, 2015.
U.S. Appl. No. 14/884,073.
U.S. Appl. No. 14/884,096.
U.S. Appl. No. 14/884,117.
U.S. Appl. No. 14/884,176.
U.S. Appl. No. 14/884,198.
U.S. Appl. No. 14/884,228.
U.S. Appl. No. 14/884,248.
European Search Report and Written Opinion dated Mar. 17, 2017 for Application No. EP 16193980.6, 6 pgs.
European Search Report and Written Opinion dated Jan. 13, 2017 for Application No. EP 16193975.6, 9 pgs.
European Search Report and Written Opinion dated Jan. 16, 2017 for Application No. EP 16193965.7, 8 pgs.
European Search Report and Written Opinion dated Jan. 13, 2017 for Application No. EP 16193976.4, 9 pgs.
European Search Report and Written Opinion dated Mar. 14, 2017 for Application No. EP 16193957.4, 6 pgs.
European Search Report and Written Opinion dated Feb. 8, 2017 for Application No. EP 16193964.0, 7 pgs.
European Search Report, Partial, and Written Opinion dated Feb. 22, 2017 for Application No. EP 16193954.1, 9 pgs.
European Search Report and Written Opinion dated Aug. 11, 2017 for Application No. EP 16193954.1, 24 pgs.
Declaration of Non-Establishment of International Search Report and Written Opinion dated Mar. 10, 2017 for Application No. PCT/US2016/055880, 6 pgs.
International Search Report and Written Opinion dated Jan. 3, 2017 for Application No. PCT/US2016/055872, 9 pgs.
International Search Report and Written Opinion dated Jan. 4, 2017 for Application No. PCT/US2016/056757, 13 pgs.
International Search Report and Written Opinion dated Jan. 16, 2017 for Application No. PCT/US2016/055874, 10 pgs.
International Search Report and Written Opinion dated Jan. 16, 2017 for Application No. PCT/US2016/055877, 13 pgs.
International Search Report and Written Opinion dated Jan. 2, 2017 for Application No. PCT/US2016/055878, 9 pgs.
International Search Report and Written Opinion dated Mar. 8, 2017 for Application No. PCT/US2016/056756, 10 pgs.
International Search Report and Written Opinion dated Apr. 9, 2018 for Application No. PCT/US2016/056754, 28 pgs.

* cited by examiner

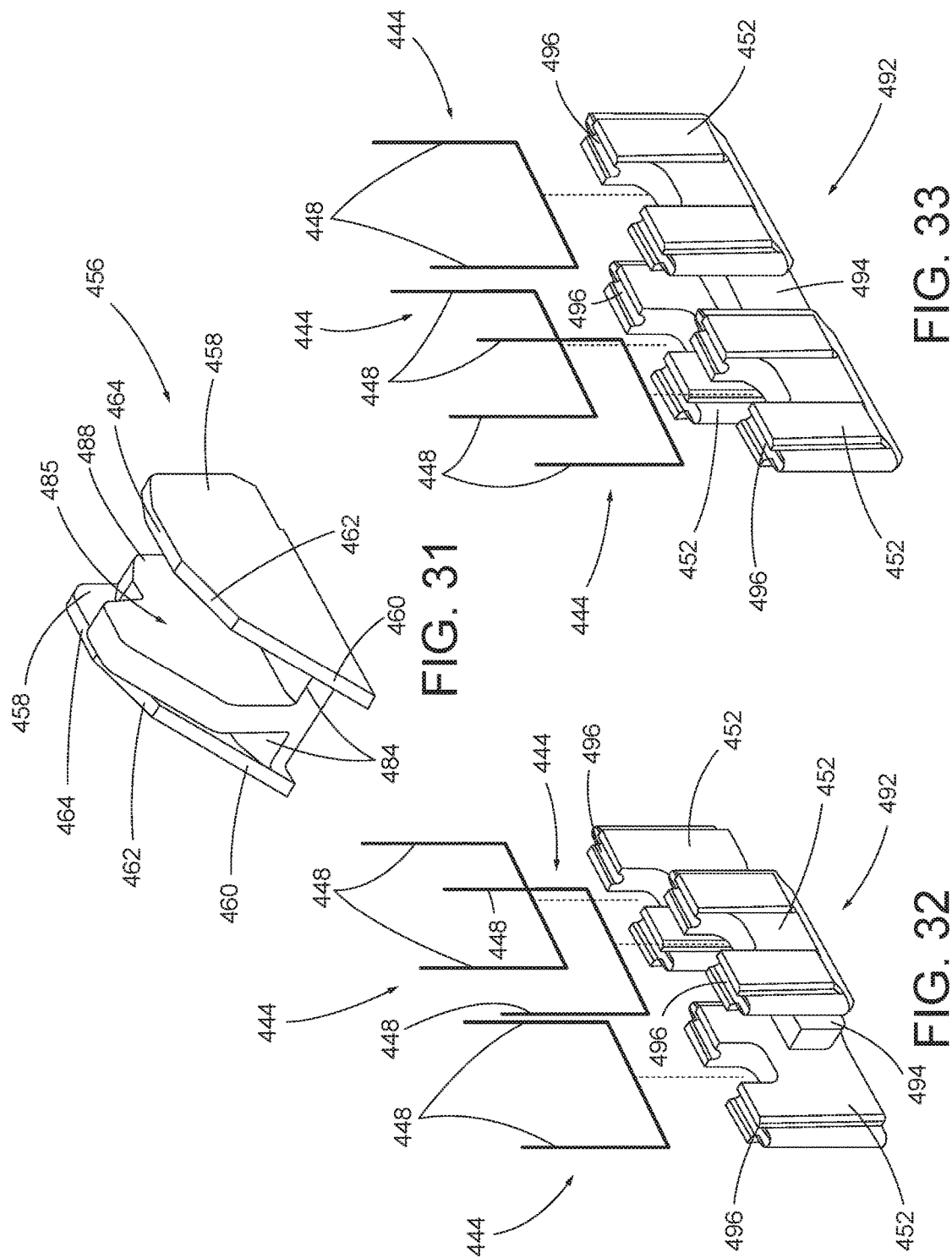

METHOD OF APPLYING STAPLES TO LIVER AND OTHER ORGANS

BACKGROUND

In some settings, endoscopic surgical instruments may be preferred over traditional open surgical devices since a smaller incision may reduce the post-operative recovery time and complications. Consequently, some endoscopic surgical instruments may be suitable for placement of a distal end effector at a desired surgical site through the cannula of a trocar. These distal end effectors may engage tissue in a number of ways to achieve a diagnostic or therapeutic effect (e.g., endocutter, grasper, cutter, stapler, clip applier, access device, drug/gene therapy delivery device, and energy delivery device using ultrasonic vibration, RF, laser, etc.). Endoscopic surgical instruments may include a shaft between the end effector and a handle portion, which is manipulated by the clinician. Such a shaft may enable insertion to a desired depth and rotation about the longitudinal axis of the shaft, thereby facilitating positioning of the end effector within the patient. Positioning of an end effector may be further facilitated through inclusion of one or more articulation joints or features, enabling the end effector to be selectively articulated or otherwise deflected relative to the longitudinal axis of the shaft.

Examples of endoscopic surgical instruments include surgical staplers. Some such staplers are operable to clamp down on layers of tissue, cut through the clamped layers of tissue, and drive staples through the layers of tissue to substantially seal the severed layers of tissue together near the severed ends of the tissue layers. Merely exemplary surgical staplers are disclosed in U.S. Pat. No. 4,805,823, entitled "Pocket Configuration for Internal Organ Staplers," issued Feb. 21, 1989; U.S. Pat. No. 5,415,334, entitled "Surgical Stapler and Staple Cartridge," issued May 16, 1995; U.S. Pat. No. 5,465,895, entitled "Surgical Stapler Instrument," issued Nov. 14, 1995; U.S. Pat. No. 5,597,107, entitled "Surgical Stapler Instrument," issued Jan. 28, 1997; U.S. Pat. No. 5,632,432, entitled "Surgical Instrument," issued May 27, 1997; U.S. Pat. No. 5,673,840, entitled "Surgical Instrument," issued Oct. 7, 1997; U.S. Pat. No. 5,704,534, entitled "Articulation Assembly for Surgical Instruments," issued Jan. 6, 1998; U.S. Pat. No. 5,814,055, entitled "Surgical Clamping Mechanism," issued Sep. 29, 1998; U.S. Pat. No. 6,978,921, entitled "Surgical Stapling Instrument Incorporating an E-Beam Firing Mechanism," issued Dec. 27, 2005; U.S. Pat. No. 7,000,818, entitled "Surgical Stapling Instrument Having Separate Distinct Closing and Firing Systems," issued Feb. 21, 2006; U.S. Pat. No. 7,143,923, entitled "Surgical Stapling Instrument Having a Firing Lockout for an Unclosed Anvil," issued Dec. 5, 2006; U.S. Pat. No. 7,303,108, entitled "Surgical Stapling Instrument Incorporating a Multi-Stroke Firing Mechanism with a Flexible Rack," issued Dec. 4, 2007; U.S. Pat. No. 7,367,485, entitled "Surgical Stapling Instrument Incorporating a Multistroke Firing Mechanism Having a Rotary Transmission," issued May 6, 2008; U.S. Pat. No. 7,380,695, entitled "Surgical Stapling Instrument Having a Single Lockout Mechanism for Prevention of Firing," issued Jun. 3, 2008; U.S. Pat. No. 7,380,696, entitled "Articulating Surgical Stapling Instrument Incorporating a Two-Piece E-Beam Firing Mechanism," issued Jun. 3, 2008; U.S. Pat. No. 7,404,508, entitled "Surgical Stapling and Cutting Device," issued Jul. 29, 2008; U.S. Pat. No. 7,434,715, entitled "Surgical Stapling Instrument Having Multistroke Firing with Opening Lockout," issued Oct. 14, 2008; U.S. Pat. No. 7,721,930, entitled "Disposable Cartridge with Adhesive for Use with a Stapling Device," issued May 25, 2010; U.S. Pat. No. 8,408,439, entitled "Surgical Stapling Instrument with An Articulatable End Effector," issued Apr. 2, 2013; and U.S. Pat. No. 8,453,914, entitled "Motor-Driven Surgical Cutting Instrument with Electric Actuator Directional Control Assembly," issued Jun. 4, 2013. The disclosure of each of the above-cited U.S. Patents is incorporated by reference herein.

While the surgical staplers referred to above are described as being used in endoscopic procedures, it should be understood that such surgical staplers may also be used in open procedures and/or other non-endoscopic procedures. By way of example only, a surgical stapler may be inserted through a thoracotomy, and thereby between a patient's ribs, to reach one or more organs in a thoracic surgical procedure that does not use a trocar as a conduit for the stapler. Such procedures may include the use of the stapler to sever and close a vessel leading to a lung. For instance, the vessels leading to an organ may be severed and closed by a stapler before removal of the organ from the thoracic cavity. Of course, surgical staplers may be used in various other settings and procedures.

Examples of surgical staplers that may be particularly suited or use through a thoracotomy are disclosed in U.S. patent application Ser. No. 14/810,786, entitled "Surgical Staple Cartridge with Compression Feature at Knife Slot," filed Jul. 29, 2015, published as U.S. Pub No. 2017/0027567 on Feb. 2, 2017; U.S. Patent Pub. No. 2014/0243801, entitled "Surgical Instrument End Effector Articulation Drive with Pinion and Opposing Racks," published Aug. 28, 2014, issued as U.S. Pat. No. 9,186,142 on Nov. 17, 2015; U.S. Patent Pub. No. 2014/0239041, entitled "Lockout Feature for Movable Cutting Member of Surgical Instrument," published Aug. 28, 2014, issued as U.S. Pat. No. 9,717,497 on Aug. 1, 2017; U.S. Patent Pub. No. 2014/0239042, entitled "Integrated Tissue Positioning and Jaw Alignment Features for Surgical Stapler," published Aug. 28, 2014, issued as U.S. Pat. No. 9,517,065 on Dec. 13, 2016; U.S. Patent Pub. No. 2014/0239036, entitled "Jaw Closure Feature for End Effector of Surgical Instrument," published Aug. 28, 2014, issued as U.S. Pat. No. 9,839,421 on Dec. 12, 2017; U.S. Patent Pub. No. 2014/0239040, entitled "Surgical Instrument with Articulation Lock having a Detenting Binary Spring," published Aug. 28, 2014, issued as U.S. Pat. No. 9,867,615 on Jan. 16, 2018; U.S. Patent Pub. No. 2014/0239043, entitled "Distal Tip Features for End Effector of Surgical Instrument," published Aug. 28, 2014, issued as U.S. Pat. No. 9,622,746 on Apr. 18, 2017; U.S. Patent Pub. No. 2014/0239037, entitled "Staple Forming Features for Surgical Stapling Instrument," published Aug. 28, 2014, issued as U.S. Pat. No. 10,092,292 on Oct. 9, 2018; U.S. Patent Pub. No. 2014/0239038, entitled "Surgical Instrument with Multi-Diameter Shaft," published August 28, 2014, issued as U.S. Pat. No. 9,795,379 on Oct. 24, 2017; and U.S. Patent Pub. No. 2014/0239044, entitled "Installation Features for Surgical Instrument End Effector Cartridge," published Aug. 28, 2014, issued as U.S. Pat. No. 9,808,248 on Nov. 7, 2017. The disclosure of each of the above-cited U.S. Patent Applications is incorporated by reference herein.

While various kinds of surgical stapling instruments and associated components have been made and used, it is believed that no one prior to the inventor(s) has made or used the invention described in the appended claims.

BRIEF DESCRIPTION OF THE DRAWINGS

The accompanying drawings, which are incorporated in and constitute a part of this specification, illustrate embodiments of the invention, and, together with the general description of the invention given above, and the detailed description of the embodiments given below, serve to explain the principles of the present invention.

FIG. 31 depicts a perspective view of a wedge sled of the lower jaw shown in FIG. 30;

FIG. 32 depicts a right perspective view of a triple driver assembly of the lower jaw of FIG. 27;

FIG. 33 depicts a right perspective view of another triple driver assembly of the lower jaw of FIG. 27;

Figure 1:
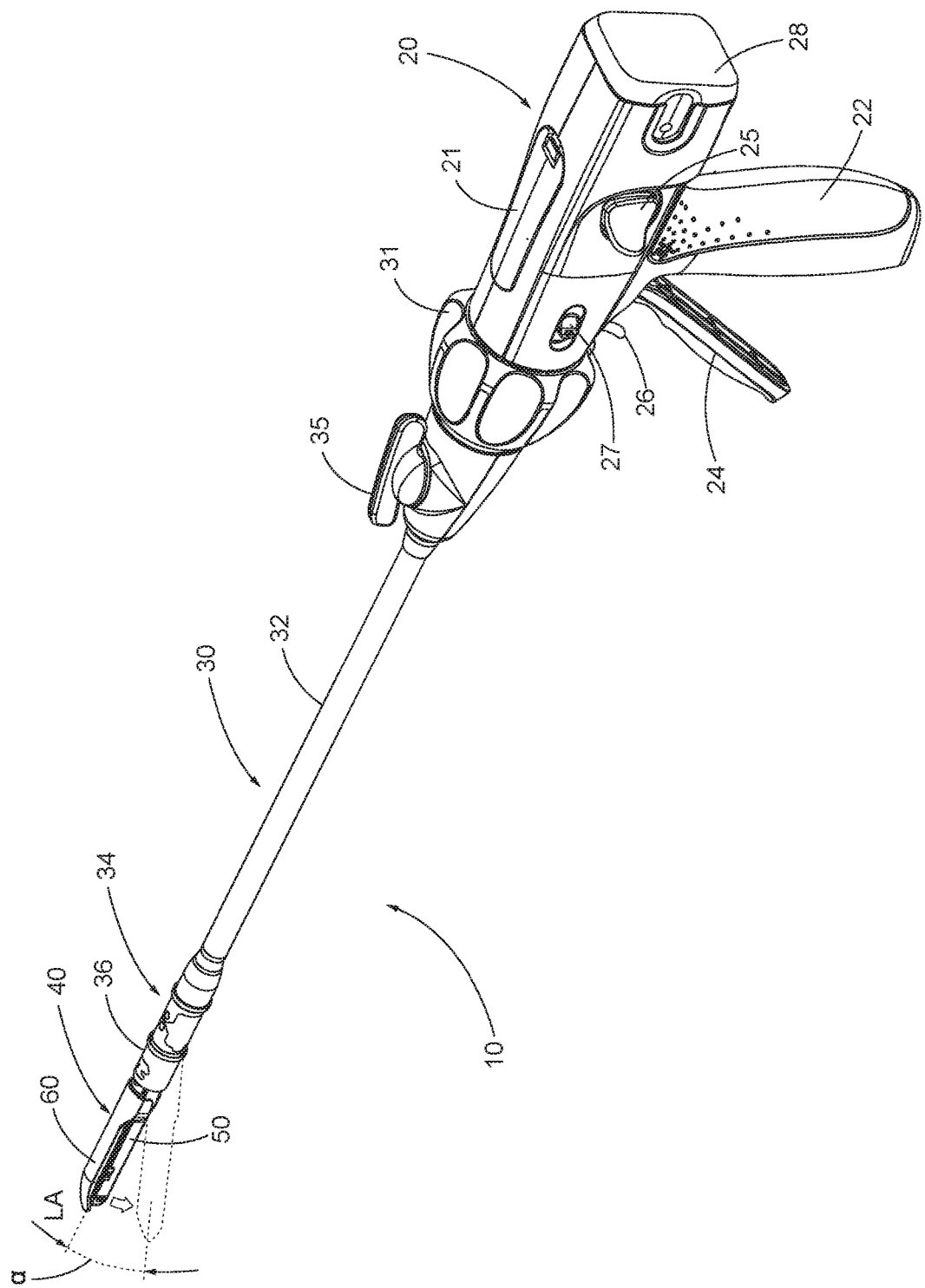
FIG. 1 depicts a perspective view of an exemplary articulating surgical stapling instrument.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. Accordingly, the drawings and descriptions should be regarded as illustrative in nature and not restrictive.

I. Exemplary Surgical Stapler

FIG. 1 depicts an exemplary surgical stapling and severing instrument (10) that includes a handle assembly (20), a shaft assembly (30), and an end effector (40). End effector (40) and the distal portion of shaft assembly (30) are sized for insertion, in a nonarticulated state as depicted in FIG. 1, through a trocar cannula to a surgical site in a patient for performing a surgical procedure. By way of example only, such a trocar may be inserted in a patient's abdomen, between two of the patient's ribs, or elsewhere. In some settings, instrument (10) is used without a trocar. For instance, end effector (40) and the distal portion of shaft assembly (30) may be inserted directly through a thoracotomy or other type of incision. It should be understood that terms such as "proximal" and "distal" are used herein with reference to a clinician gripping handle assembly (20) of instrument (10). Thus, end effector (40) is distal with respect to the more proximal handle assembly (20). It will be further appreciated that for convenience and clarity, spatial terms such as "vertical" and "horizontal" are used herein with respect to the drawings. However, surgical instruments are used in many orientations and positions, and these terms are not intended to be limiting and absolute.

A. Exemplary Handle Assembly and Shaft Assembly

Figure 2:
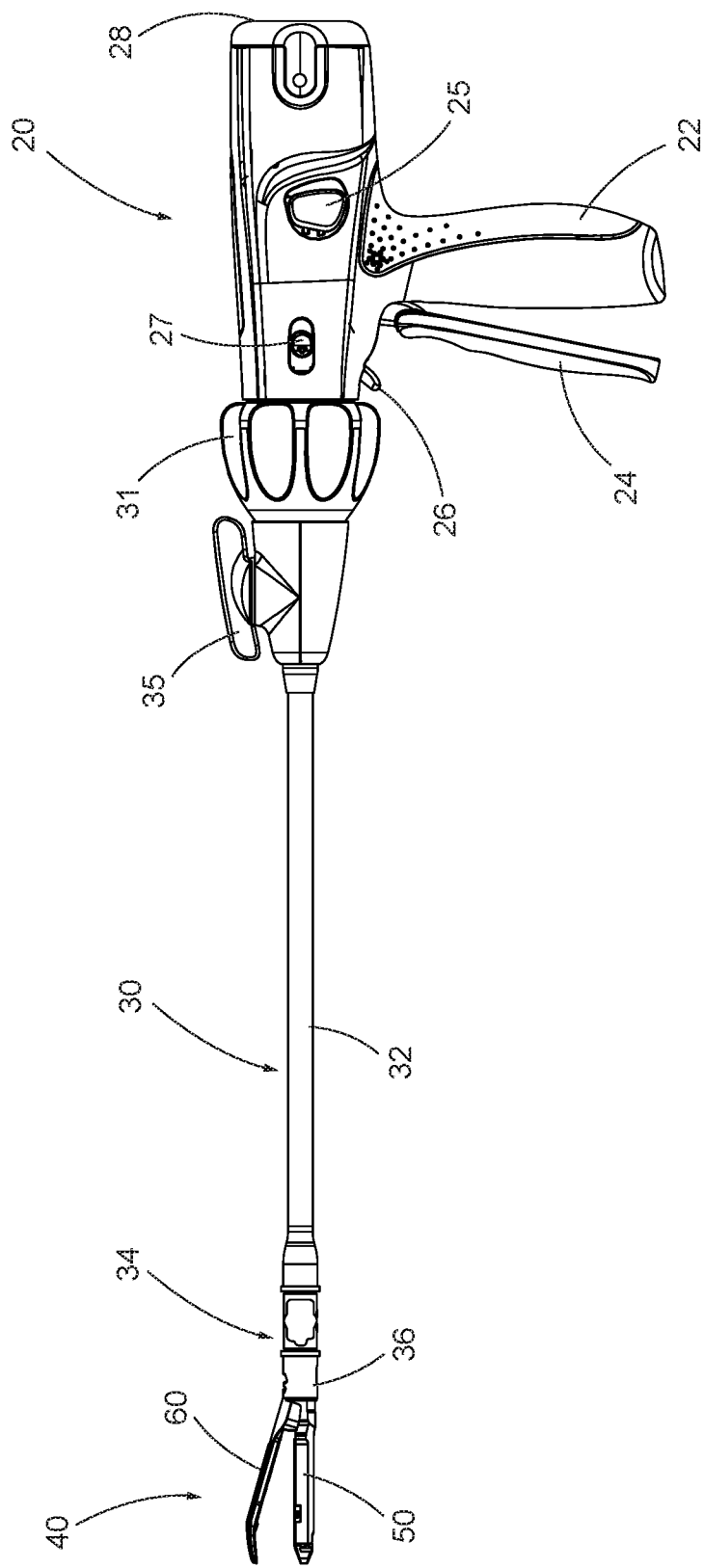
FIG. 2 depicts a side elevational view of the instrument of FIG. 1.

As shown in FIGS. 1-2, handle assembly (20) of the present example comprises pistol grip (22), a closure trigger (24), and a firing trigger (26). Each trigger (24, 26) is selectively pivotable toward and away from pistol grip (22) as will be described in greater detail below. Handle assembly (20) further includes an anvil release button (25), a firing beam reverse switch (27), and a removable battery pack (28). These components will also be described in greater detail below. Of course, handle assembly (20) may have a variety of other components, features, and operabilities, in addition to or in lieu of any of those noted above. Other suitable configurations for handle assembly (20) will be apparent to those of ordinary skill in the art in view of the teachings herein.

Figure 3:
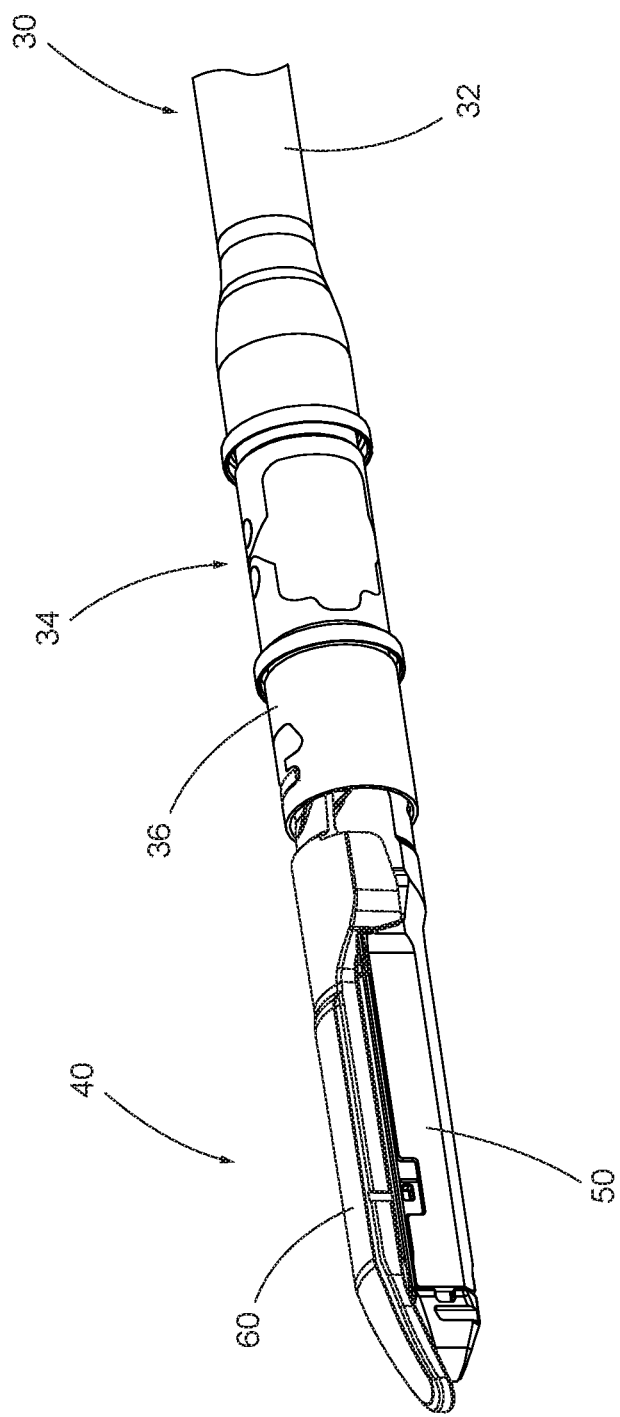
FIG. 3 depicts a perspective view of an end effector of the instrument of FIG. 1, with the end effector in a closed configuration.

As shown in FIGS. 1-3, shaft assembly (30) of the present example comprises an outer closure tube (32), an articulation section (34), and a closure ring (36), which is further coupled with end effector (40). Closure tube (32) extends along the length of shaft assembly (30). Closure ring (36) is positioned distal to articulation section (34). Closure tube (32) and closure ring (36) are configured to translate longitudinally relative to handle assembly (20). Longitudinal translation of closure tube (32) is communicated to closure ring (36) via articulation section (34). Exemplary features that may be used to provide longitudinal translation of closure tube (32) and closure ring (36) will be described in greater detail below.

Articulation section (34) is operable to laterally deflect closure ring (36) and end effector (40) laterally away from the longitudinal axis (LA) of shaft assembly (30) at a desired angle ($\alpha$). End effector (40) may thereby reach behind an organ or approach tissue from a desired angle or for other reasons. In some versions, articulation section (34) enables deflection of end effector (40) along a single plane. In some other versions, articulation section (34) enables deflection of end effector along more than one plane. In the present example, articulation is controlled through an articulation control knob (35) which is located at the proximal end of shaft assembly (30). Knob (35) is rotatable about an axis that is perpendicular to the longitudinal axis (LA) of shaft assembly (30). Closure ring (36) and end effector (40) pivot about an axis that is perpendicular to the longitudinal axis (LA) of shaft assembly (30) in response to rotation of knob (35). By way of example only, rotation of knob (35) clockwise may cause corresponding clockwise pivoting of closure ring (36) and end effector (40) at articulation section (34). Articulation section (34) is configured to communicate longitudinal translation of closure tube (32) to closure ring (36), regardless of whether articulation section (34) is in a straight configuration or an articulated configuration.

In some versions, articulation section (34) and/or articulation control knob (35) are/is constructed and operable in accordance with at least some of the teachings of U.S. Pub. No. 2014/0243801, entitled "Surgical Instrument End Effector Articulation Drive with Pinion and Opposing Racks," published Aug. 28, 2014, issued as U.S. Pat. No. 9,186,142 on Nov. 17, 2015, the disclosure of which is incorporated by reference herein. Articulation section (34) may also be constructed and operable in accordance with at least some of the teachings of U.S. patent application Ser. No. 14/314,125, entitled "Articulation Drive Features for Surgical Stapler," filed Jun. 25, 2014, published as U.S. Pub. No. 2015/0374360 on Dec. 31, 2015, the disclosure of which is incorporated by reference herein; and/or in accordance with the various teachings below. Other suitable forms that articulation section (34) and articulation knob (35) may take will be apparent to those of ordinary skill in the art in view of the teachings herein.

As shown in FIGS. 1-2, shaft assembly (30) of the present example further includes a rotation knob (31). Rotation knob (31) is operable to rotate the entire shaft assembly (30) and end effector (40) relative to handle assembly (20) about the longitudinal axis (LA) of shaft assembly (30). In some versions, rotation knob (31) is operable to selectively lock the angular position of shaft assembly (30) and end effector

(40) relative to handle assembly (20) about the longitudinal axis (LA) of shaft assembly (30). For instance, rotation knob (31) may be translatable between a first longitudinal position, in which shaft assembly (30) and end effector (40) are rotatable relative to handle assembly (20) about the longitudinal axis (LA) of shaft assembly (30); and a second longitudinal position, in which shaft assembly (30) and end effector (40) are not rotatable relative to handle assembly (20) about the longitudinal axis (LA) of shaft assembly (30). Of course, shaft assembly (30) may have a variety of other components, features, and operabilities, in addition to or in lieu of any of those noted above. By way of example only, at least part of shaft assembly (30) is constructed in accordance with at least some of the teachings of U.S. Pub. No. 2014/0239038, entitled "Surgical Instrument with Multi-Diameter Shaft," published Aug. 28, 2014, issued as U.S. Pat. No. 9,795,379 on Oct. 24, 2017, the disclosure of which is incorporated by reference herein. Other suitable configurations for shaft assembly (30) will be apparent to those of ordinary skill in the art in view of the teachings herein.

B. Exemplary End Effector

Figure 4:
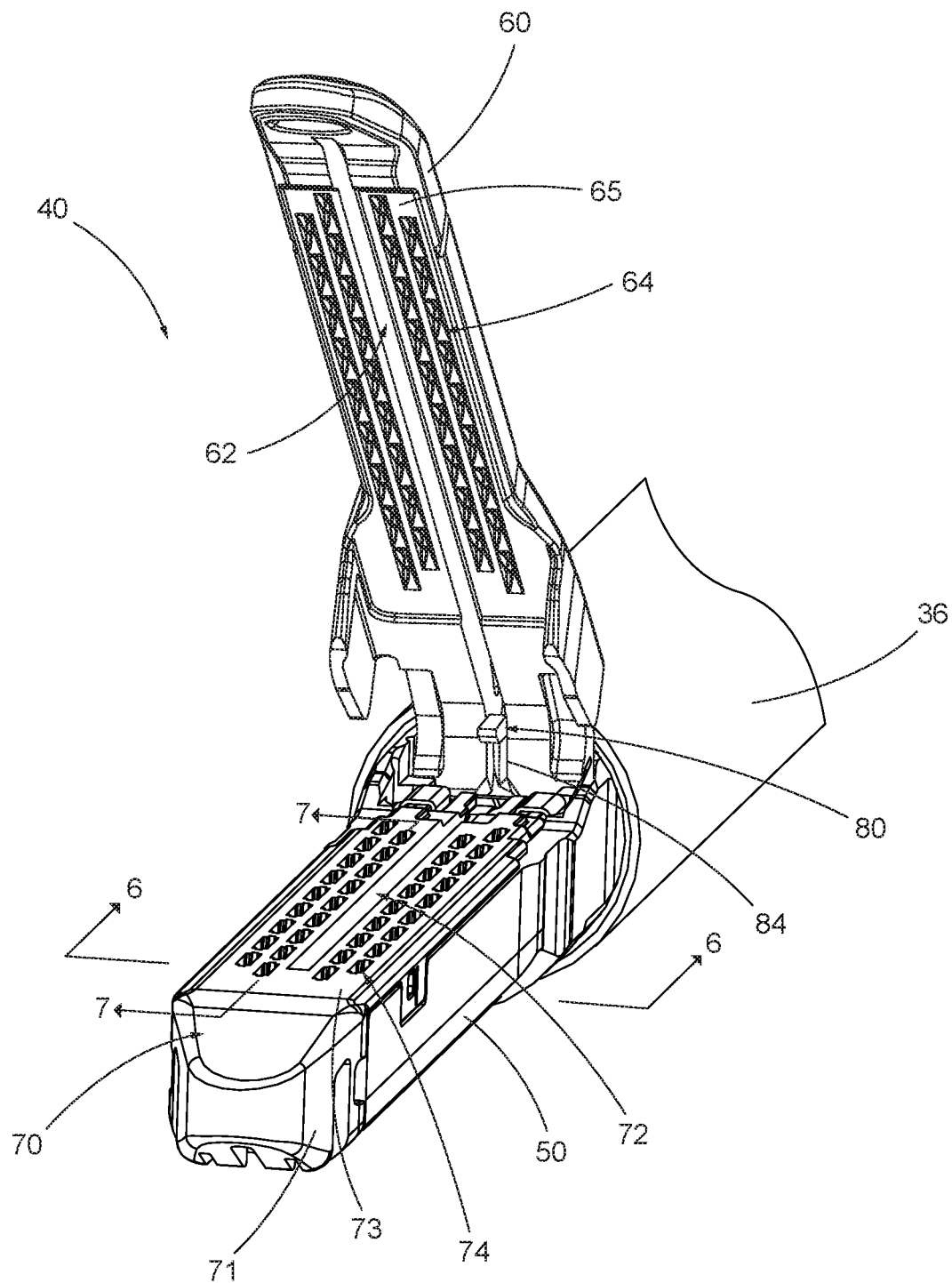
FIG. 4 depicts a perspective view of the end effector of FIG. 3, with the end effector in an open configuration.
Figure 5:
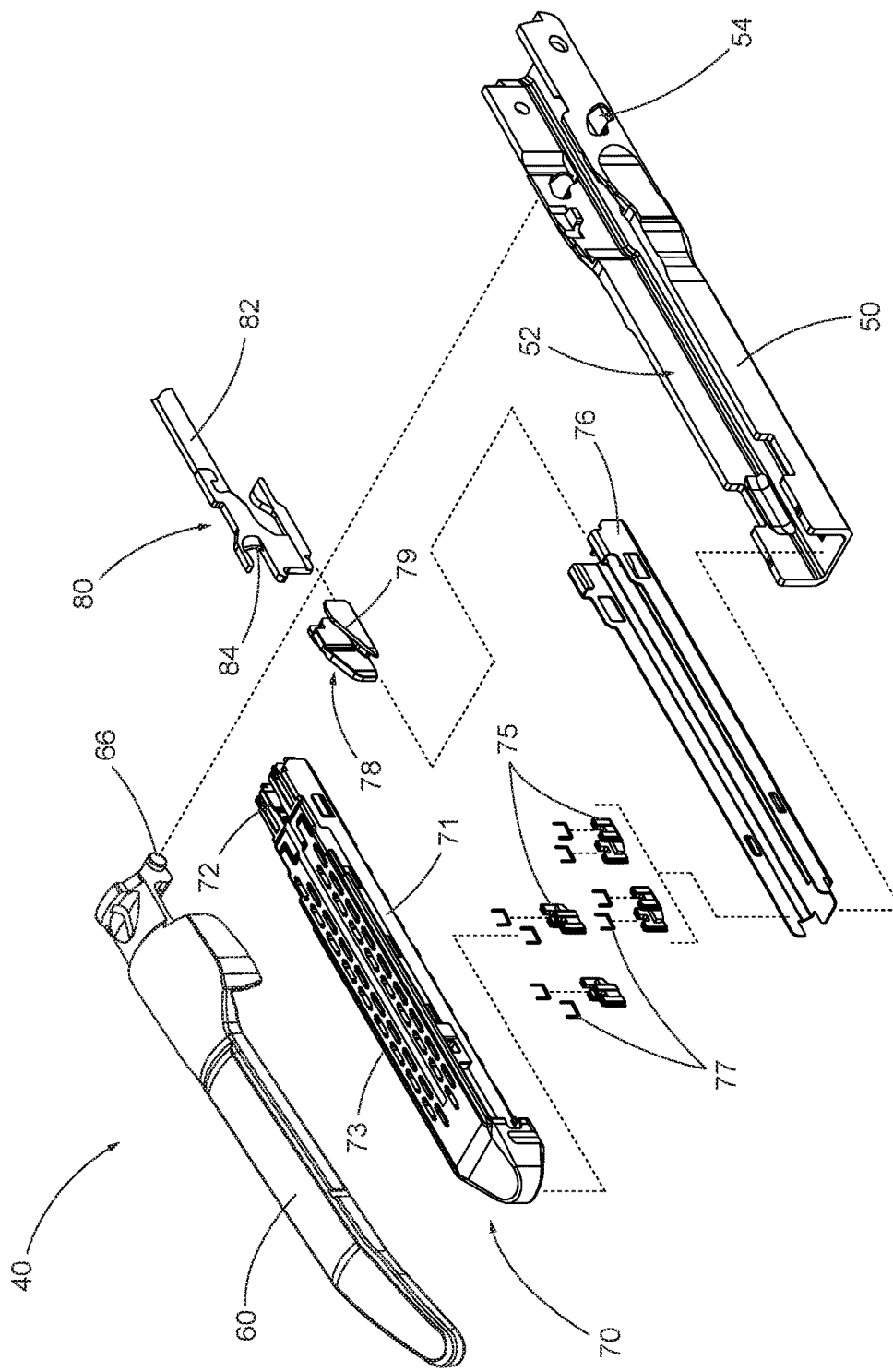
FIG. 5 depicts an exploded perspective view of the end effector of FIG. 3.

As also shown in FIGS. 3-5, end effector (40) of the present example includes a lower jaw (50) and a pivotable anvil (60). Anvil (60) includes a pair of integral, outwardly extending pins (66) that are disposed in corresponding curved slots (54) of lower jaw (50). Anvil (60) is pivotable toward and away from lower jaw (50) between an open position (shown in FIGS. 2 and 4) and a closed position (shown in FIGS. 1, 3, and 7A-7B). Use of the term "pivotable" (and similar terms with "pivot" as a base) should not be read as necessarily requiring pivotal movement about a fixed axis. For instance, in the present example, anvil (60) pivots about an axis that is defined by pins (66), which slide along curved slots (54) of lower jaw (50) as anvil (60) moves toward lower jaw (50). In such versions, the pivot axis translates along the path defined by slots (54) while anvil (60) simultaneously pivots about that axis. In addition or in the alternative, the pivot axis may slide along slots (54) first, with anvil (60) then pivoting about the pivot axis after the pivot axis has slid a certain distance along the slots (54). It should be understood that such sliding/translating pivotal movement is encompassed within terms such as "pivot," "pivots," "pivotal," "pivotable," "pivoting," and the like. Of course, some versions may provide pivotal movement of anvil (60) about an axis that remains fixed and does not translate within a slot or channel, etc.

As best seen in FIG. 5, lower jaw (50) of the present example defines a channel (52) that is configured to receive a staple cartridge (70). Staple cartridge (70) may be inserted into channel (52), end effector (40) may be actuated, and then staple cartridge (70) may be removed and replaced with another staple cartridge (70). Lower jaw (50) thus releasably retains staple cartridge (70) in alignment with anvil (60) for actuation of end effector (40). In some versions, lower jaw (50) is constructed in accordance with at least some of the teachings of U.S. Pub. No. 2014/0239044, entitled "Installation Features for Surgical Instrument End Effector Cartridge," published Aug. 28, 2014, issued as U.S. Pat. No. 9,808,248 on Nov. 7, 2017, the disclosure of which is incorporated by reference herein. Other suitable forms that lower jaw (50) may take will be apparent to those of ordinary skill in the art in view of the teachings herein.

Figure 6:
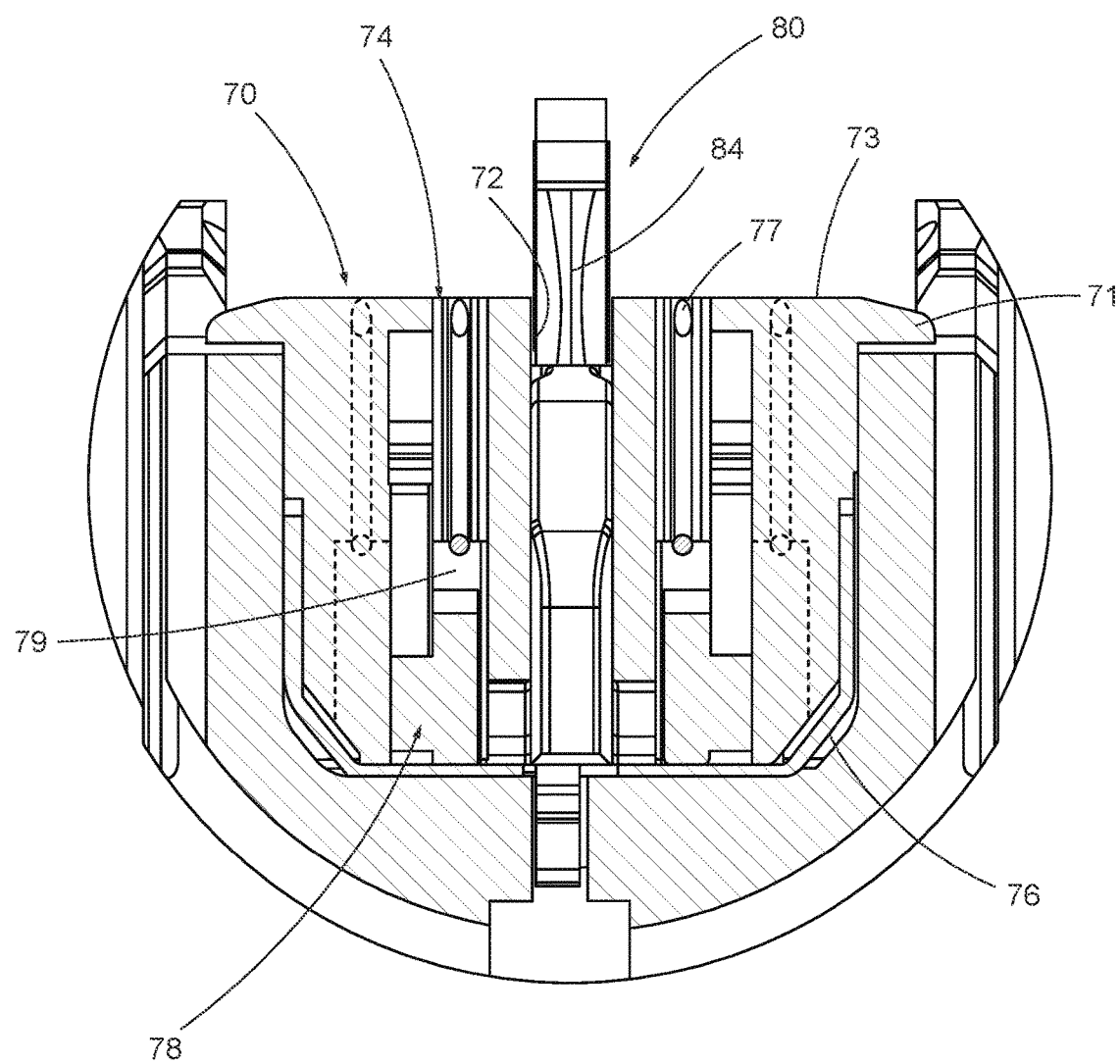
FIG. 6 depicts a cross-sectional end view of the end effector of FIG. 3, taken along line 6-6 of FIG. 4.
Figure 7A:
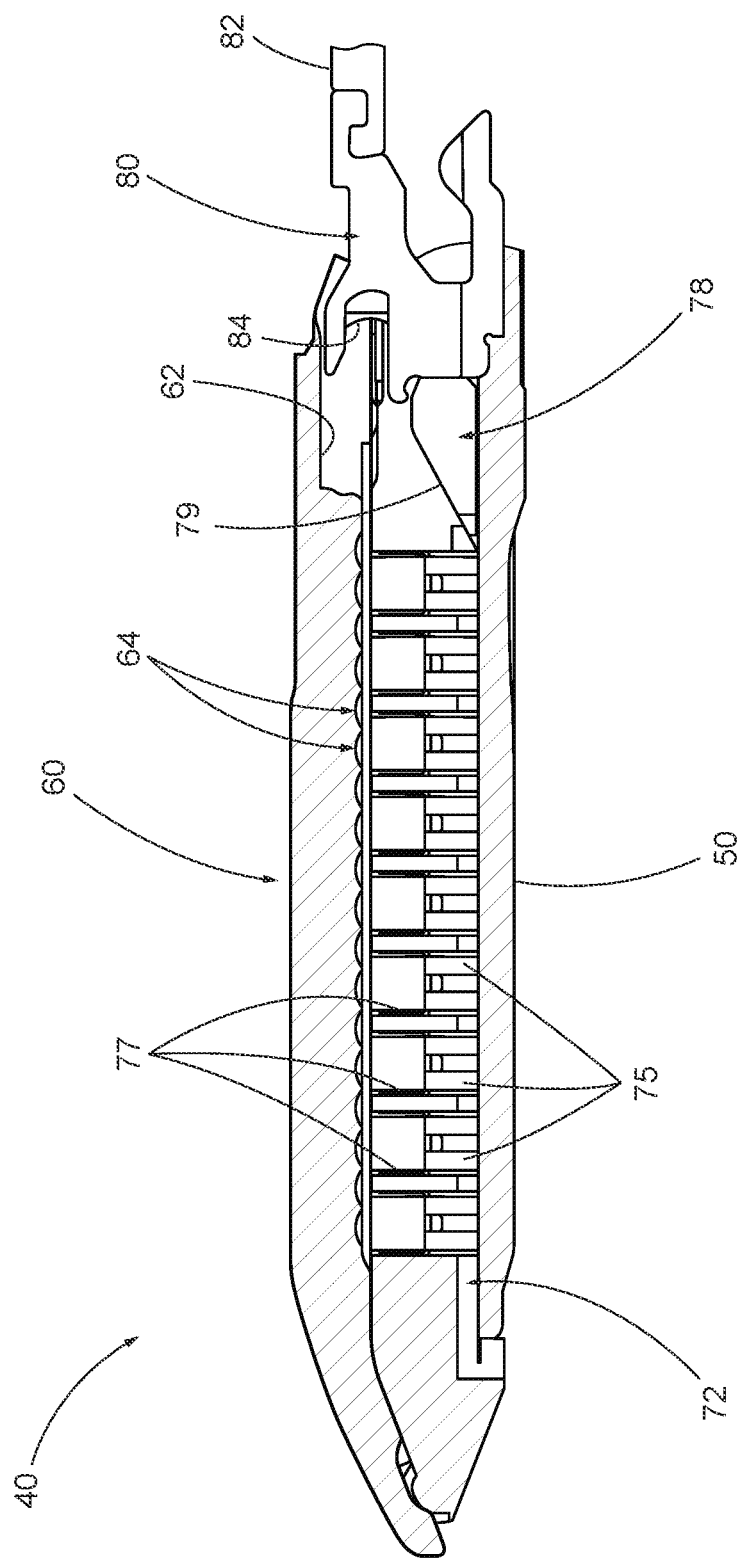
FIG. 7A depicts a cross-sectional side view of the end effector of FIG. 3, taken along line 7-7 of FIG. 4, with a firing beam in a proximal position.

As best seen in FIGS. 4-6, staple cartridge (70) of the present example comprises a cartridge body (71) and a tray (76) secured to the underside of cartridge body (71). The upper side of cartridge body (71) presents a deck (73), against which tissue may be compressed when anvil (60) is in a closed position. Cartridge body (71) further defines a longitudinally extending channel (72) and a plurality of staple pockets (74). A staple (77) is positioned in each staple pocket (74). A staple driver (75) is also positioned in each staple pocket (74), underneath a corresponding staple (77), and above tray (76). As will be described in greater detail below, staple drivers (75) are operable to translate upwardly in staple pockets (74) to thereby drive staples (77) upwardly through staple pockets (74) and into engagement with anvil (60). Staple drivers (75) are driven upwardly by a wedge sled (78), which is captured between cartridge body (71) and tray (76), and which translates longitudinally through cartridge body (71). Wedge sled (78) includes a pair of obliquely angled cam surfaces (79), which are configured to engage staple drivers (75) and thereby drive staple drivers (75) upwardly as wedge sled (78) translates longitudinally through cartridge (70). For instance, when wedge sled (78) is in a proximal position as shown in FIG. 7A, staple drivers (75) are in downward positions and staples (77) are located in staple pockets (74). As wedge sled (78) is driven to the distal position shown in FIG. 7B by a translating knife member (80), wedge sled (78) drives staple drivers (75) upwardly, thereby driving staples (77) out of staple pockets (74) and into staple forming pockets (64). Thus, staple drivers (75) translate along a vertical dimension as wedge sled (78) translates along a horizontal dimension.

It should be understood that the configuration of staple cartridge (70) may be varied in numerous ways. For instance, staple cartridge (70) of the present example includes two longitudinally extending rows of staple pockets (74) on one side of channel (72); and another set of two longitudinally extending rows of staple pockets (74) on the other side of channel (72). However, in some other versions, staple cartridge (70) includes three, one, or some other number of staple pockets (74) on each side of channel (72). In some versions, staple cartridge (70) is constructed and operable in accordance with at least some of the teachings of U.S. Pub. No. 2014/0239042, entitled "Integrated Tissue Positioning and Jaw Alignment Features for Surgical Stapler," published Aug. 28, 2014, the disclosure of which is incorporated by reference herein. In addition or in the alternative, staple cartridge (70) may be constructed and operable in accordance with at least some of the teachings of U.S. Pub. No. 2014/0239044, entitled "Installation Features for Surgical Instrument End Effector Cartridge," published Aug. 28, 2014, issued as U.S. Pat. No. 9,517,065 on Dec. 13, 2016, the disclosure of which is incorporated by reference herein. Other suitable forms that staple cartridge (70) may take will be apparent to those of ordinary skill in the art in view of the teachings herein.

As best seen in FIG. 4, anvil (60) of the present example comprises a longitudinally extending channel (62) and a plurality of staple forming pockets (64). Channel (62) is configured to align with channel (72) of staple cartridge (70) when anvil (60) is in a closed position. Each staple forming pocket (64) is positioned to lie over a corresponding staple pocket (74) of staple cartridge (70) when anvil (60) is in a closed position. Staple forming pockets (64) are configured to deform the legs of staples (77) when staples (77) are driven through tissue and into anvil (60). In particular, staple forming pockets (64) are configured to bend the legs of staples (77) to secure the formed staples (77) in the tissue. Anvil (60) may be constructed in accordance with at least some of the teachings of U.S. Pub. No. 2014/0239042, entitled "Integrated Tissue Positioning and Jaw Alignment Features for Surgical Stapler," published Aug. 28, 2014, issued as U.S. Pat. No. 9,517,065 on Dec. 13, 2016; at least some of the teachings of U.S. Pub. No. 2014/0239036, entitled "Jaw Closure Feature for End Effector of Surgical Instrument," published Aug. 28, 2014, issued as U.S. Pat. no. 9,839,421 on Dec. 12, 2017; and/or at least some of the teachings of U.S. Pub. No. 2014/0239037, entitled "Staple Forming Features for Surgical Stapling Instrument," published Aug. 28, 2014, issued as U.S. Pat. No. 10,092,292 on Oct. 9, 2018, the disclosure of which is incorporated by reference herein. Other suitable forms that anvil (60) may take will be apparent to those of ordinary skill in the art in view of the teachings herein.

Figure 7B:
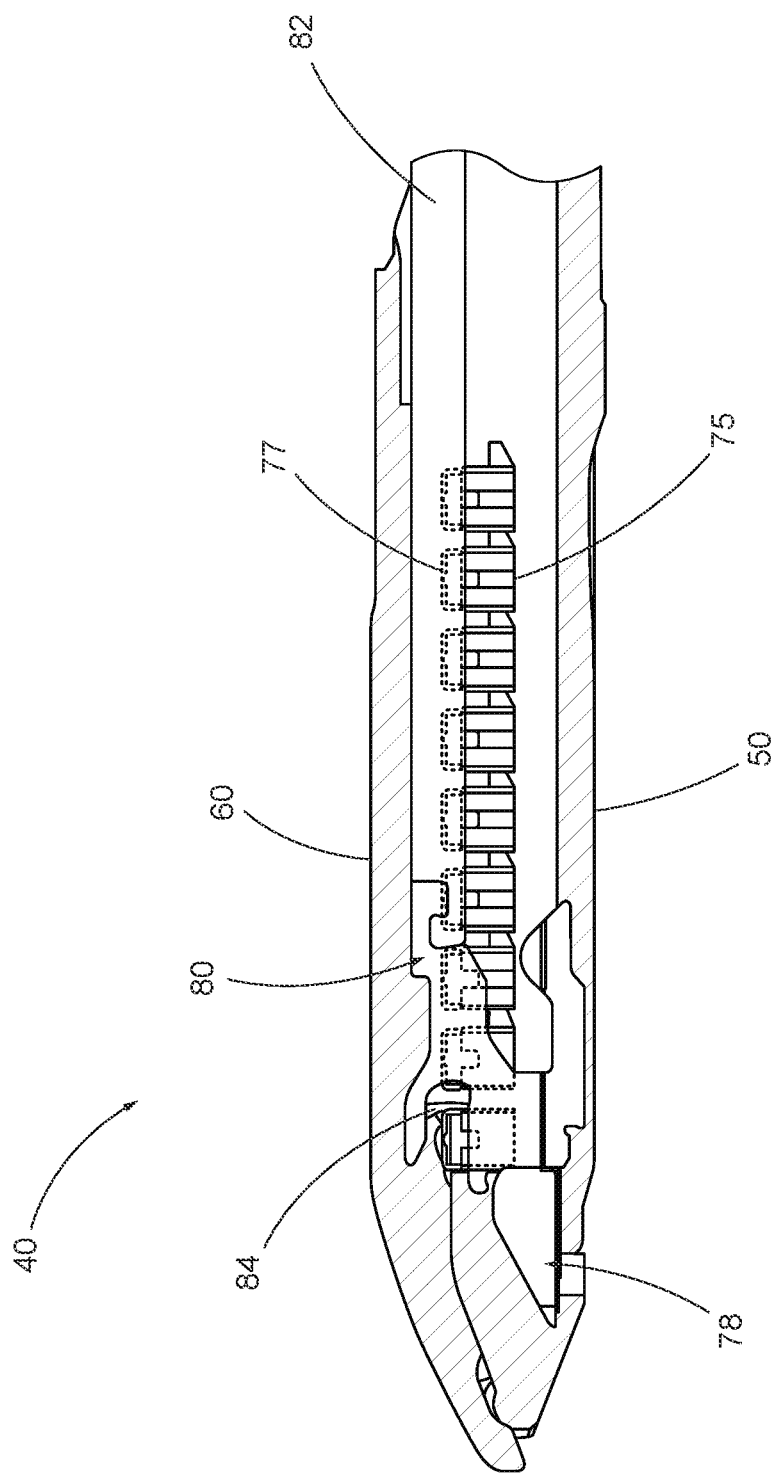
FIG. 7B depicts a cross-sectional side view of the end effector of FIG. 3, taken along line 7-7 of FIG. 4, with the firing beam in a distal position.

In the present example, knife member (80) is configured to translate through end effector (40). As best seen in FIGS. 5 and 7A-7B, knife member (80) is secured to the distal end of a firing beam (82), which extends through a portion of shaft assembly (30). As best seen in FIGS. 4 and 6, knife member (80) is positioned in channels (62, 72) of anvil (60) and staple cartridge (70). Knife member (80) includes a distally presented cutting edge (84) that is configured to sever tissue that is compressed between anvil (60) and deck (73) of staple cartridge (70) as knife member (80) translates distally through end effector (40). As noted above and as shown in FIGS. 7A-7B, knife member (80) also drives wedge sled (78) distally as knife member (80) translates distally through end effector (40), thereby driving staples (77) through tissue and against anvil (60) into formation. Various features that may be used to drive knife member (80) distally through end effector (40) will be described in greater detail below.

In some versions, end effector (40) includes lockout features that are configured to prevent knife member (80) from advancing distally through end effector (40) when a staple cartridge (70) is not inserted in lower jaw (50). In addition or in the alternative, end effector (40) may include lockout features that are configured to prevent knife member (80) from advancing distally through end effector (40) when a staple cartridge (70) that has already been actuated once (e.g., with all staples (77) deployed therefrom) is inserted in lower jaw (50). By way of example only, such lockout features may be configured in accordance with at least some of the teachings of U.S. Pub. No. 2014/0239041, entitled "Lockout Feature for Movable Cutting Member of Surgical Instrument," published Aug. 28, 2014, issued as U.S. Pat. No. 9,717,497 on Aug. 1, 2017, the disclosure of which is incorporated by reference herein; and/or at least some of the teachings of U.S. patent application Ser. No. 14/314,108, entitled "Method of Using Lockout Features for Surgical Staple cartridge," filed on Jun. 25, 2014, published as U.S. Pub. No. 2015/0374373 on Dec. 31, 2015, the disclosure of which is incorporated by reference herein. Other suitable forms that lockout features may take will be apparent to those of ordinary skill in the art in view of the teachings herein. Alternatively, end effector (40) may simply omit such lockout features.

C. Exemplary Actuation of Anvil

In the present example, anvil (60) is driven toward lower jaw (50) by advancing closure ring (36) distally relative to end effector (40). Closure ring (36) cooperates with anvil (60) through a camming action to drive anvil (60) toward lower jaw (50) in response to distal translation of closure ring (36) relative to end effector (40). Similarly, closure ring (36) may cooperate with anvil (60) to open anvil (60) away from lower jaw (50) in response to proximal translation of closure ring (36) relative to end effector (40). By way of example only, closure ring (36) and anvil (60) may interact in accordance with at least some of the teachings of U.S. Pub. No. 2014/0239036, entitled "Jaw Closure Feature for End Effector of Surgical Instrument," published Aug. 28, 2014, issued as U.S. Pat. No. 9,839,421 on Dec. 12, 2017, the disclosure of which is incorporated by reference herein; and/or in accordance with at least some of the teachings of U.S. patent application Ser. No. 14/314,108, entitled "Jaw Opening Feature for Surgical Stapler," filed on Jun. 25, 2014, published as U.S. Pub. No. 2015/0374373, the disclosure of which is incorporated by reference herein. Exemplary features that may be used to provide longitudinal translation of closure ring (36) relative to end effector (40) will be described in greater detail below.

As noted above, handle assembly (20) includes pistol grip (22) and closure trigger (24). As also noted above, anvil (60) is closed toward lower jaw (50) in response to distal advancement of closure ring (36). In the present example, closure trigger (24) is pivotable toward pistol grip (22) to drive closure tube (32) and closure ring (36) distally. Various suitable components that may be used to convert pivotal movement of closure trigger (24) toward pistol grip (22) into distal translation of closure tube (32) and closure ring (36) relative to handle assembly (20) will be apparent to those of ordinary skill in the art in view of the teachings herein. When closure trigger (24) reaches a fully pivoted state, such that anvil (60) is in a fully closed position relative to lower jaw (50), locking features in handle assembly (20) lock the position of closure trigger (24) and closure tube (32), thereby locking anvil (60) in a fully closed position relative to lower jaw (50). These locking features are released by actuation of anvil release button (25). Anvil release button (25) is configured and positioned to be actuated by the thumb of the operator hand that grasps pistol grip (22). In other words, the operator may grasp pistol grip (22) with one hand, actuate closure trigger (24) with one or more fingers of the same hand, and then actuate anvil release button (25) with the thumb of the same hand, without ever needing to release the grasp of pistol grip (22) with the same hand. Other suitable features that may be used to actuate anvil (60) will be apparent to those of ordinary skill in the art in view of the teachings herein.

D. Exemplary Actuation of Firing Beam

In the present example, instrument (10) provides motorized control of firing beam (82). In particular, instrument (10) includes motorized components that are configured to drive firing beam (82) distally in response to pivoting of firing trigger (26) toward pistol grip (22). In some versions, a motor (not shown) is contained in pistol grip (22) and receives power from battery pack (28). This motor is coupled with a transmission assembly (not shown) that converts rotary motion of a drive shaft of the motor into linear translation of firing beam (82). In some such versions, firing beam (82) may only be advanced distally when anvil (60) is in a fully closed position relative to lower jaw (50). After firing beam (82) is advanced distally to sever tissue and drive staples (77) as described above with reference to FIGS. 7A-7B, the drive assembly for firing beam (82) may be automatically reversed to drive firing beam (82) proximally back to the retracted position (e.g., back from the position shown in FIG. 7B to the position shown in FIG. 7A). Alternatively, the operator may actuate firing beam reverse switch (27), which may reverse the drive assembly for firing beam (82) in order to retract firing beam (82) to a proximal position. Handle assembly (20) of the present example further includes a bailout feature (21), which is operable to provide a mechanical bailout allowing the operator to manually retract firing beam (82) proximally (e.g., in the event of power loss while firing beam (82) is in a distal position, etc.).

By way of example only, the features that are operable to provide motorized actuation of firing beam (82) may be configured and operable in accordance with at least some of the teachings of U.S. Pat. No. 8,210,411, entitled "Motor-Driven Surgical Instrument," issued Jul. 3, 2012, the disclosure of which is incorporated by reference herein. As another merely illustrative example, the features that are operable to provide motorized actuation of firing beam (82) may be configured and operable in accordance with at least some of the teachings of U.S. Pat. No. 8,453,914, entitled "Motor-Driven Surgical Cutting Instrument with Electric Actuator Directional Control Assembly," issued Jun. 4, 2013, the disclosure of which is incorporated by reference herein. As yet another merely illustrative example, the features that are operable to provide motorized actuation of firing beam (82) may be configured and operable in accordance with at least some of the teachings of U.S. patent application Ser. No. 14/226,142, entitled "Surgical Instrument Comprising a Sensor System," filed Mar. 26, 2014, issued as U.S. Pat. No. 9,913,642 on Mar. 13, 2018, the disclosure of which is incorporated by reference herein.

Other suitable components, features, and configurations that may be used to provide motorization of firing beam (82) will be apparent to those of ordinary skill in the art in view of the teachings herein. It should also be understood that some other versions may provide manual driving of firing beam (82), such that a motor may be omitted. By way of example only, firing beam (82) may be manually actuated in accordance with at least some of the teachings of any other reference cited herein.

Figure 8:
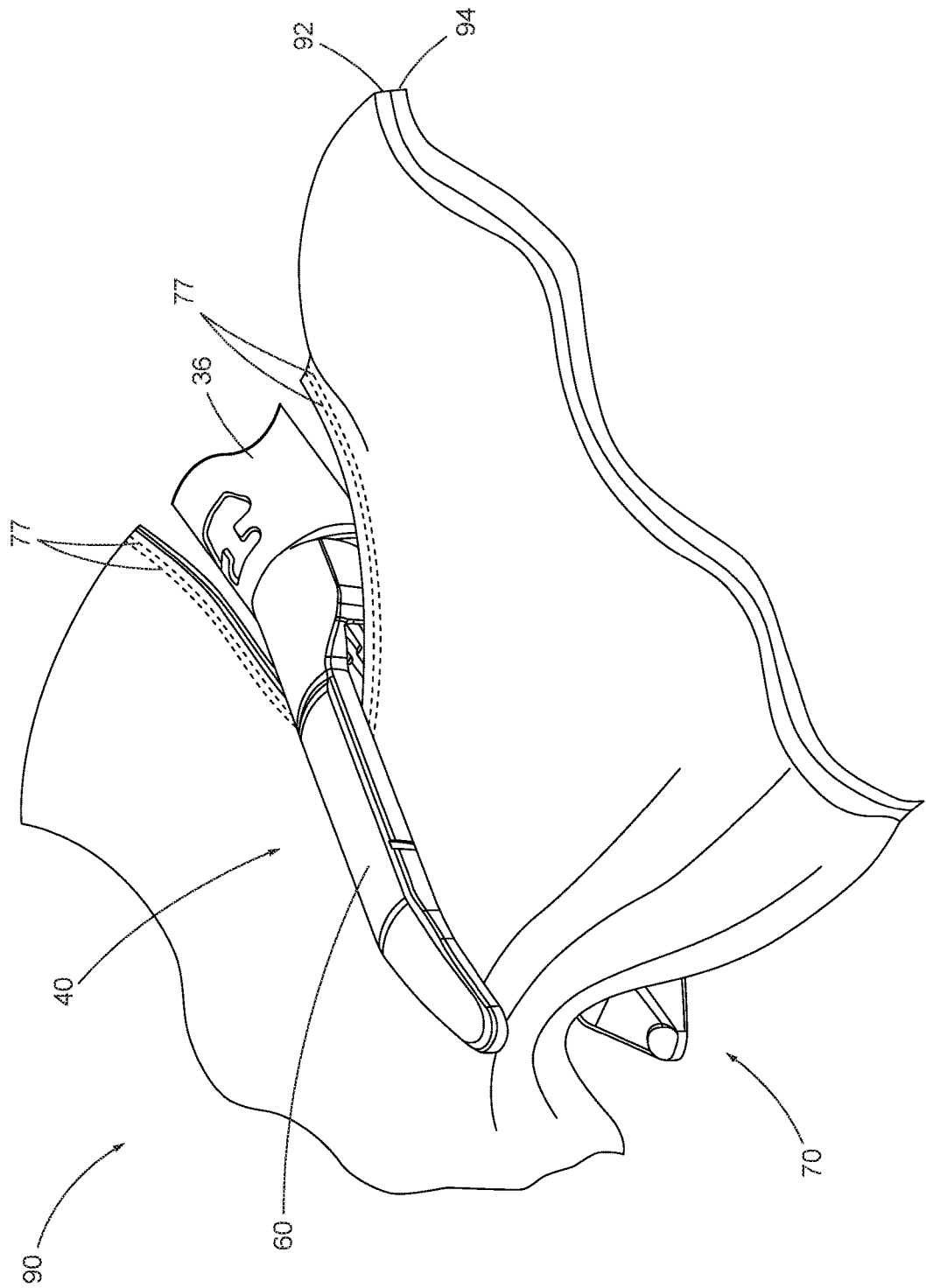
FIG. 8 depicts a perspective view of the end effector of FIG. 3, positioned at tissue and having been actuated once in the tissue.
Figure 9:
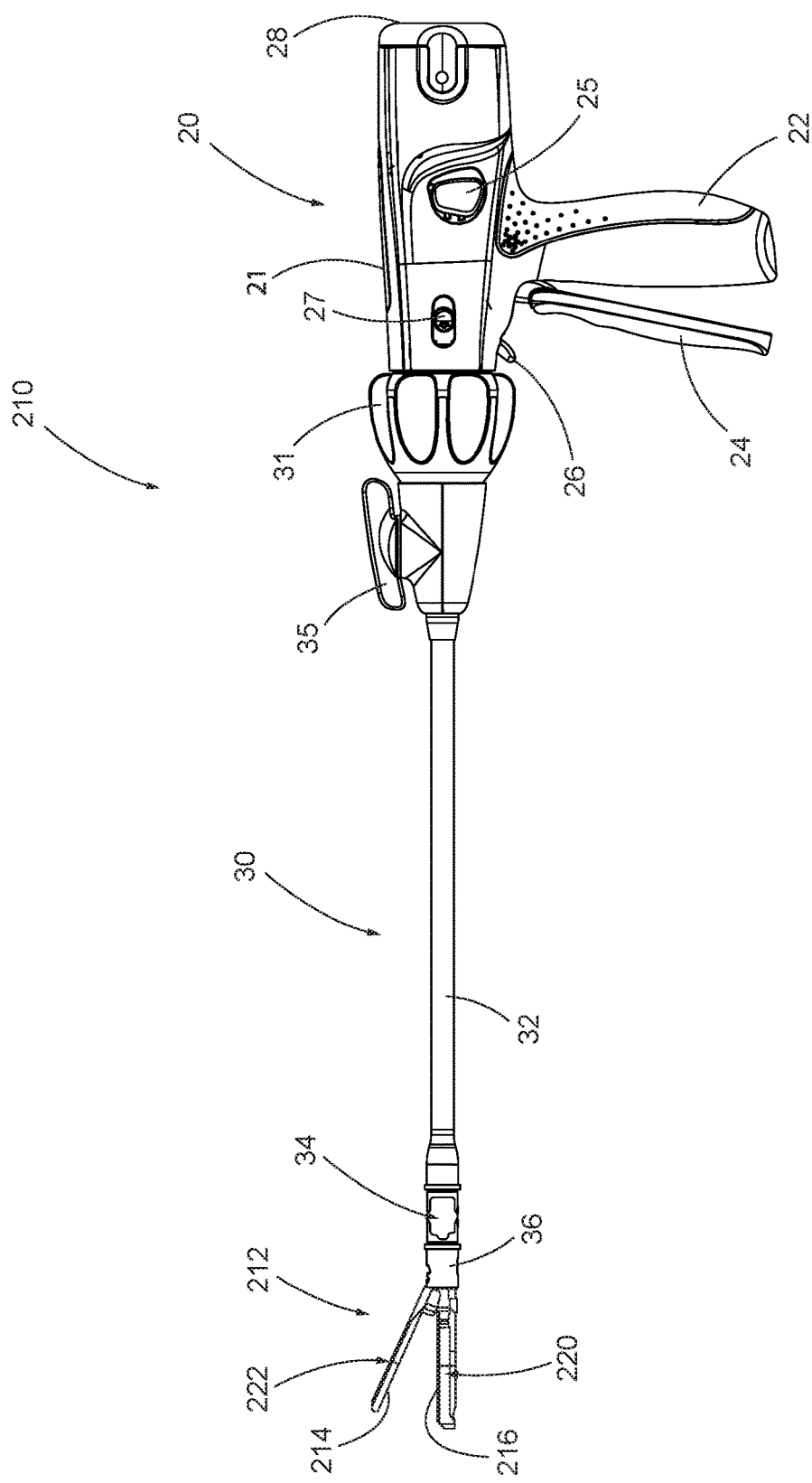
FIG. 9 depicts a side elevational view of another exemplary articulating surgical stapling instrument.

FIG. 8 shows end effector (40) having been actuated through a single stroke through tissue (90). As shown, cutting edge (84) (obscured in FIG. 8) has cut through tissue (90), while staple drivers (75) have driven two alternating rows of staples (77) through the tissue (90) on each side of the cut line produced by cutting edge (84). Staples (77) are all oriented substantially parallel to the cut line in this example, though it should be understood that staples (77) may be positioned at any suitable orientations. In the present example, end effector (40) is withdrawn from the trocar after the first stroke is complete, the spent staple cartridge (70) is replaced with a new staple cartridge (70), and end effector (40) is then again inserted through the trocar to reach the stapling site for further cutting and stapling. This process may be repeated until the desired amount of cuts and staples (77) have been provided. Anvil (60) may need to be closed to facilitate insertion and withdrawal through the trocar; and anvil (60) may need to be opened to facilitate replacement of staple cartridge (70).

It should be understood that cutting edge (84) may cut tissue substantially contemporaneously with staples (77) being driven through tissue during each actuation stroke. In the present example, cutting edge (84) just slightly lags behind driving of staples (77), such that staple (77) is driven through the tissue just before cutting edge (84) passes through the same region of tissue, though it should be understood that this order may be reversed or that cutting edge (84) may be directly synchronized with adjacent staples. While FIG. 8 shows end effector (40) being actuated in two layers (92, 94) of tissue (90), it should be understood that end effector (40) may be actuated through a single layer of tissue (90) or more than two layers (92, 94) of tissue. It should also be understood that the formation and positioning of staples (77) adjacent to the cut line produced by cutting edge (84) may substantially seal the tissue at the cut line, thereby reducing or preventing bleeding and/or leaking of other bodily fluids at the cut line. Furthermore, while FIG. 8 shows end effector (40) being actuated in two substantially flat, apposed planar layers (92, 94) of tissue, it should be understood that end effector (40) may also be actuated across a tubular structure such as a blood vessel, a section of the gastrointestinal tract, etc. FIG. 8 should therefore not be viewed as demonstrating any limitation on the contemplated uses for end effector (40). Various suitable settings and procedures in which instrument (10) may be used will be apparent to those of ordinary skill in the art in view of the teachings herein.

It should also be understood that any other components or features of instrument (10) may be configured and operable in accordance with any of the various references cited herein. Additional exemplary modifications that may be provided for instrument (10) will be described in greater detail below. Various suitable ways in which the below teachings may be incorporated into instrument (10) will be apparent to those of ordinary skill in the art. Similarly, various suitable ways in which the below teachings may be combined with various teachings of the references cited herein will be apparent to those of ordinary skill in the art. It should also be understood that the below teachings are not limited to instrument (10) or devices taught in the references cited herein. The below teachings may be readily applied to various other kinds of instruments, including instruments that would not be classified as surgical staplers. Various other suitable devices and settings in which the below teachings may be applied will be apparent to those of ordinary skill in the art in view of the teachings herein.

II. Exemplary Alternative Stapling End Effector

While the above surgical instrument (10) provides one example of an end effector (40) that may be used to staple and sever tissue within a patient, it will be appreciated that the human body is comprised a wide variety of tissues located in distinct, sometimes difficult to access regions throughout the patient. For example, a liver includes tissue including vessels or ducts passing throughout. In settings where the liver includes a tumor, it may be desirable to resect the portion of the liver containing the tumor. The resection may be anatomic (e.g., resection of the right or left side of the liver, inclusive of the lobes on that side) or non-anatomic (e.g., resection of just a single lobe or wedge of liver tissue). This resection process may entail at least three kinds of steps—a first step to dissect the tissue (e.g., liver parenchyma) around the vessels or ducts, to thereby isolate or reveal the vessels or ducts; a second step to ligate those vessels or ducts; and a third step to sever the ligated vessels or ducts.

One such method of liver resection includes the well known Kelly clamp method, where a Kelly style clamp is used to compress the liver tissue and thereby dissect the tissue through a crushing action. However, treatments may require many instruments to accommodate such a wide variety of tissues and vessels or ducts within the human body, thereby adding to the time and complexity associated with assessing the state of the tissue, selecting and/or changing instruments, and performing the resection. It may therefore be desirable to provide a surgical instrument (210, 410) with an end effector (212, 412) having a pair of crush surfaces (214, 216, 414, 416) that are configured to sever tissue by crushing the tissue; while also providing an adjacent staple cartridge (218, 418) to selectively ligate one or more vessels or ducts passing through the tissue. Thereby, a single surgical instrument (210, 410) will allow the operator to more quickly assess the tissue and proceed with further tissue dissection and/or ligation of vessels and ducts.

Surrgical instruments (210, 410) are described below in the context of dissecting liver tissue (e.g., liver parenchyma) with crush surfaces (214, 216, 414, 416) and using staples to ligate associated vessels or ducts (e.g., portal vein, hepatic vein branches, hepatic artery branches, extrahepatic vessels, etc.). In some instances (e.g., in the case of hepatic vein branches and hepatic artery branches, etc.), the vessel or duct that is sealed by the staples is exposed when the operator crushes the liver tissue with surfaces (214, 216, 414, 416). In some other instances (e.g., in the case of the portal vein and extrahepatic vessels, etc.), the vessel or duct that is sealed by the staples is separate from the liver tissue that the operator has crushed with surfaces (214, 216, 414, 416). While the following description of surgical instruments (210, 410) and method of treatment is provided in the context of liver resection, it will be appreciated that surgical instruments (210, 410) may be alternatively configured to treat any tissue in the human body with similar features. It should also be understood that that the features discussed below may be readily incorporated into surgical instrument (10) discussed above. To this end, like numbers indicate like features described above in greater detail.

In the following examples, end effectors (212, 412) apply at least two laterally spaced apart rows of staples where the staples in one row have the same height as the staples in another row. In some variations, end effectors (212, 412) are modified to apply at least two laterally spaced apart rows of staples where the staples in one row have a height that is different from the height of the staples in another row A. Exemplary Stapling Instrument with Curved End Effector FIGS. 9-12 show surgical instrument (210) with end effector (212) having upper crush surface (214), lower crush surface (216) and staple cartridge (218). Surgical instrument (210) also includes handle assembly (20) and shaft assembly (30) discussed above in greater detail. Except as otherwise described below, end effector (212), in conjunction with handle assembly (20) and shaft assembly (30), is configured and operable similar to end effector (40) (see FIG. 1).

End effector (212) of the present example further includes a lower jaw (220) and an upper jaw (222). Upper jaw (222) forms an anvil (224) and is pivotally mounted relative to lower jaw (220) for receiving the tissue therebetween. More particularly, anvil (224) is pivotable toward and away from lower jaw (220) between an open position and a closed position (e.g., in response to pivotal movement of trigger (24) toward and away from pistol grip (22)). For instance, in the present example, anvil (224) pivots about an axis that is defined by pins (not shown), which slide along curved slots (not shown) of lower jaw (220) as anvil (224) moves toward lower jaw (220). In such versions, the pivot axis translates along the path defined by slots (not shown) while anvil (224) simultaneously pivots about that axis. In addition or in the alternative, the pivot axis may slide along slots (not shown) first, with anvil (224) then pivoting about the pivot axis after the pivot axis slides a certain distance along the slots (not shown). Alternatively, some versions may provide pivotal movement of anvil (224) about an axis that remains fixed and does not translate within a slot or channel, etc.

Figure 10:
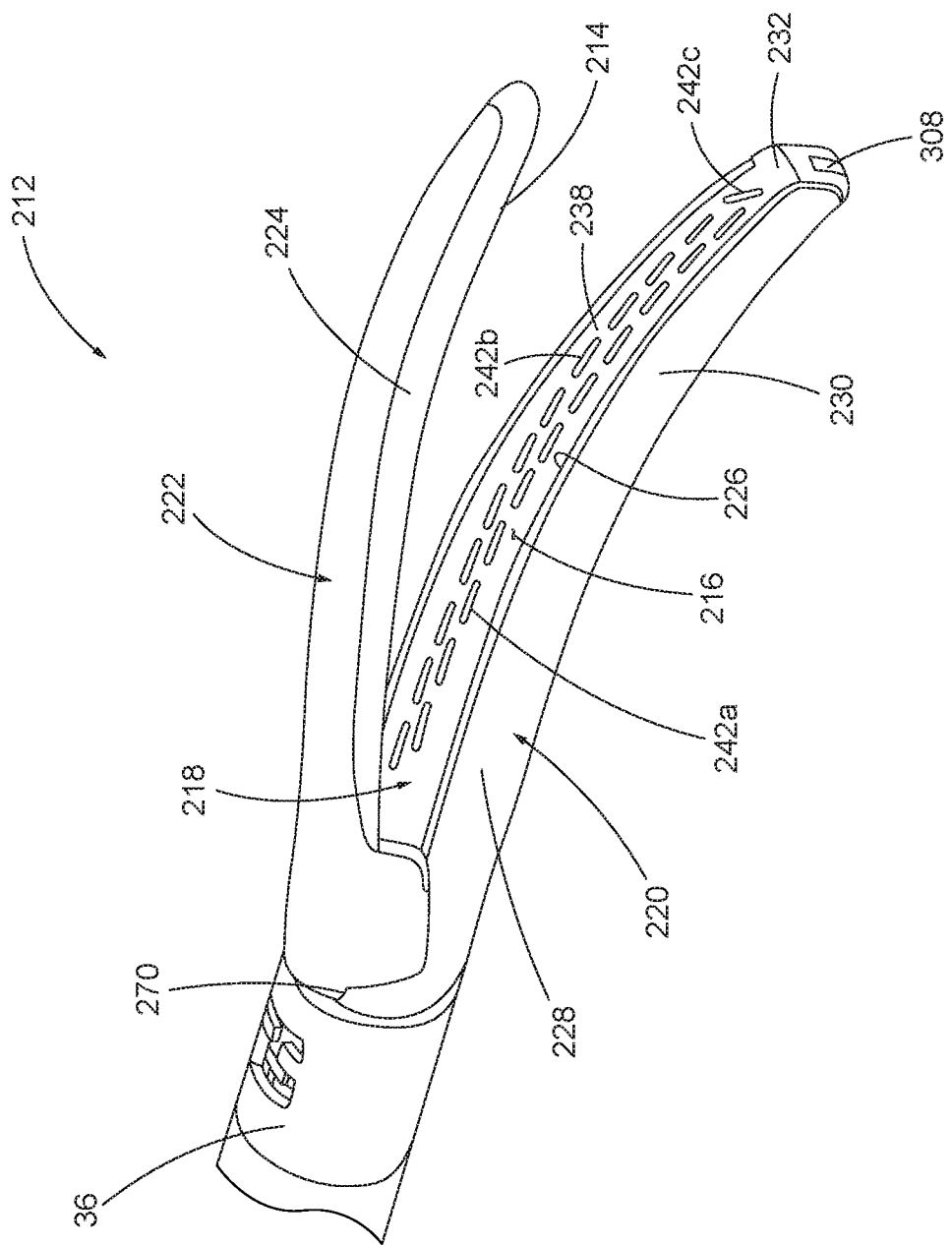
FIG. 10 depicts a perspective view of an end effector of the instrument of FIG. 9, with the end effector in an open configuration.
Figure 11:
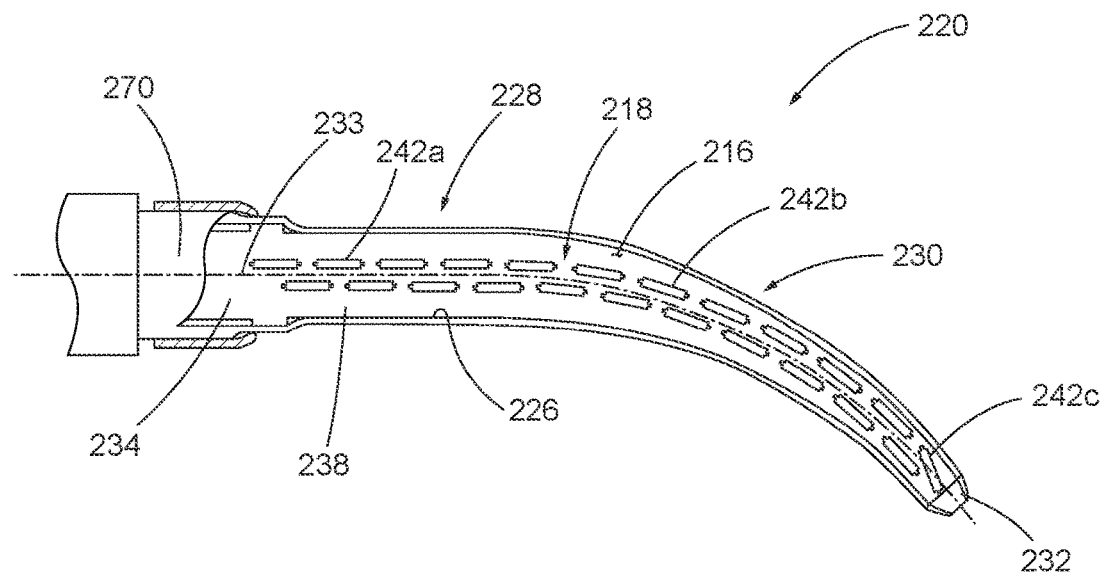
FIG. 11 depicts a top view of a lower jaw of the end effector of FIG. 10.

As best seen in FIG. 10 and FIG. 11, lower jaw (220) of the present example defines a channel (226) that is configured to receive staple cartridge (218). Staple cartridge (218) may be inserted into channel (226), end effector (212) may be actuated, and then staple cartridge (218) may be removed and replaced with another staple cartridge (218). Lower jaw (220) thus releasably retains staple cartridge (218) in alignment with anvil (224) for actuation of end effector (212). In some alternative versions, the components of staple cartridge (218) are fully integrated into lower jaw (220) such that end effector (212) may only be used once. Other suitable forms that lower jaw (220) may take will be apparent to those of ordinary skill in the art in view of the teachings herein.

Figure 12:
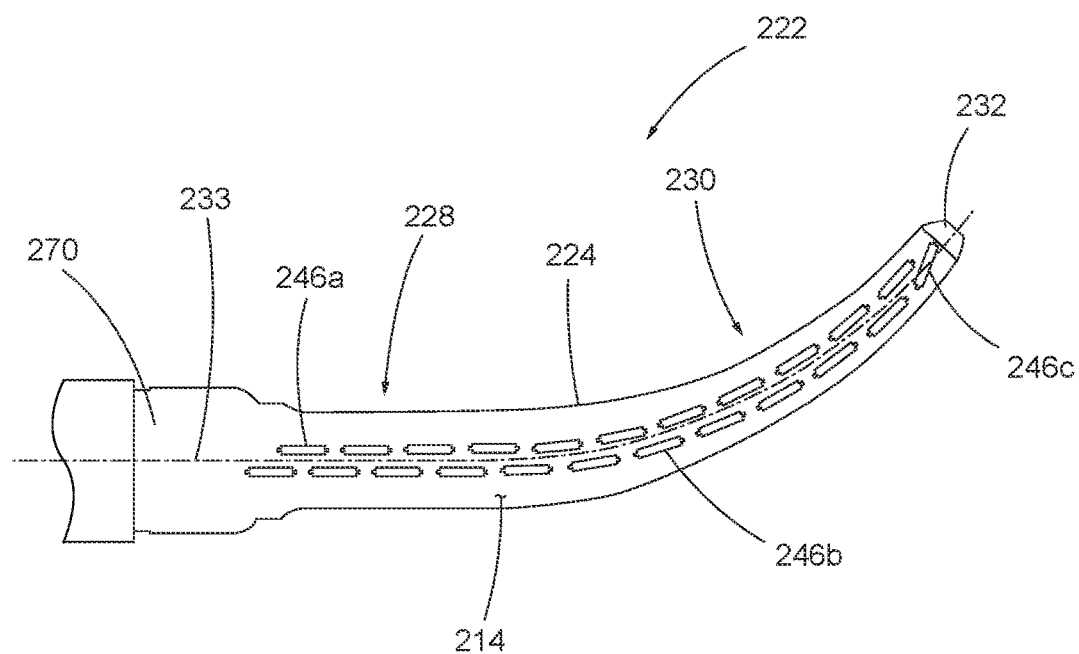
FIG. 12 depicts a bottom view of an upper jaw of the end effector of FIG. 10.

End effector (212) is generally shaped for improved access to the tissue during the surgical procedure. More particularly, end effector (212) has a linear portion (228) that projects from closure ring (36) and extends to an arcuate portion (230). Arcuate portion (230) in one example curves transversely to the right (when viewed from above) relative to the linear portion (228). However, it will be appreciated that the arcuate portion (230) may alternatively curve transversely to the left (when viewed from above) relative to the linear portion (228). In any case, lower and upper jaws (220, 222) define the linear and arcuate portions (228, 230) as shown in FIG. 11 and FIG. 12. In addition, lower and upper jaws (220, 222) are tapered such that the end effector narrows in the transverse dimension toward a distal tip (232) of the end effector (212) for further access within the tissue. As such, a centerline (233) along a transverse width of end effector (212) extends longitudinally along end effector (212) following linear and arcuate portions (228, 230) thereof.

Staple cartridge (218) accommodates the shape of lower and upper jaws (220, 222) by further defining the linear and arcuate portions (228, 230) and tapering of end effector (212). To this end, staple cartridge (218) of the present example comprises a cartridge body (234) and a tray (236) (see FIG. 18) secured to an underside of cartridge body (234). An upper side of cartridge body (234) presents a deck (238), against which tissue may be compressed when anvil (224) is in a closed position. In some versions, lower crush surface (216) is positioned along staple cartridge (218). However, it will be appreciated that lower crush surface (216), as well as cooperating upper crush surface (214), may be alternatively positioned along end effector (212) for severing tissue via compression.

Cartridge body (234) further defines a plurality of staple pockets (242a, 242b, 242c) following a predetermined pattern along the centerline (233) of deck (238). More particularly, staple cartridge (218) includes two longitudinally extending rows of staple pockets (242a, 242b, 242c), with a left row on a left side of the centerline (233) and a right row on a right side of the centerline (233).

One of a plurality of staples (244a, 244b, 244c) is positioned in respective staple pockets (242a, 242b, 242c). The left and right rows of staple pockets (242a, 242b, 242c) are configured to overlap in a direction transverse to the centerline (233) in order to install the plurality of staples (244a, 244b, 244c) within the tissue and inhibit openings therebetween, for improved ligation. In other words, a consistent gap (G1) is maintained between adjacent staple pockets (242a, 242b, 242c) for consistent overlap in the present example. As used herein, the term "overlap" is intended to include one feature overlapping with another in at least one direction. Thus, a feature may be offset from another feature and still overlap as described herein in the event that these features overlap in at least one plane, such as a transverse plane including the transverse direction. While exemplary cartridge body (234) includes a variety of staple pockets (242a, 242b, 242c) with staples (244a, 244b, 244c) in order to accommodate the arcuate portion (230) as discussed below in additional detail, it should be understood that the configuration of staple cartridge (218) may be varied in numerous ways. Other suitable forms that staple cartridge (218) may take will be apparent to those of ordinary skill in the art in view of the teachings herein.

As best seen in FIG. 12, anvil (224) of the present example has a plurality of staple forming pockets (246a, 246b, 246c). Each staple forming pocket (246a, 246b, 246c) is positioned to lie over a corresponding staple pocket (242a, 242b, 242c) of staple cartridge (218) when anvil (224) is in a closed position. Staple forming pockets (246a, 246b, 246c) are configured to deform each leg (248) of staples (244a, 244b, 244c) when staples (244a, 244b, 244c) are driven through tissue and into anvil (224). In particular, staple forming pockets (246a, 246b, 246c) are configured to bend legs (248) of staples (244a, 244b, 244c) to secure the formed staples (244a, 244b, 244c) in the tissue. Other suitable forms that anvil (224) may take will be apparent to those of ordinary skill in the art in view of the teachings herein.

Figure 13:
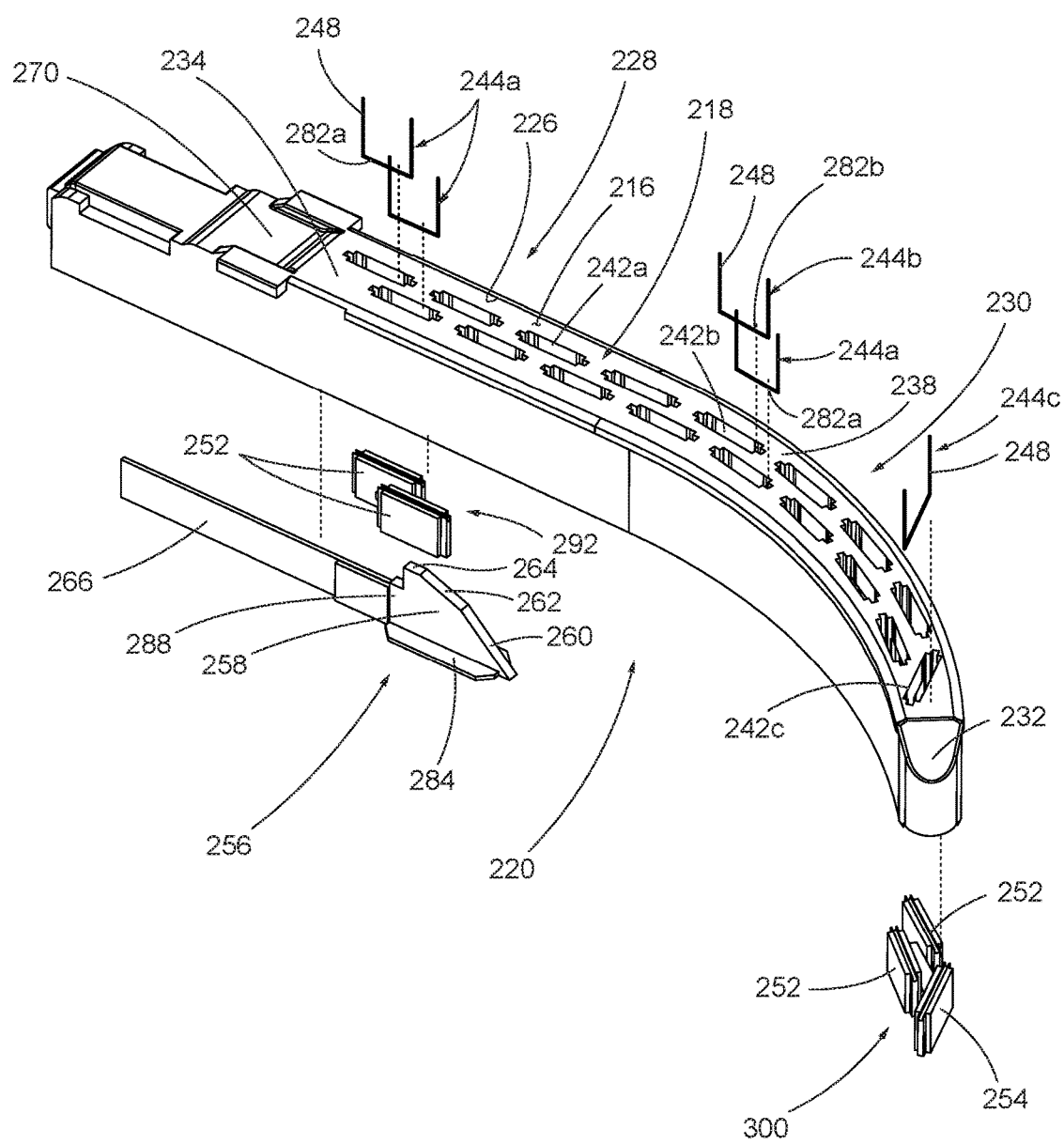
FIG. 13 depicts an exploded perspective view of the lower jaw of FIG. 11.
Figure 18:
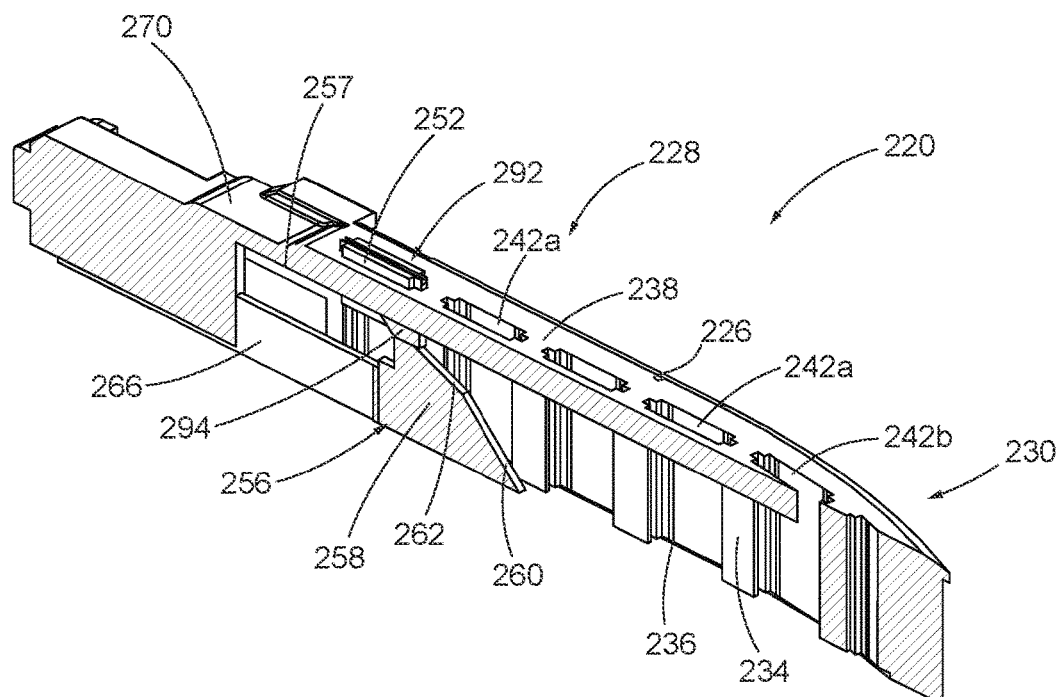
FIG. 18 depicts a cross-sectional perspective view of the lower jaw of FIG. 11, taken along section line 18-18 of FIG. 17.

As shown in FIG. 13, staple cartridge (218) includes staple row drivers (252) and a cross staple driver (254) positioned in staple pockets (242a, 242b, 242c), underneath corresponding sets of staples (244a, 244b, 244c), and above tray (236) (see FIG. 18). As will be described in greater detail below, staple drivers (252, 254) are operable to translate upwardly in staple pockets (242a, 242b, 242c) to thereby drive staples (244a, 244b, 244c) upwardly through staple pockets (242a, 242b, 242c) and into engagement with anvil (224). Staple drivers (252, 254) are driven upwardly by a distally translating wedge sled (256), which is captured between cartridge body (234) and tray (236) (see FIG. 18), and which translates longitudinally through cartridge body (234) along a cam slot (257). Wedge sled (256) includes a cam ramp (258) having a leading cam surface (260), an intermediate cam surface (262), and a trailing cam surface (264). By way of example only, leading cam surface (260) may be angled at approximately 45° relative to a horizontal plane; and intermediate cam surface (262) may be angled at approximately 22° relative to a horizontal plane. Alternatively, any other suitable angles may be used. Cam ramp (258) is generally configured to engage staple drivers (252, 254) and thereby drive staple drivers (252, 254) upwardly as wedge sled (256) translates longitudinally through staple cartridge (218) from a proximal sled position to a distal sled position. For instance, when wedge sled (256) is in the proximal sled position, staple drivers (252, 254) are in downward positions and staples (244a, 244b, 244c) are located in staple pockets (442) below deck (238).

Wedge sled (256) is driven distally by a translating member (266). By way of example only, translating member (266) may be translated distally by actuating trigger (26)). Translating member (266) may thus operate in a manner similar to firing beam (82) described above, though translating member (266) lacks a cutting edge (84) and is unable to otherwise sever tissue. As wedge sled (256) is driven to the distal sled position by translating member (266), wedge sled (256) drives staple drivers (252, 254) upwardly, thereby driving staples (244a, 244b, 244c) out of staple pockets (242a, 242b, 242c) and into staple forming pockets (246a, 246b, 246c). Thus, staple drivers (252, 254) translate along corresponding vertical planes as wedge sled (256) translates along a horizontal plane.

1. Exemplary Upper and Lower Crush Surfaces of End Effector

Figure 14:
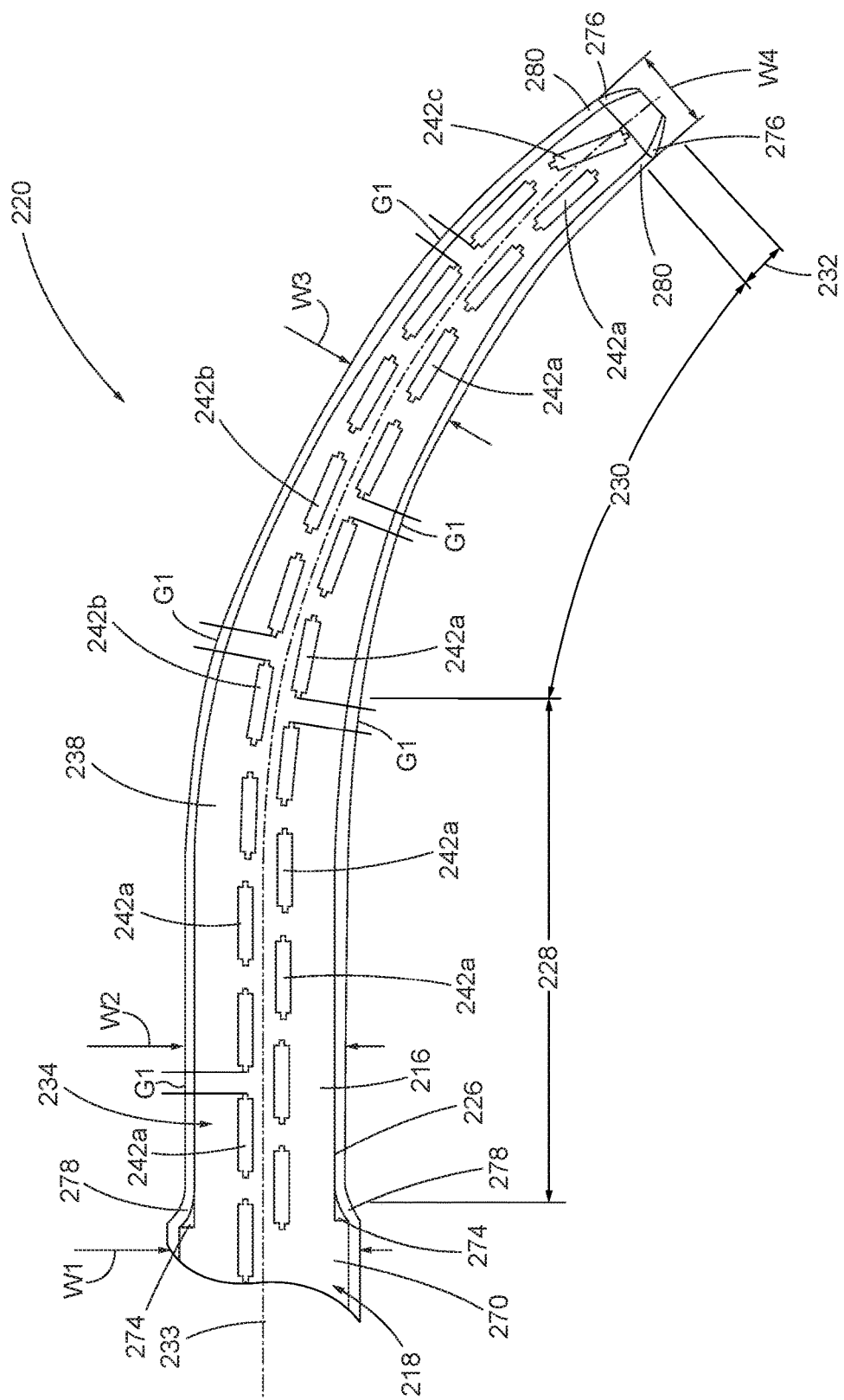
FIG. 14 depicts a top view of the lower jaw of FIG. 11.
Figure 15:
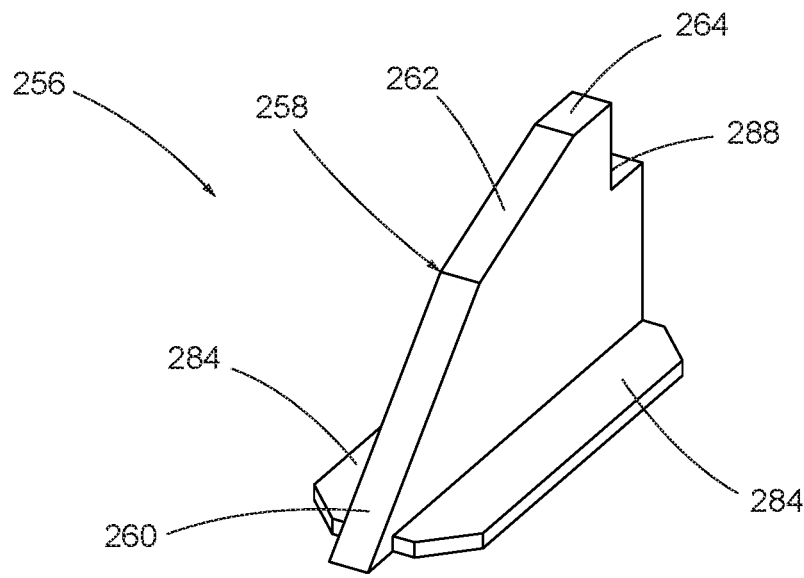
FIG. 15 depicts a perspective view of a wedge sled of the lower jaw of FIG. 11.
Figure 16:
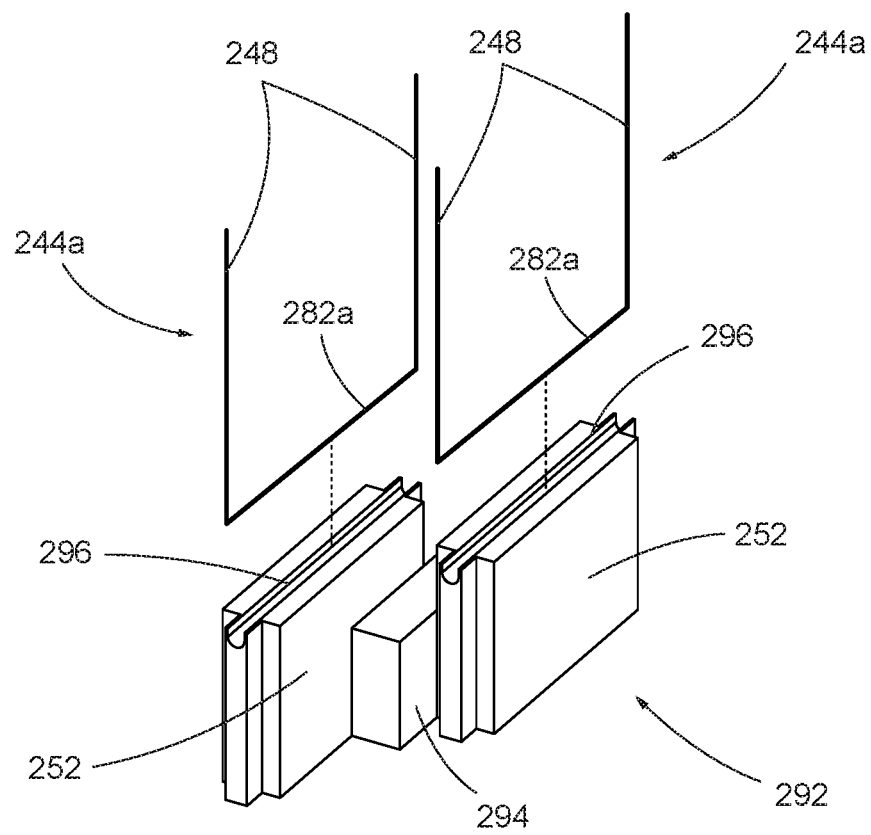
FIG. 16 depicts a perspective view of a staple row driver assembly of the lower jaw of FIG. 11.
Figure 17:
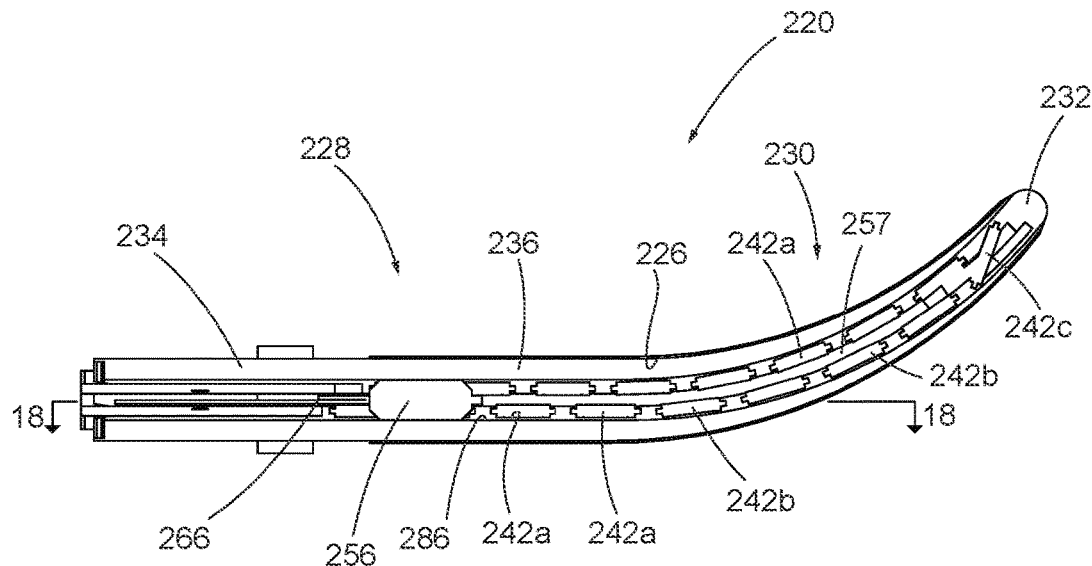
FIG. 17 depicts a bottom cross-sectional view of the lower jaw of FIG. 11, with the staple row driver assembly of FIG. 16 omitted.

As shown in FIGS. 12-14, end effector (212) includes upper and lower crush surfaces (214, 216) extending along linear and arcuate portions (228, 230) thereof, as discussed briefly above. To this end, upper crush surface (214) is defined by a bottom surface of anvil (224) extending about the centerline (233) and surrounding each staple forming pocket (246a, 246b, 246c). Lower crush surface (216) is similarly defined by a top surface of deck (238) extending about the centerline (233) and surrounding staple pocket (242a, 242b, 242c). In the closed position, lower and upper jaws (220, 222) clamp together with lower crush surface (216) compressed directly against upper crush surface (214) with a predetermined crush pressure therebetween. The predetermined crush pressure is configured to sever a layer of tissue captured between surfaces (214, 216), while vessels or ducts within the layer of tissue remain unsevered. As such, the vessels or ducts may be left intact or ligated via the staples (244). In the event of ligation, the operator may remove surgical instrument (210) (see FIG. 2) from the stapled tissue and then cut the vessel or duct using any suitable surgical instrument known in the art that is configured to appropriately cut the vessel or duct.

In addition, the narrowing of end effector (212) distally along centerline (233) also continuously increases the predetermined crush pressure that may be applied between upper and lower crush surfaces (214, 216) due to the reduction of contact surface area therebetween. As such, narrowing of end effector (212) along centerline (233) also increases compression capabilities of end effector (212) in narrower portions, such as arcuate portion (230), relative to wider portions, such as linear portion (228). In the present example, upper crush surface (214) is located on anvil (224), and lower crush surface (216) is located on deck (238). However, it will be appreciated that upper and lower crush surfaces (214, 216) may be alternatively located respectively on upper and lower jaws (222, 220) for severing tissue. As such, other suitable configurations of upper and lower crush surfaces (214, 216) will be apparent to persons skilled in the art in view of the teachings herein.

2. Exemplary Linear and Arcuate Portions of End Effector

End effector (212) with linear and arcuate portions (228, 230) is configured to provide greater access to tissue within the patient during treatment. FIG. 13 and FIG. 14 show lower jaw (220) in greater detail having four distinct portions extending longitudinally in order along centerline (233) from a proximal end portion (270) of lower jaw (220), linear portion (228), arcuate portion (230), to distal tip (232) of staple cartridge (218). As such, channel (226) in lower jaw (220) is configured to receive staple cartridge (218) and collectively define these portions (270, 228, 230, 232).

Lower jaw (220) of the present example contains staple cartridge (218) within channel (226) between abutments (272, 274) of staple cartridge (218) and corresponding abutments (276, 278) of lower jaw (220) as shown in FIG. 14. Channel (226) thus effectively cradles staple cartridge (218), where abutments (272, 274) of staple cartridge (218) are captured by corresponding abutments (276, 278) of lower jaw (220) for securing staple cartridge (218) in the horizontal plane. Lower jaw (220) and staple cartridge (218) are also provided with corresponding detents (not shown) to releasably secure staple cartridge (218) in the vertical plane. Because channel (226) receives staple cartridge (218), outer widths (W1, W2, W3) of lower jaw (222) are defined by the surrounding walls of lower jaw (222). In contrast, distal tip (232) of staple cartridge (218) protrudes distally beyond lower jaw (222) and thus defines outer width (W4) of lower jaw (220) in use. However, it will be appreciated that the arrangement between staple cartridge (218) and lower jaw (220) may be varied so that either feature may define the particular dimensions discussed below. As such, other suitable configurations of end effector (212) with widths (W1, W2, W3, W4) will be apparent to persons skilled in the art in view of the teachings herein.

Proximal end portion (270) defines proximal width (W1), which is generally the widest portion of widths (W1, W2, W3, W4), because proximal end portion (270) includes abutments (274, 278) of staple cartridge (218) and lower jaw (222), respectively. From proximal end portion (270), end effector (212) narrows to linear portion (228), which defines linear width (W2). In one example, linear width (W2) is generally constant along centerline (233) throughout linear portion (228). Linear portion (228) extends distally to arcuate portion (230).

Arcuate portion (230) of the present example tapers down continuously from linear portions (228) toward distal tip (232) such that the arcuate width is variable, but does have average arcuate width (W3), as indicated in FIG. 14. Thus, arcuate portion (230) is curved and tapered for improved access within the tissue. While the distal end of the arcuate portion (230) is narrower than distal tip (232) in order to accommodate corresponding abutments (276, 278), distal width (W4) is generally narrower than widths (W1, W2, W3), discussed above. Distal tip (232) extends distally from arcuate portion (228) and is generally rounded such that distal tip (232) may be used for squeezing between and isolating tissues, without necessarily stabbing, cutting, or tearing the tissues in contact with distal tip (232). While many of these above features have been described specifically with respect to lower jaw (216), it will be appreciated that corresponding proximal end portion (270), linear portion (228), arcuate portion (230), and distal tip (232) are also included with upper jaw (212) (see FIG. 13).

3. Exemplary Arcuate Portion and Overlapping Predetermined Staple Pattern of Staple Cartridge As discussed above, end effector (212) includes arcuate portion (230), along which left and right rows of staple pockets (242a, 242b, 242c) extend through deck (238). Exemplary staple cartridge (218) shown in FIG. 13 and FIG. 14 curves to the right, and, as such, the right row of staple pockets (242a) is positioned radially inwardly from centerline (233), whereas the left row of staple pockets (242b) is positioned radially outwardly from centerline (233). In addition, staple pockets (242a) in linear portion (228) and in the right row have a crown dimension (C1) to accommodate staples (244a). Thus, a consistent gap (G1) is maintained between adjacent staple pockets (242a) in the row of the inner curve, for consistent overlap in the transverse direction with staple pockets (242b) in the row of the outer curve.

However, because these staple pockets (242a, 242b) follow the curvature of arcuate portion (230) on each side of centerline (233), the left or outer row of staple pockets (242b) defines an elongated arc relative to the shorter arc, which is defined by the right or inner row of staple pockets (242a). Each staple pocket (242b) and staple (244b) within arcuate portion (230) of the left or outer row is thus elongated with an elongated crown dimension (C2) in order to maintain consistent gap (G1) and overlap with the adjacent staple pockets (242a) and staples (244a). Effectively, a crown (282b) of each elongated staple (242b) is longer than a crown (282a) of each staple (242a) to account for the elongated arc of the left or outer row of staple pockets (242b). Of course, it will be appreciated that other arrangements of staple pockets and associated staples may be used accordingly. For example, one or more staples may be shortened relative to other staples (244a) in linear portion (228) to account for length differences between arcing rows of staple pockets.

Furthermore, while many of these above features have been described specifically with respect to lower jaw (216), it will be appreciated that corresponding linear portion (228) and arcuate portion (230) are also included with upper jaw (212) (see FIG. 11). To this end, anvil (224) (see FIG. 11) also includes staple forming pockets (246a, 246b) (see FIG. 11) that respectively correspond to staple pockets (242a, 242b) and include elongated crown dimension (C2) for forming staples (244b) with elongated crown (282b). Thus, the geometry of upper jaw (212) complements the geometry of lower jaw (216).

4. Exemplary Drivers Along Centerline of Cartridge and Related Methods

FIGS. 15-18 show wedge sled (256) as well as staple row drivers (252) configured to direct staples (244a, 244b, 244c) upwardly toward anvil (224) for forming staples (244a, 244b, 244c). Wedge sled (256) includes spacers (284), projecting from left and right sides thereof, that are configured to center wedge sled (256) in a track slot (286) extending through staple cartridge (218) along centerline (233). Wedge sled (256) includes cam ramp (258) centrally positioned between spacers (284) and projecting upwardly therefrom to align with centerline (244) as wedge sled (256) slides from the proximal sled position to the distal sled position. A rear end portion (288) receives translating member (266), which is configured to translate toward distal tip (232), for directing wedge sled (256) distally toward the distal position. Spacers (284) and track slot (286) are configured such that wedge sled (256) may effectively slide along centerline (233) throughout arcuate portion (230). In addition, translating member (266) is generally flexible in the horizontal plane to similarly follow centerline (233) throughout arcuate portion (230).

A row driver assembly (292) includes a pair of staple row drivers (252) connected by a driver cam (294) extending therebetween. The pair of staple row drivers (252) generally includes a distally positioned staple driver (252) and a proximally positioned staple driver (252) on each lateral side of driver cam (294). Staple drivers (252) for each row driver assembly (292) are generally positioned such that one staple driver (252) overlaps in the transverse direction with the other staple driver (252). As such, each row driver assembly (292) is configured to similarly overlap another proximally positioned row driver assembly (292) and another distally positioned row driver assembly (292). Each staple driver (252) further includes a longitudinal groove (296) configured to cradle crown (282a) of a corresponding one of staples (244a, 244b). It will be appreciated that each staple driver (252) may be unitarily secured to driver cam (294) relative to the other staple driver (252) for row driver assembly (292) to accommodate linear and arcuate portions (228, 230) discussed above in greater detail. As such, one of ordinary skill will appreciate the unique configurations of staple drivers (252) for sliding vertically through the plurality of staple pockets (242a, 242b) aligned with staple forming pockets (246a, 246b) (see FIG. 12) based on the descriptions herein. It will be further appreciated that the term "assembly" as used herein is not intended to be limited to discrete assembled components. Rather the term "assembly" includes components that may be formed separately and assembled and components that may be formed integrally as a single part. Thus, the term "assembly" is not intended to limit the invention described herein.

Figure 19:
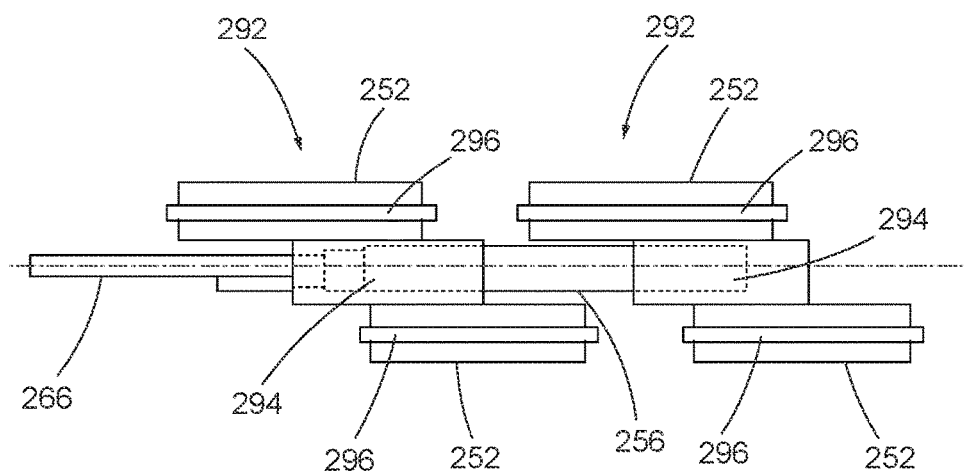
FIG. 19 depicts a top view of a pair of the staple row driver assemblies of FIG. 16 and the wedge sled of FIG. 15.

As shown in FIG. 18, cartridge body (234) defines elongated cam slot (257) that receives both cam ramp (258) of wedge sled (256) and driver cam (294) of row driver assembly (292) for engagement therebetween. Cam slot (257) extends through cartridge body (234) and along centerline (233) such that each of wedge sled (256) and row driver assembly (292) straddle centerline (233) through central portions thereof, as shown in FIG. 19. In some versions, cam ramp (258) lies centrally along centerline (233) such that each of the distal and proximal row staples drivers (252) of row driver assembly (292) are on opposing sides of centerline (233). Thus, leading, intermediate, and trailing cam surfaces (260, 262, 264) successively engage driver cam (294) to direct each staple (244a, 244b) upwardly toward anvil (260) for formation.

Figure 20A:
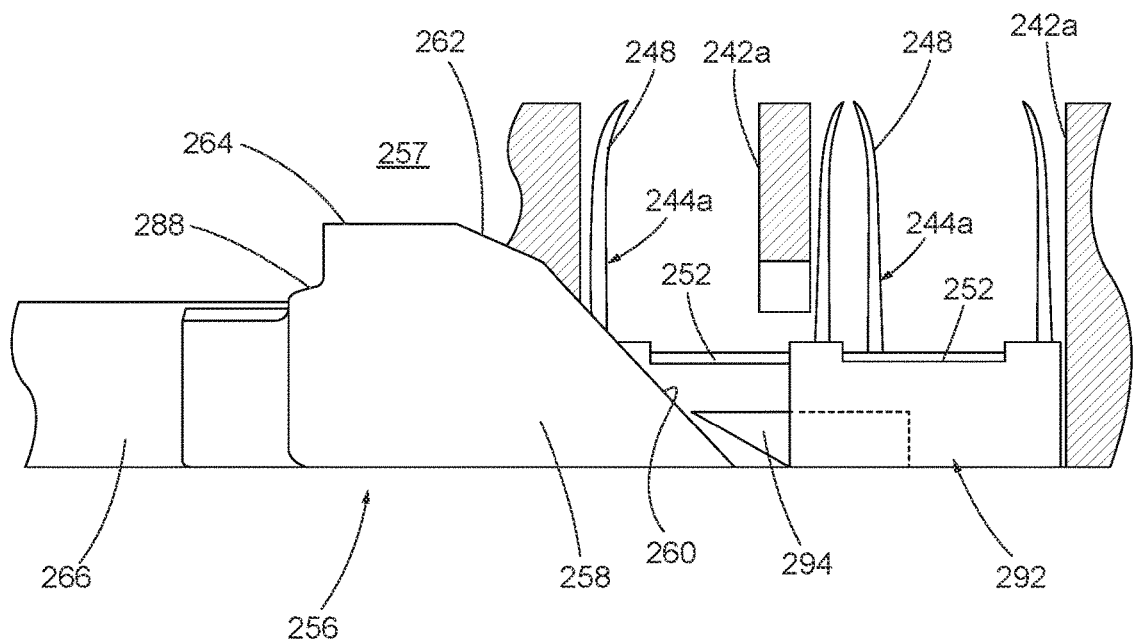
FIG. 20A depicts a side cross-sectional view of the wedge sled of FIG. 15 at a first longitudinal position, sliding toward the staple row driver assembly of FIG. 16, taken generally along a centerline of the lower jaw of FIG. 11.

In use, FIG. 19 shows a top view of a pair of exemplary row driver assemblies (292) overlapped in the transverse direction and straddling centerline (233) to represent approximate positions within the plurality of staple pockets (242a) as shown in FIG. 20A. In order to drive row driver assemblies (292) upwardly toward anvil (224) for forming staples (244a), translating member (266) forces wedge sled (256) distally to engage driver cam (294). Leading cam surface (260) of cam ramp (258) slides under driver cam (294) and lifts driver cam (294) vertically upwardly along the relatively steep angle of leading cam surface (260). Given the relatively steep angle of leading cam surface (260), the vertical movement is relatively large in view of the relatively small distance that wedge sled (256) slid along through cam slot (257).

Figure 20B:
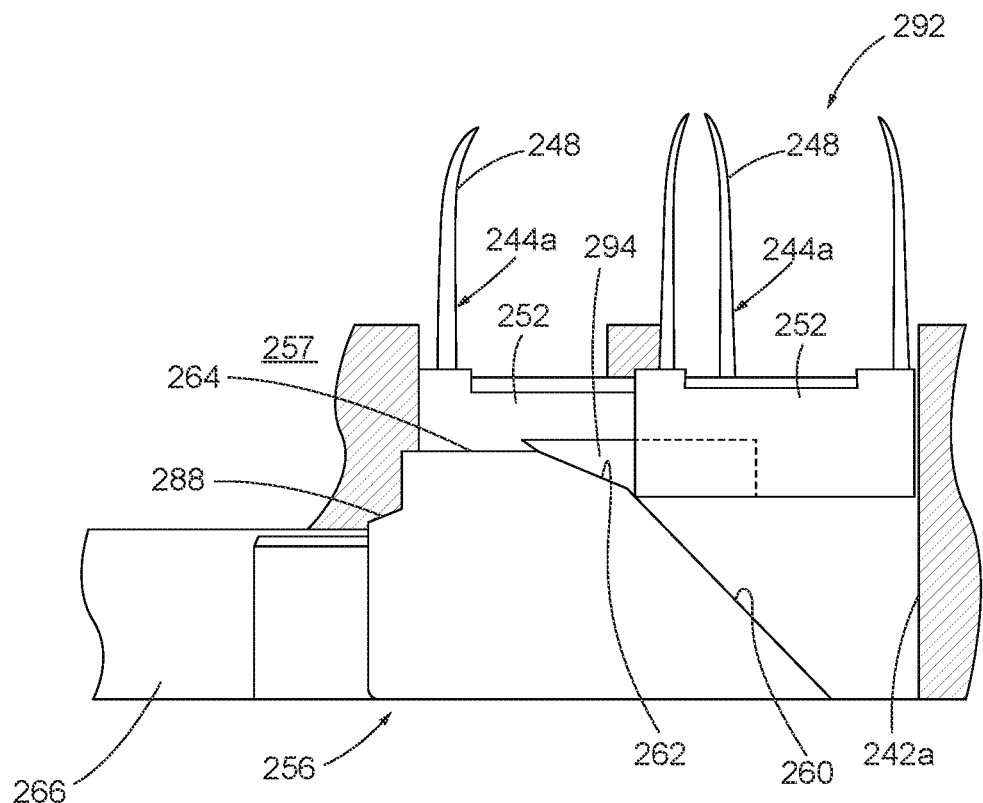
FIG. 20B depicts a side cross-sectional view of the wedge sled of FIG. 15 at a second longitudinal position, directing the staple row driver assembly of FIG. 16 upwardly, taken generally along a centerline of the lower jaw of FIG. 11.

As wedge sled (256) continues to translate distally as shown in FIG. 20B, intermediate cam surface (262) of cam ramp (258) then slides under driver cam (294) and lifts driver cam (294) further vertically upwardly along the relatively gradual angle of intermediate cam surface (260). The relatively gradual angle of intermediate cam surface (262) lifts row driver assembly (292) a relatively small vertical distance in view of the relatively large distance that wedge sled (256) slides through cam slot (257). Thereby, wedge sled (256) is configured to complete the work to form staple (244a) within tissue with less force by taking advantage of the known principle that increasing distance over which a force is applied allows equivalent work to be done with less force.

Figure 20C:
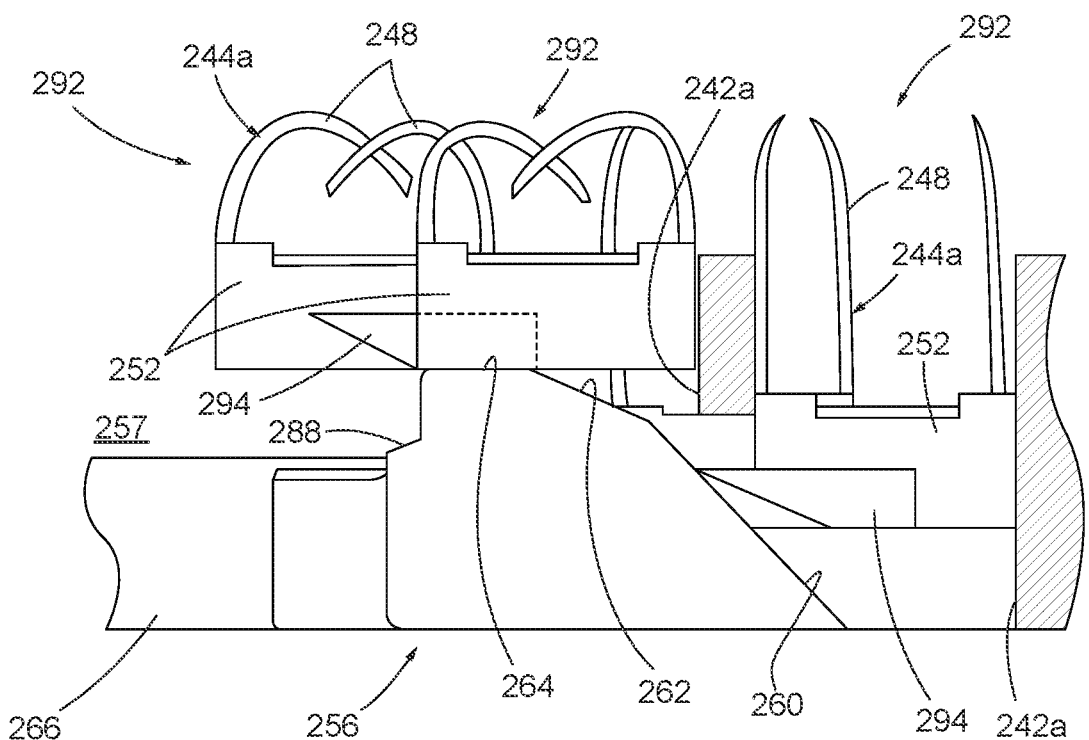
FIG. 20C depicts a side cross-sectional view of the wedge sled of FIG. 15 at a third longitudinal position, with the staple row driver assembly of FIG. 16 in an upper position, taken generally along a centerline of the lower jaw of FIG. 11.

With staples (244a) formed on each side of centerline (233) as shown in FIG. 20C, wedge sled (256) continues to slide distally along centerline (233) such that trailing cam surface (264) provides any further upward force necessary to inhibit staples (244a) and/or staple row drivers (252) from recoiling vertically downwardly. In some versions, trailing cam surface (264) is generally horizontal. Wedge sled (256) continues to slide distally toward the distal position along cam slot (257) to further drive upward movement of staple row driver assemblies (292) throughout linear and arcuate portions (228, 230) of end effector (212).

5. Exemplary Staple Straddling Centerline in Staple Cartridge

Figure 21:
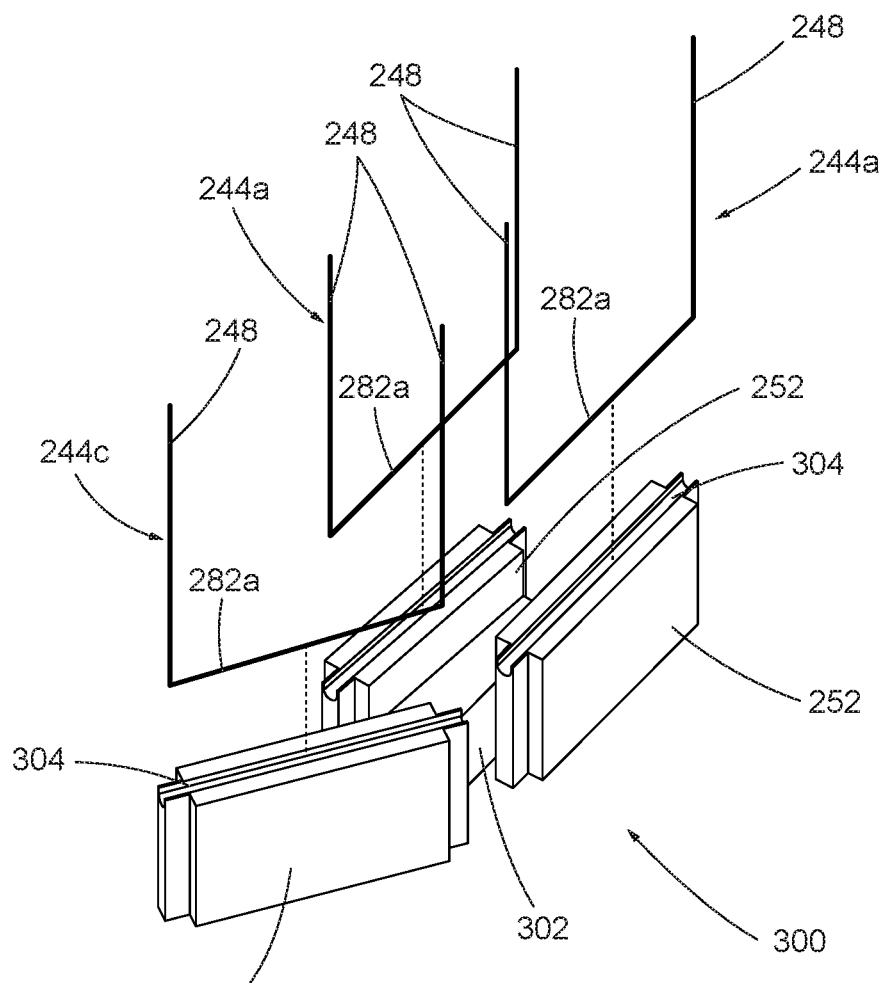
FIG. 21 depicts a perspective view of a cross driver assembly of the lower jaw shown in FIG. 11.
Figure 22:
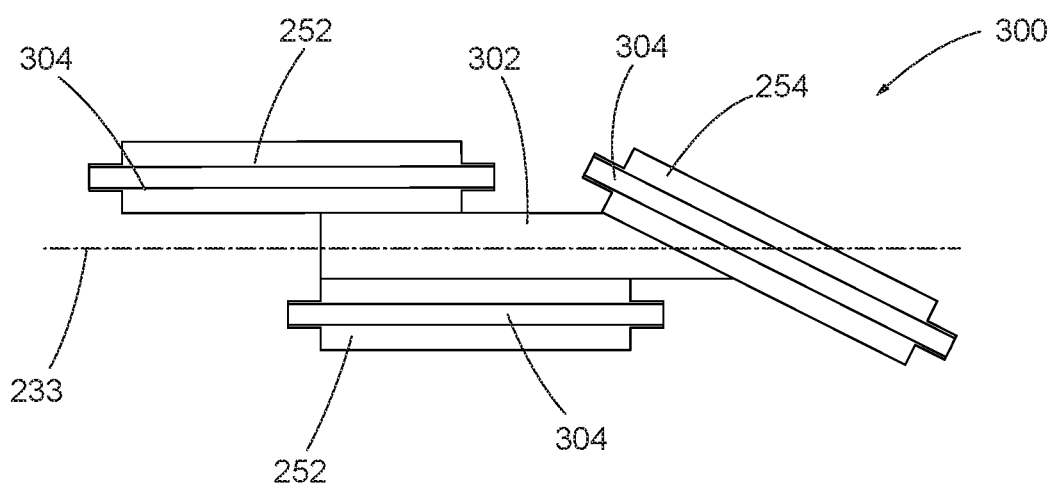
FIG. 22 depicts a top view of the cross driver assembly of FIG. 21.

As shown in FIG. 13 and FIG. 21, as wedge sled (256) approaches the distal position, wedge sled (256) engages a cross driver assembly (300) having a pair of staple row drivers (252) as well as one distally positioned cross staple driver (254). In the present example, staple row drivers (252) may also be referred to as proximal and intermediate staple row drivers (252), and cross staple driver (254) may also be referred to as distal cross staple driver (254) given the relative positions between staple drivers (252, 254), which form cross driver assembly (300). The pair of staple row drivers (252) and cross staple driver (254) are connected by a driver cam (302) extending therebetween. The pair of staple row drivers (252) generally includes a distally positioned staple driver (252) and a proximally positioned staple driver (252) on each lateral side of driver cam (302). Staple row drivers (252) for cross driver assembly (300) are generally positioned such that one staple driver (252) overlaps in the transverse direction with the other staple driver (252). As such, cross driver assembly (300) is configured to similarly overlap a proximally positioned staple row drivers (252).

Cross staple driver (254) extends distally beyond staple row drivers (252) on cross driver assembly (300) and is obliquely angled relative to centerline (233) such that cross staple driver (254) itself straddles centerline (233) proximate to distal tip (232) of end effector (212). More particularly, cross staple driver (254) has ends that are positioned near staple row drivers (252) to maintain consistent gaps (G1) for effective ligation such that staple (244c) is configured to staple tissue across centerline (233). To this end, each staple driver (252, 254) further includes a longitudinal groove (304) that is configured to cradle a corresponding crown (282a) of staples (244b, 244c). It will be appreciated that the term "assembly" as used herein is not intended to be limited to discrete assembled components. Rather the term "assembly" includes components that may be formed separately and assembled and components that may be formed integrally as a single part. Thus, the term "assembly" is not intended to limit the invention described herein. It will be further appreciated that cross staple driver (254) is tilted relative to centerline (233) to accommodate the curvature of arcuate portion (230) and that alternative curvature of any directions may be similarly accommodated. Thus, the invention described herein is not intended to be limited to the tilted direction of cross staple driver (254).

6. Exemplary Shortened Distal End of Staple Cartridge

Figure 23A:
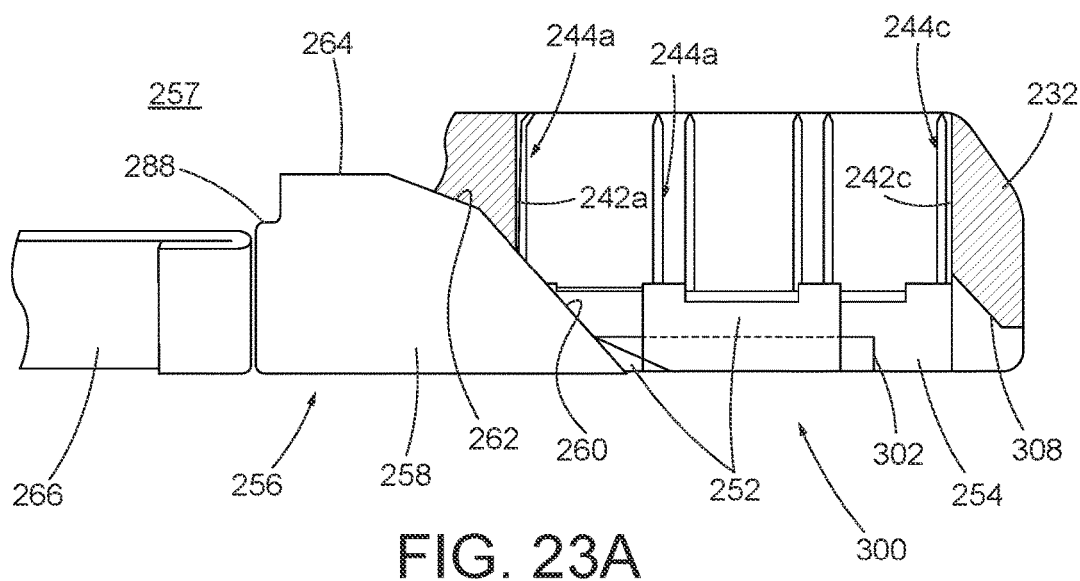
FIG. 23A depicts a side cross-sectional view of the wedge sled of FIG. 15 at a first longitudinal position, sliding toward the cross driver assembly of FIG. 21, taken generally along a centerline of the lower jaw of FIG. 11.

In order to drive cross driver assembly (300) upwardly toward anvil (224) for forming staples (244a, 244b, 244c), translating member (266) forces wedge sled (256) distally to engage driver cam (302) as shown in FIG. 23A. It should be understood that wedge sled (256) will reach the position shown in FIG. 23A after wedge sled (256) has driven all of the row driver assemblies (292) to an upper position. As wedge sled (256) translates distally from the position shown in FIG. 23A, leading cam surface (260) of cam ramp (258) slides under driver cam (302) and lifts driver cam (302) vertically upwardly along the relatively steep angle of leading cam surface (260). Given the relatively steep angle of leading cam surface (260), the vertical movement is relatively large in view of the relatively small distance that wedge sled (256) slid along through cam slot (257).

Figure 23B:
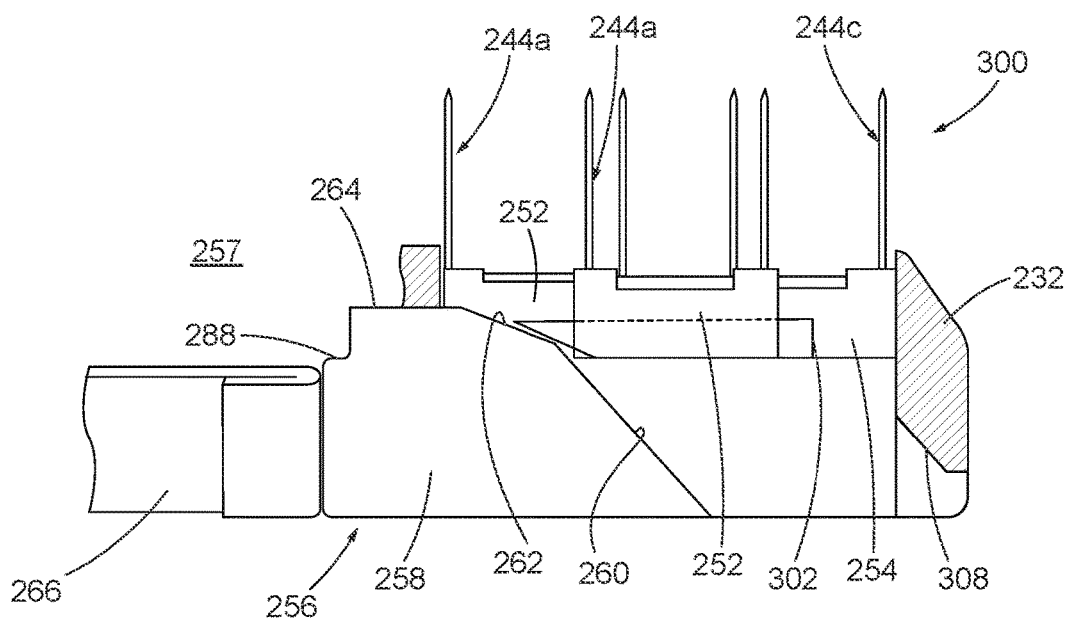
FIG. 23B depicts a side cross-sectional view of the wedge sled of FIG. 15 at a second longitudinal position, directing the cross driver assembly of FIG. 21 upwardly, taken generally along a centerline of the lower jaw of FIG. 11.

As wedge sled (256) continues to translate distally as shown in FIG. 23B, intermediate cam surface (262) of cam ramp (258) then slides under driver cam (302) and lifts driver cam (302) further vertically upwardly along the relatively gradual angle of intermediate cam surface (260). The relatively gradual angle of intermediate cam surface (262) lifts row driver assembly (292) a relatively small vertical distance in view of the relatively large distance that wedge sled (256) slides through cam slot (257). Thereby, wedge sled (256) is configured to complete the work to form staples (244a, 244b, 244c) within tissue with less force by taking advantage of the known principle that increasing distance over which a force is applied allows equivalent work to be done with less force. In addition, the multiple leading and intermediate cam surfaces (260, 262) allow for cam ramp (258) of wedge sled (256) to have a shortened length along centerline (233), because leading cam surface (260) quickly urges cross driver assembly (300) upwardly, while intermediate cam surface (262) proves a sufficient vertical force to form staples (244a, 244b, 244c), as discussed above.

Figure 23C:
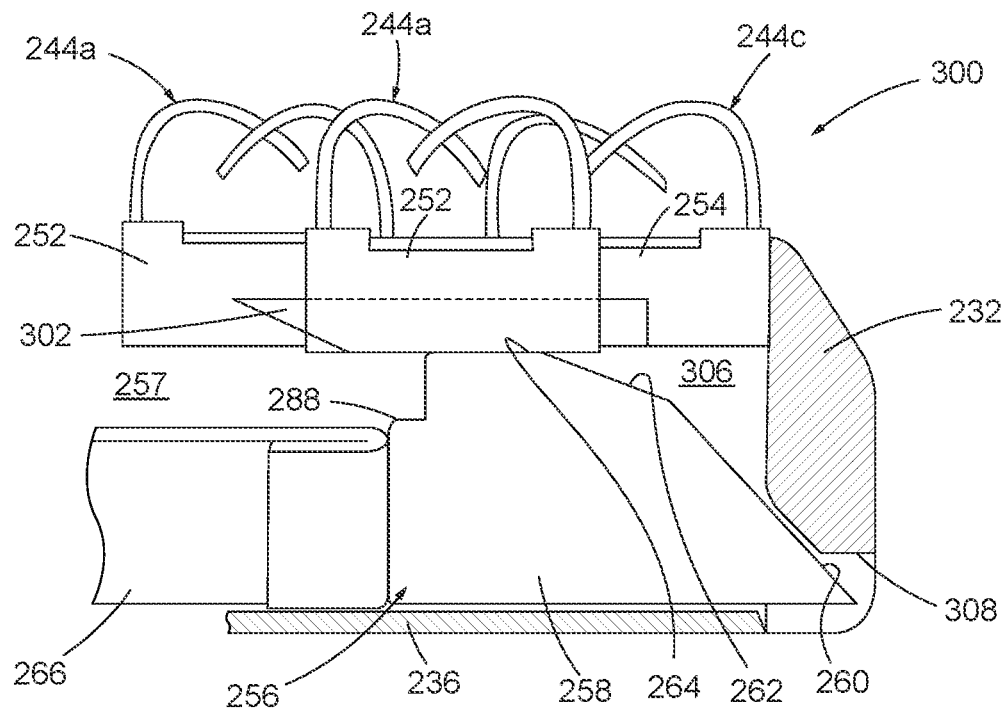
FIG. 23C depicts a side cross-sectional view of the wedge sled of FIG. 15 at a third longitudinal position, with the cross driver assembly of FIG. 21 in an upper position, taken generally along a centerline of the lower jaw of FIG. 11.
Figure 24:
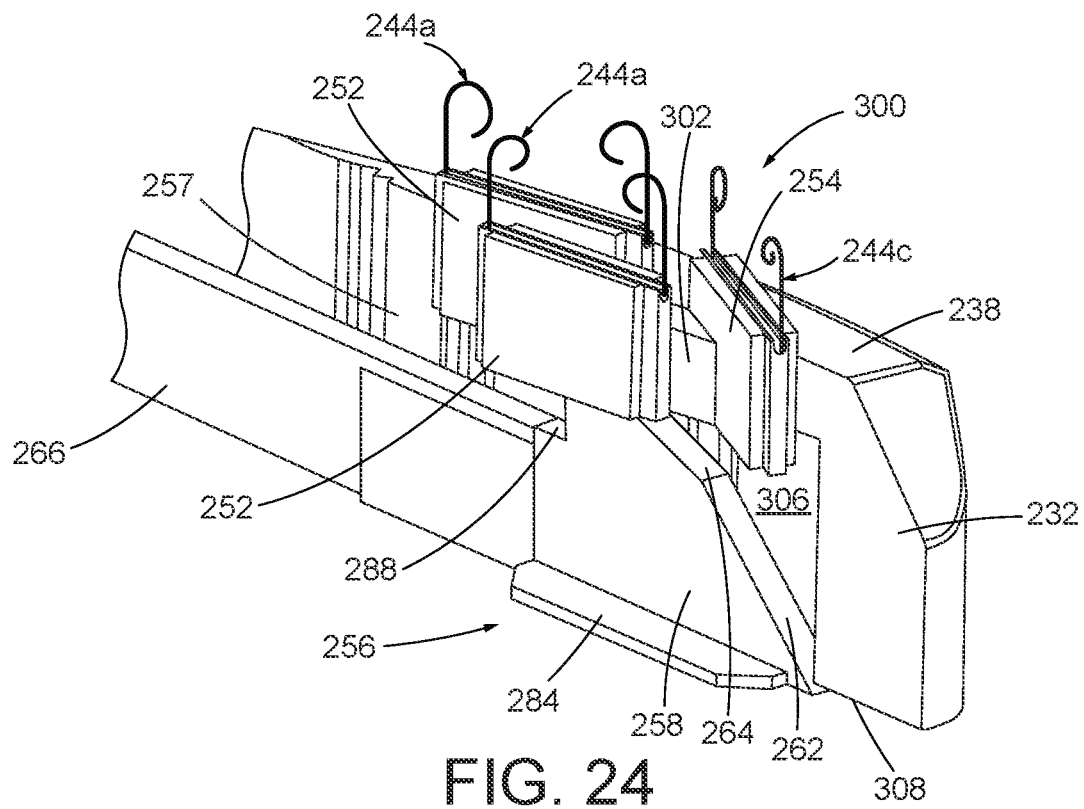
FIG. 24 depicts a perspective cross-sectional view of the lower jaw of FIG. 11, with the wedge sled of FIG. 15 at the third longitudinal position, and with the cross driver assembly of FIG. 21 in the upper position.

With staples (244a, 244b) formed on each side of centerline (233) and staple (244c) straddling centerline (233) as shown in FIG. 23C and FIG. 24, wedge sled (256) continues to slide distally along centerline (233) such that trailing cam surface (264) provides any further upward force necessary to inhibit staples (244a, 244b, 244c) and/or row and cross staple drivers (252, 254) from recoiling vertically downwardly. In some versions, trailing cam surface (264) is generally horizontal.

Wedge sled (256) continues to slide distally until its translational movement along centerline (233) is blocked by distal tip (232) of staple cartridge (218). As such, wedge sled (256) effectively parks underneath cross staple driver (254), which in conjunction with tray (236) defines a storage space (306) for wedge sled (256) therebetween. In other words, distal tip (232) inhibits distal movement of wedge sled (256) such that a majority of wedge sled (256) cannot slide distally beyond cross staple driver (254). Furthermore, a distal portion of cam ramp (258) of wedge sled (256) is received within a lower aperture (308) of distal tip (232) that further defines storage space (306) such that only a minor distal portion of wedge sled (256) slides distally beyond cross staple driver (254), as shown in FIG. 23C and FIG. 24. Moreover, cam surfaces (260, 262, 264) do not fully traverse the length of crown (282a) of the distal-most staple (244c).

Cross driver assembly (300), wedge sled (256), and distal tip (232) are thus collectively configured to reduce elongation of distal tip (232) of end effector (212) for improved access to tissue within patients. First, cross staple driver (254) is cantilevered distally beyond driver cam (302) to increase the distal most position of staple (244c), while providing additional storage space (306) defined underneath. Second, wedge sled (256) includes multiple leading and intermediate cam surfaces (260, 262) to result in the shortened length of cam ramp (258). Third, lower aperture (308) within distal tip (232) provides for final translation along centerline (233) without further distal elongation of distal tip (232). Thereby, cross driver assembly (300), wedge sled (256), and distal tip (232) are each configured in part to reduce travel of wedge sled (256) and reduced elongation of distal tip (232) of end effector (212) for improved access. In addition, the very close longitudinal positioning of the distal-most staple pocket (242) to distal tip (232) will minimize the occurrence of tissue being severed by crush surfaces (214, 216) at regions that are distal to the distal-most staple (244c).

7. Exemplary Method of Tissue Resection

FIGS. 25A-25F show one example of using end effector (212) to resect tissue, such as a liver parenchyma tissue (310), and to ligate a vessel or duct (316) therein. As noted above, vessel or duct (316) may comprise a hepatic vein or a hepatic artery. It should also be understood that the method may further include the use of end effector (212) to ligate other vessels such as the portal vein and extrahepatic vessels, etc.

Figure 25A:
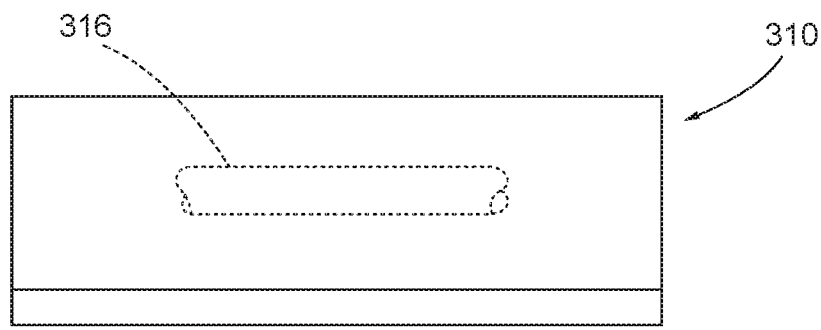
FIG. 25A depicts a schematic representation of a liver having a vessel extending through the liver tissue.
Figure 25B:
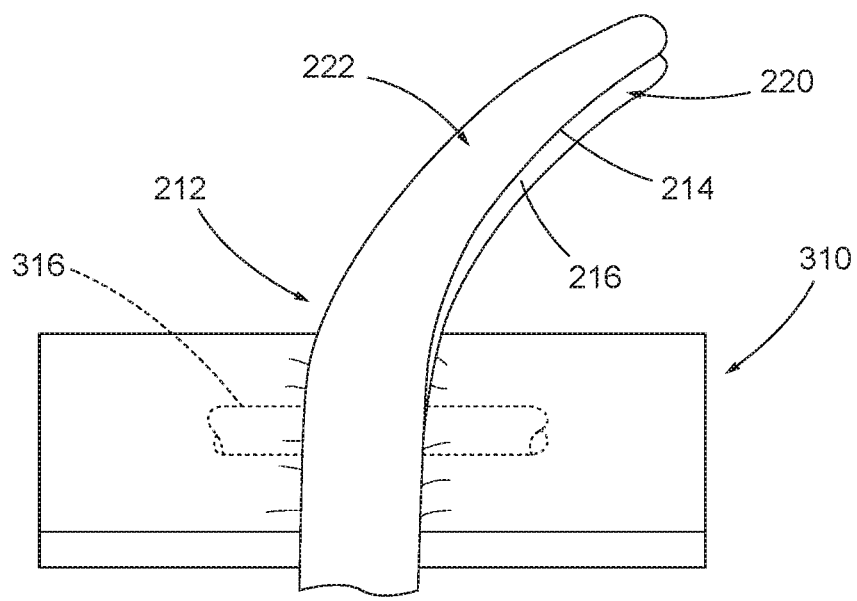
FIG. 25B depicts the schematic representation of the end effector of FIG. 10 severing the liver tissue of FIG. 25A.

As shown in FIG. 25B, the operator positions end effector (212) such that tissue (310), including vessel or duct (316), is located between lower and upper jaws (220, 222). The operator then compresses tissue (310) between upper and lower crush surfaces (214, 216) of upper and lower jaws (220, 222), respectively, to deliver the predetermined crush pressure to tissue (310). By way of example only, jaws (220, 222) may be actuated in this manner by pivoting trigger (24) toward pistol grip (22). It should be understood that jaws (220, 222) need not necessarily be actuated to a fully closed configuration. In some instances, the operator may rely on tactile feedback through trigger (24) and pistol grip (22) to determine whether the operator has achieved a desired gap between jaws (220, 222) to suitably crush tissue (310) without undesirably damaging vessel or duct (316). In addition or in the alternative, the operator may rely on visual feedback.

Figure 25C:
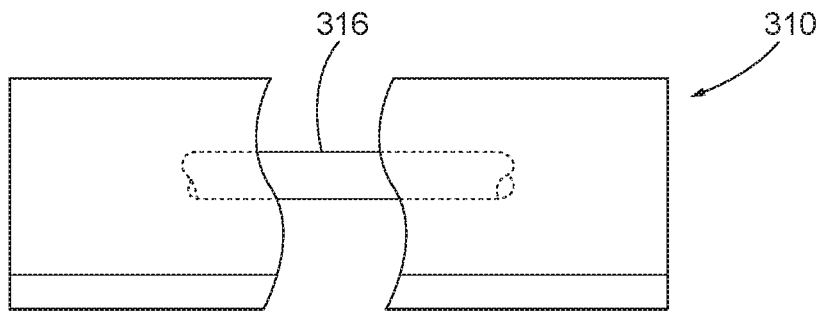
FIG. 25C depicts the schematic representation of the vessel of FIG. 25B exposed from the severed liver tissue of FIG. 25A.

In any case, the crush pressure applied by jaws (220, 222) effectively severs tissue (310), and the operator then removes end effector (212) from tissue (310) to view whether or not any vessels or ducts (316) are present. As shown in FIG. 25C, vessel or duct (316) remains intact and is left exposed, extending between severed portions of tissue (310).

Figure 25D:
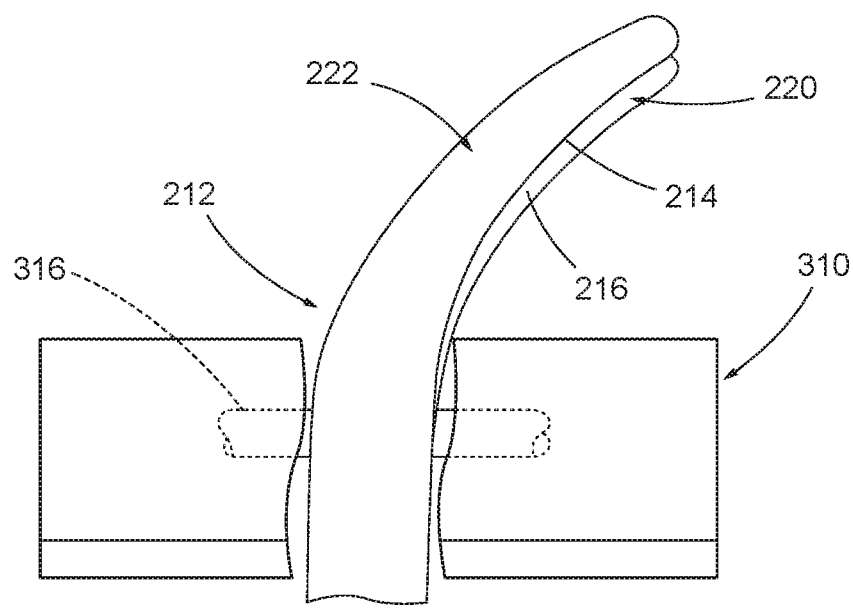
FIG. 25D depicts the schematic representation of the end effector of FIG. 10 stapling the exposed vessel of FIG. 25C.
Figure 25E:
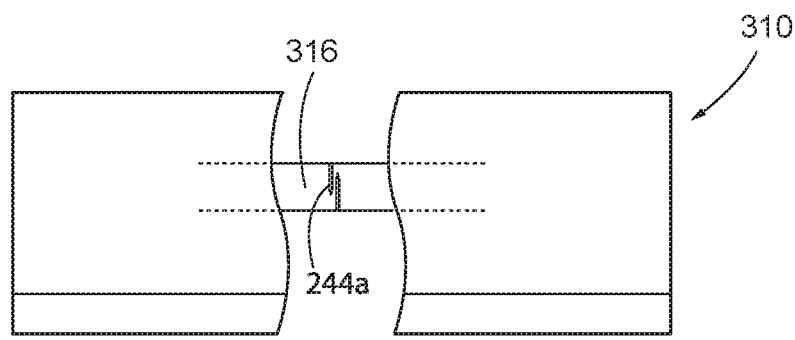
FIG. 25E depicts the schematic representation of the vessel of FIG. 25D exposed and stapled.
Figure 25F:
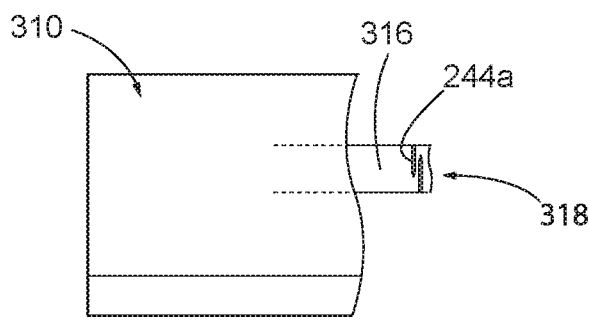
FIG. 25F depicts the schematic representation of the liver of FIG. 25A having a portion of the liver tissue and the vessel resected therefrom.
Figure 26:
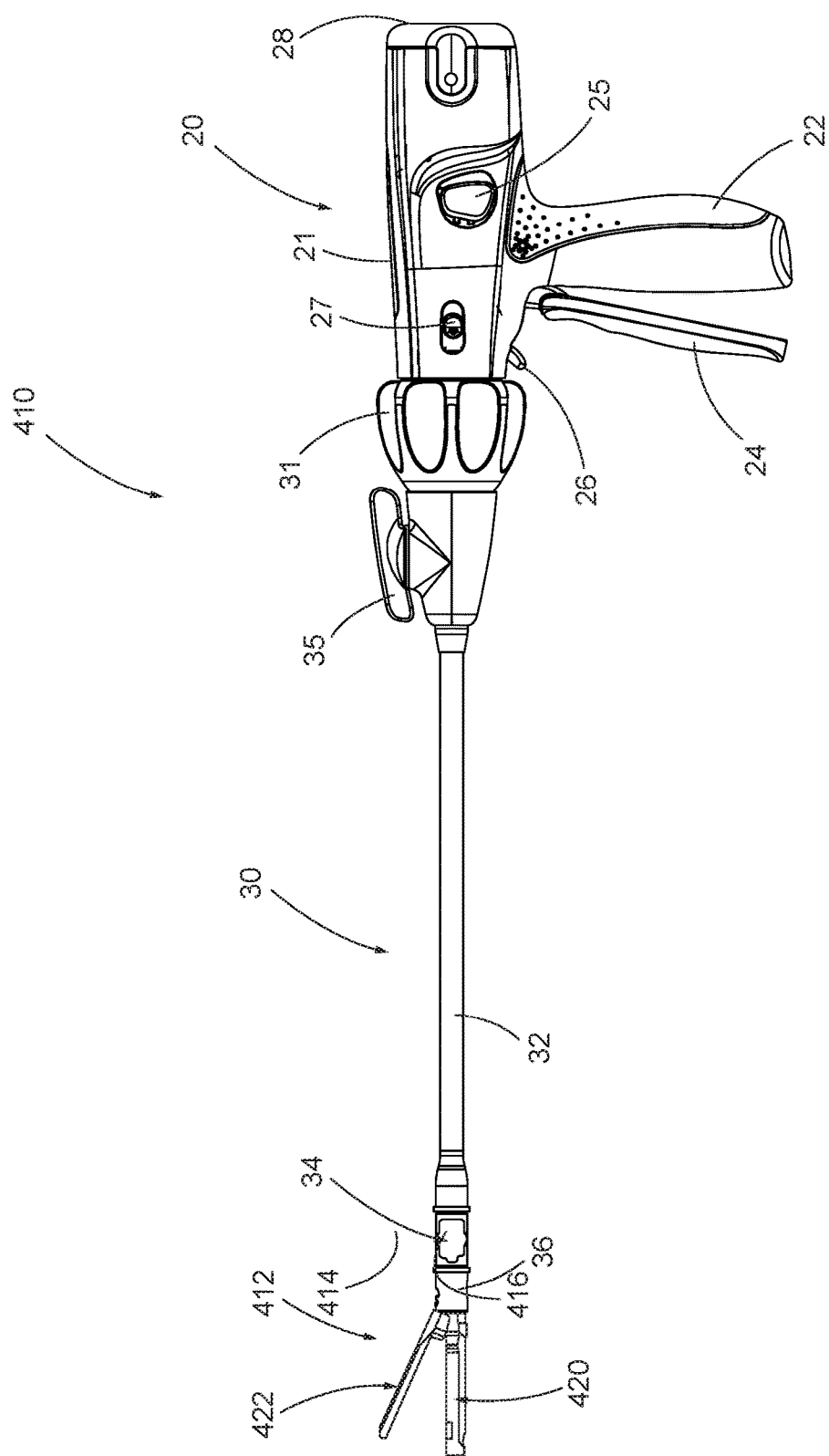
FIG. 26 depicts a side elevational view of still another exemplary articulating surgical stapling instrument.

In some instances, the operator may leave vessel or duct (316) intact. However, in the present example, the operator ligates vessel or duct (316) to complete the resection of a severed portion of tissue (310), as shown in FIG. 25D and FIG. 25E. Ligation includes placement of at least some of overlapping staples (244a, 244b, 244c) within vessel or duct (316) as discussed above in greater detail. It should therefore be understood that the same end effector (212) may be used to crush (and thereby sever) tissue (310) of the liver and also ligate a vessel or duct (316) in the tissue (310). In the present example, after ligation of vessel or duct (316), the operator removes end effector (212) from liver tissue (310) and severs vessel or duct (316) with another surgical instrument (not shown) known in the art for cutting tissue, such as a conventional blade or shears, etc. Thereby, the operator completes resection of a right portion of tissue (310) and the corresponding portion of the vessel or duct (316), as shown in FIG. 25F. The applied staples (244a) seal the severed end (318) of the vessel or duct (316).

As described above, the operator removes end effector (212) for viewing vessel (316) as shown in FIG. 25C. Alternatively, the operator may apply the predetermined crush pressure (or as determined based on tactile and/or visual feedback as noted above), as shown in FIG. 25B, and immediately thereafter ligate any tissue remaining therein, such as vessel or duct (316). As such, it is not necessary to view such tissue, but the operator may find such viewing desirable in one or more liver resection procedures. It will be appreciated that the above described resection is merely illustrative and not limited to liver tissue. Alternatively, tissue resection with end effector (212) may be performed on other tissues within the patient as desired by the user.

B. Exemplary Stapling Instrument with Shortened Straight End Effector

FIGS. 26-30 show surgical instrument (410) with end effector (412) having upper crush surface (414), lower crush surface (416), staple cartridge (418), and knife member (419). As noted above, it may be desirable to provide such a surgical instrument (410) with an end effector (412) having crush surfaces (414, 416) that are configured to sever tissue by crushing the tissue; while also providing adjacent staple cartridge (418) to selectively ligate one or more vessels passing through the tissue. In addition, knife member (419) is configured to cut the one or more vessels for complete removal of the surrounding tissue. Thereby, surgical instrument (410) will allow the operator to more quickly assess the tissue and proceed with further tissue severing and/or tissue ligation. Surgical instrument (410) of the present example also includes handle assembly (20) and shaft assembly (30) discussed above in greater detail. Except as otherwise described below, end effector (412), in conjunction with handle assembly (20) and shaft assembly (30), is configured and operable similar to end effector (40) (see FIG. 1). By way of example only, end effector (412) may have a length of approximately 40 mm and a width of approximately 7 mm. Alternatively, any other suitable dimension may be used.

End effector (412) of the present example includes a lower jaw (420) and an upper jaw (422), which forms an anvil (424). Upper jaw (422) is pivotally mounted relative to lower jaw (420) for receiving the tissue therebetween. More particularly, anvil (424) is pivotable toward and away from lower jaw (420) between an open position and a closed position (e.g., in response to pivotal movement of trigger (24) toward and away from pistol grip (22)). For instance, in the present example, anvil (424) pivots about an axis that is defined by pins (not shown), which slide along curved slots (not shown) of lower jaw (420) as anvil (424) moves toward lower jaw (420). In such versions, the pivot axis translates along the path defined by slots (not shown) while anvil (424) simultaneously pivots about that axis. In addition or in the alternative, the pivot axis may slide along slots (not shown) first, with anvil (424) then pivoting about the pivot axis after the pivot axis slides a certain distance along the slots (not shown). Alternatively, some versions may provide pivotal movement of anvil (424) about an axis that remains fixed and does not translate within a slot or channel, etc.

Figure 28:
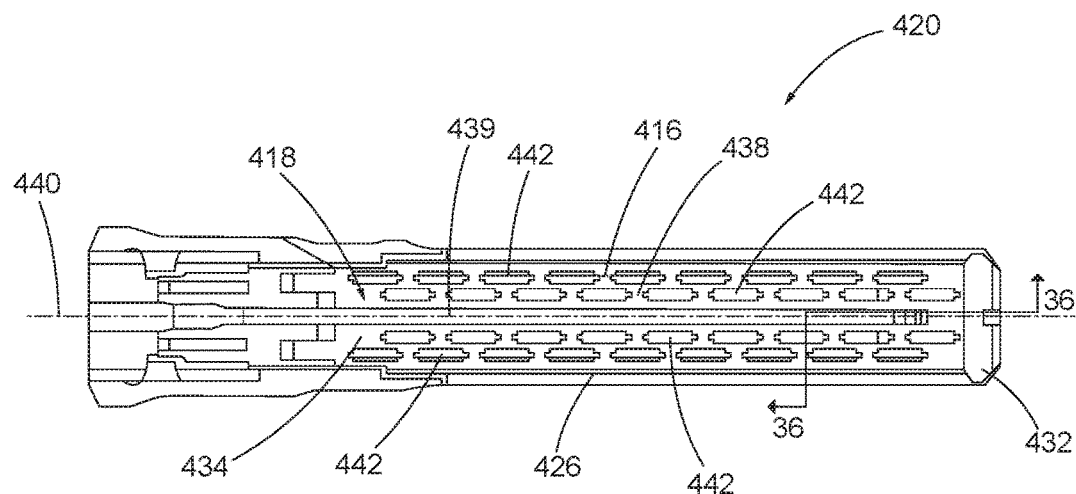
FIG. 28 depicts a top view of a lower jaw of the end effector of FIG. 27.
Figure 29:
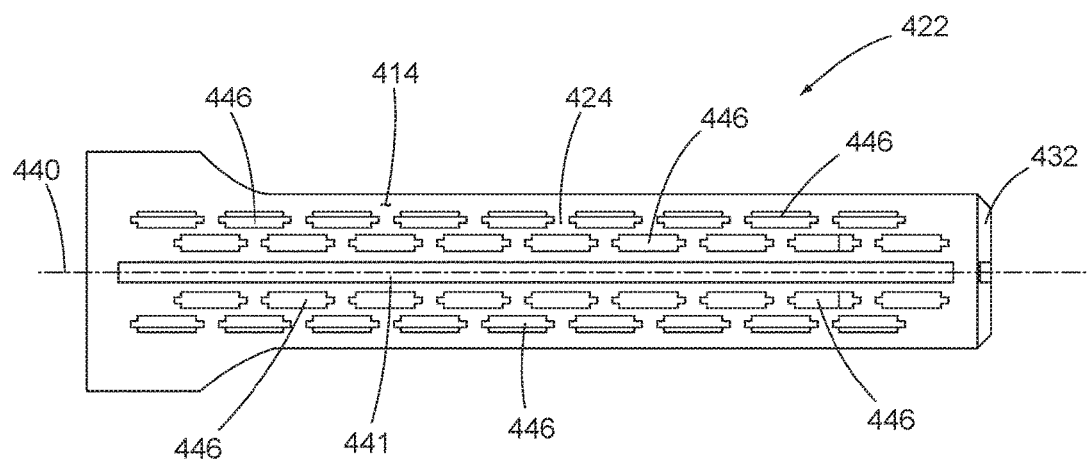
FIG. 29 depicts a bottom view an upper jaw of the end effector of FIG. 27.
Figure 30:
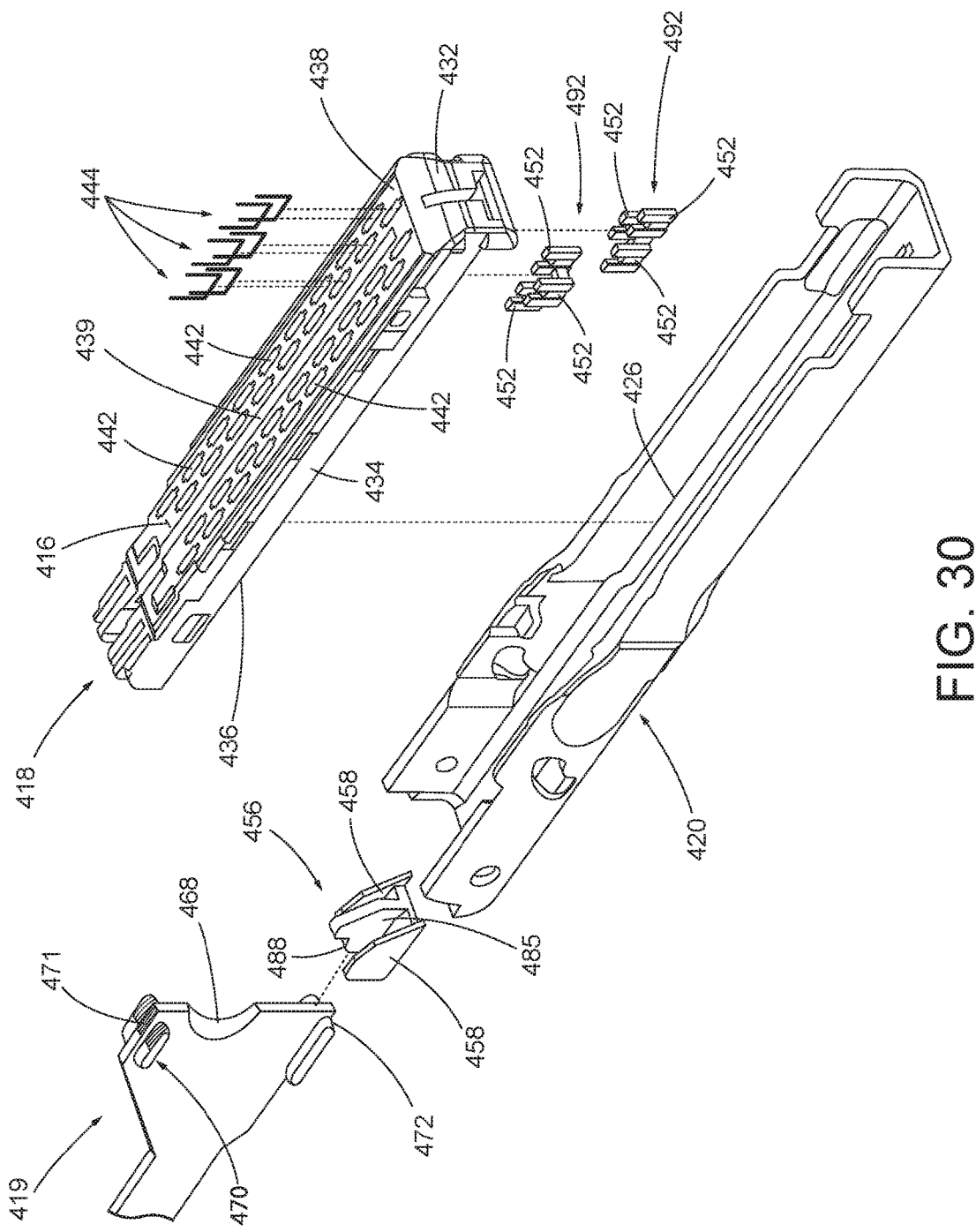
FIG. 30 depicts an exploded perspective view of the lower jaw of FIG. 27.

As best seen in FIGS. 28-30, lower jaw (420) of the present example defines a channel (426) that is configured to receive staple cartridge (418). Staple cartridge (418) may be inserted into channel (426), end effector (412) may be actuated, and then staple cartridge (418) may be removed and replaced with another staple cartridge (418). Lower jaw (420) thus releasably retains staple cartridge (418) in alignment with anvil (424) for actuation of end effector (412). In some alternative versions, the components of staple cartridge (418) are fully integrated into lower jaw (420) such that end effector (412) may only be used once. Other suitable forms that lower jaw (420) may take will be apparent to those of ordinary skill in the art in view of the teachings herein. In the present example, lower and upper jaws (420, 422) extend to a distal tip (432), which is further defined by staple cartridge (418).

Staple cartridge (418) of the present example comprises a cartridge body (434) and a tray (436) (see FIG. 36) secured to an underside of cartridge body (434). An upper side of cartridge body (434) presents a deck (438), against which tissue may be compressed when anvil (424) is in a closed position. In the present example, lower crush surface (416) is positioned along staple cartridge (418). However, it will be appreciated that lower crush surface (416), as well as cooperating upper crush surface (414) may be alternatively positioned along end effector (412) for severing tissue via compression.

Cartridge body (434) further defines an elongated channel (439) extending through lower jaw (420) and linearly along a centerline (440) of end effector (412). Another elongated channel (441) defined by anvil (424) extends through upper jaw (422) and linearly along centerline (440), as well, for reasons discussed below in greater detail. A plurality of staple pockets (442) follow a predetermined pattern along deck (438) on opposing sides of centerline (440). More particularly, staple cartridge (418) includes two longitudinally extending rows of staple pockets (442) on one side of centerline (440); and another set of two longitudinally extending rows of staple pockets (442) on the other side of centerline (440). However, in some other versions, staple cartridge (418) may include three, one, or some other number of staple pockets (442) on each side of centerline (440).

One of a plurality of staples (444) is positioned in respective staple pockets (442). Adjacent rows of staple pockets (442) are configured to overlap in a direction transverse to the centerline (440) in order to install the plurality of staples (444) within the tissue and inhibit openings therebetween for improved ligation. In other words, a consistent gap (G1) is maintained between adjacent staple pockets (442) for consistent overlap in the present example. As used herein, the term "overlap" is intended to include one feature overlapping with another in at least one direction. Thus, a feature may be offset from another feature and still overlap as described herein in the event that these features overlap in at least one plane, such as a transverse plane including the transverse direction. Other suitable forms that staple cartridge (418) may take will be apparent to those of ordinary skill in the art in view of the teachings herein.

With respect to FIGS. 28-30, anvil (424) of the present example has a plurality of staple forming pockets (446). Each staple forming pocket (446) is positioned to lie over a corresponding staple pocket (442) of staple cartridge (418) when anvil (424) is in a closed position. Staple forming pockets (446) are configured to deform each leg (448) of staples (444) when staples (444) are driven through tissue and into anvil (424). In particular, staple forming pockets (446) are configured to bend legs (448) of staples (444) to secure the formed staples (444) in the tissue. Other suitable forms that anvil (424) may take will be apparent to those of ordinary skill in the art in view of the teachings herein.

Figure 36:
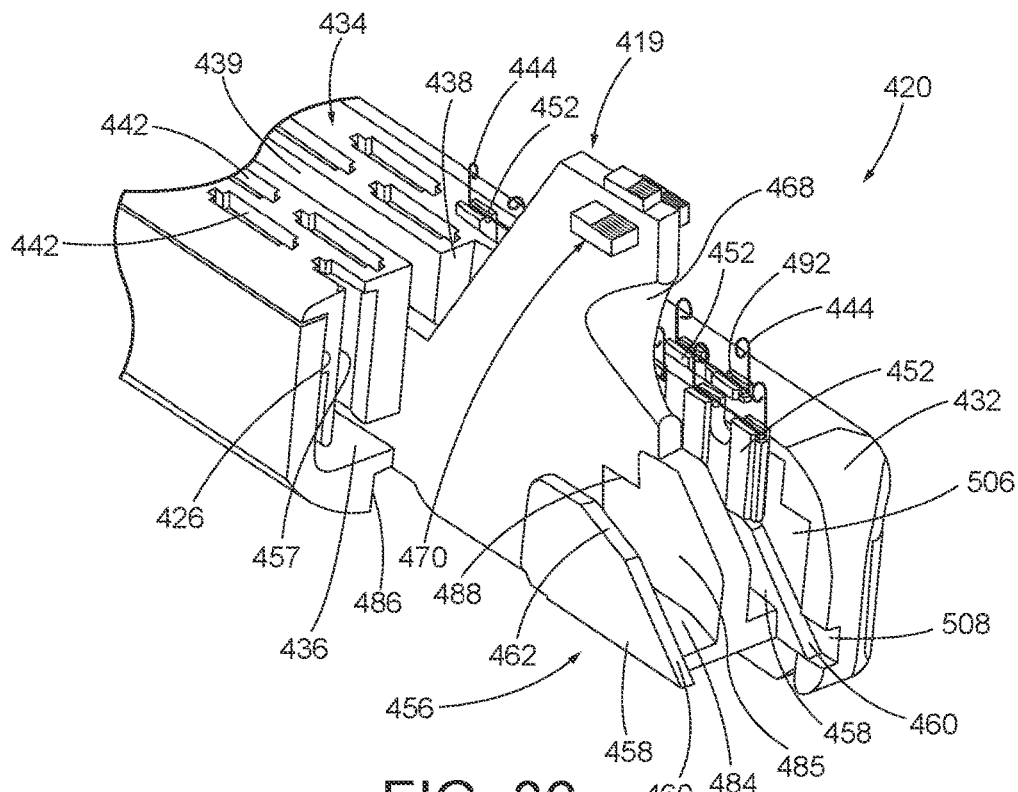
FIG. 36 depicts a perspective view of the lower jaw of FIG. 30, in partial cross-section taken along section line 36-36 of FIG. 28.

As best seen in FIG. 30, staple cartridge (418) includes staple drivers (452) positioned in staple pockets (442), underneath a corresponding staple (444), and above tray (436) (see FIG. 36). As will be described in greater detail below, staple drivers (452) are operable to translate upwardly in staple pockets (442) to thereby drive staples (444) upwardly through staple pockets (442) and into engagement with anvil (424). Staple drivers (452) are driven upwardly by a wedge sled (456), which is captured between cartridge body (434) and tray (436) (see FIG. 36), and which translates longitudinally through cartridge body (434) along a pair of cam slots (457). Wedge sled (456) includes a cam ramp (258) having a leading cam surface (460), an intermediate cam surface (462), and a trailing cam surface (464). By way of example only, leading cam surface (460) may be angled at approximately 45° relative to a horizontal plane; and intermediate cam surface (462) may be angled at approximately 22° relative to a horizontal plane. Alternatively, any other suitable angles may be used. Cam ramps (458) are generally configured to engage staple drivers (452) and thereby drive staple drivers (452) upwardly as wedge sled (456) translates longitudinally through staple cartridge (418) from a proximal sled position to a distal sled position. For instance, when wedge sled (456) is in the proximal sled position, staple drivers (452) are in downward positions and staples (444) are located in staple pockets (442). As wedge sled (456) is driven to the distal sled position by translating knife member (419), wedge sled (456) drives staple drivers (452) upwardly, thereby driving staples (444) out of staple pockets (442) and into staple forming pockets (446). Thus, staple drivers (452) translate along respective vertical planes as wedge sled (456) translates along a horizontal plane.

In the present example, knife member (419) is configured to translate through end effector (412). As best seen in FIG. 30, knife member (419) is secured to a distal end of firing beam (82), which extends through a portion of shaft assembly (30). Knife member (80) is positioned in channels (439, 441) of staple cartridge (418) and anvil (424), respectively. Knife member (419) includes a distally presented cutting edge (468) that is configured to sever tissue that is compressed between anvil (424) and deck (438) of staple cartridge (418) as knife member (419) translates distally through end effector (412). As noted above, knife member (419) also drives wedge sled (456) distally as knife member (419) translates distally through end effector (412), thereby driving staples (444) through tissue and against anvil (424) into formation.

1. Exemplary Triple Driver Assembly of Staple Cartridge

FIGS. 30-33 show wedge sled (456) and staple drivers (452), which are configured to direct staples (444) upwardly toward anvil (424) for forming staples (444) as described herein. Wedge sled (456) includes spacers (484) projecting from left and right sides of a central portion (485) thereof to a pair of left and right cam ramps (458). Spacers (484) are configured to center wedge sled (456) in a track slot (486) (see FIG. 36) extending through staple cartridge (418) along centerline (440). Each cam ramp (458) projects upwardly from each respective spacer (484) to align each cam ramp (458) centrally within parallel linear cam slots (457) as wedge sled (456) slides from the proximal sled position to the distal sled position. A rear end portion (488) receives translating knife member (419), which is configured to translate toward distal tip (432), for directing the wedge sled (456) distally toward the distal position.

A driver assembly (492) includes three staple drivers (452) connected by a driver cam (494) extending therebetween. As such, driver assembly (492) may also be referred to as triple driver assembly (492) Two of the three staple drivers (452) generally include a distally positioned staple driver (452) and a proximally positioned staple driver (452) on a common lateral side of driver cam (494) such that these staple drivers (452) are generally longitudinally aligned. These staple drivers (452) may also be referred to below more specifically as distal and proximal staple drivers (452). In addition, the third staple driver (452) may be referred to as intermediate staple driver (452) and overlaps between distal and proximal drivers (452) on an opposing side of driver cam (494).

Figure 34:
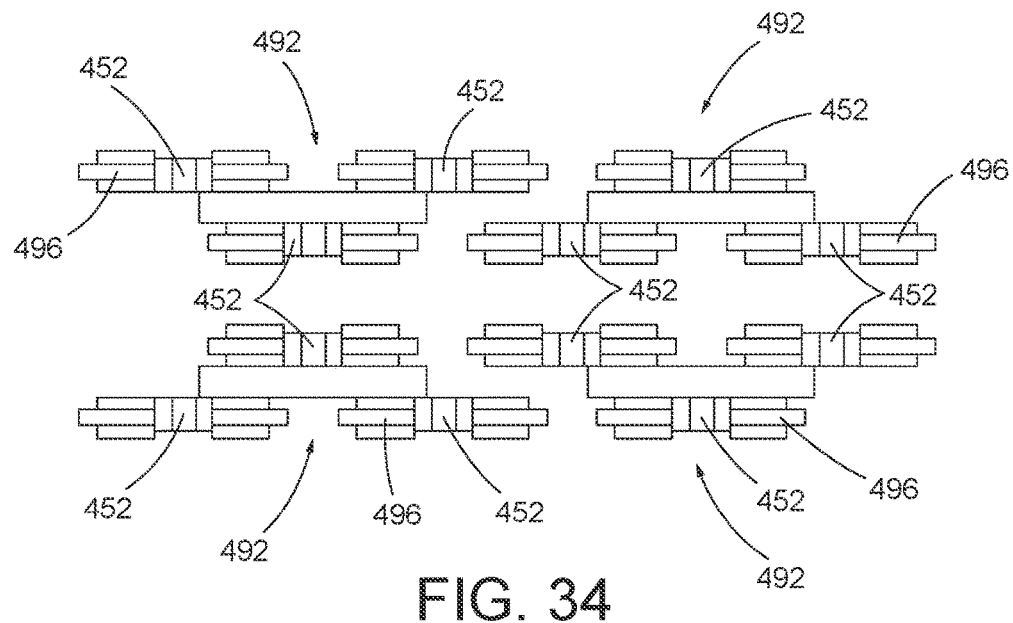
FIG. 34 depicts a top view of an arrangement triple driver assemblies of the lower jaw of FIG. 27.

Each of the distal, intermediate, and proximal staple drivers (452) are in parallel with each other. In addition, each triple driver assembly (452) is configured to similarly overlap with another proximally positioned triple driver assembly (492) and another distally positioned triple driver assembly (492), as seen in FIG. 34. In other words, triple driver assemblies (492) are arranged in an alternative fashion in each row, such that one triple driver assembly (492) provides a single staple driver (452) on a first side of the row and two staple drivers (452) on a second side of the row; then the next triple driver assembly (492) provides a pair of staple drivers (452) on the first side of the row and a single staple driver (452) on the second side of the row; and so on. Triple driver assemblies (452) are thus aligned in alternating, asymmetric orientations in each row.

Each staple driver (452) further includes a longitudinal groove (496) that is configured to cradle the crown of a corresponding one of staples (444). It will be appreciated that each staple driver (452) may be secured to driver cam (494) relative to the other staple drivers (452) for triple driver assembly (492) to accommodate linear or arcuate portions of a variety of end effectors, such as end effector (212) (see FIG. 10) discussed above in greater detail. As such, one of ordinary skill will appreciate the unique configurations of staple drivers (452) for sliding vertically through the plurality of staple pockets (442) aligned with staple forming pockets (446) (see FIG. 29) based on the descriptions herein. It will be further appreciated that the term "assembly" as used herein is not intended to be limited to discrete assembled components. Rather the term "assembly" includes components that may be formed separately and assembled and components that may be formed integrally as a single part. Thus, the term "assembly" is not intended to limit the invention described herein.

Figure 35A:
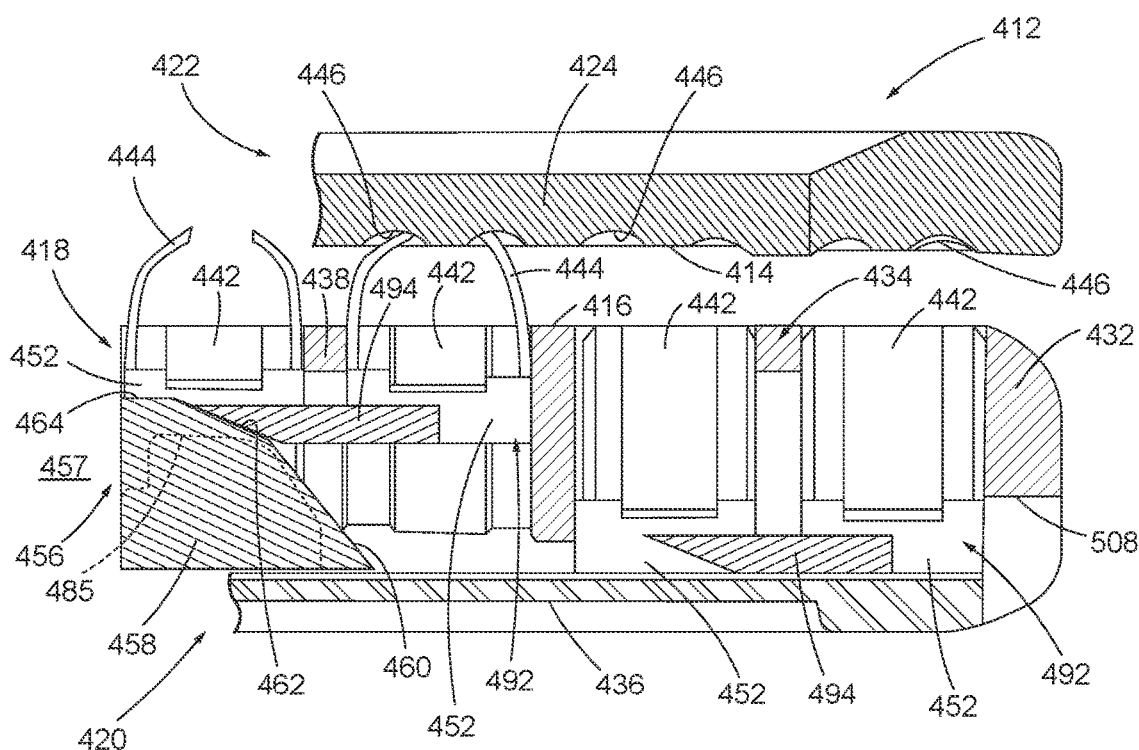
FIG. 35A depicts a side cross-sectional view of the wedge sled of FIG. 31 at a first longitudinal position, sliding toward the triple driver assemblies of FIG. 34, taken generally along a centerline of the lower jaw of FIG. 30.

As shown in FIGS. 35A-36, cartridge body (434) defines elongated cam slots (457) that receive both cam ramp (458) of wedge sled (456) and driver cams (494) of each triple driver assembly (492) for engagement therebetween. Cam slots (457) extend through cartridge body (434) on opposing sides of centerline (440) such that wedge sled (456) straddles centerline (440) through central portion (485) and triple driver assemblies (492) are on each side of centerline (440). However, cam ramps (458) and driver cams (494) lie centrally along respective cam slots (457) such that each of the leading, intermediate, and trailing cam surfaces (460, 462, 464) successively engage driver cams (494) to direct each staple (444) upwardly toward anvil (460) for formation.

While various arrangements of staple drivers (452) are contemplated herein, triple driver assembly (492) of the present example has proximal, intermediate, and distal staple drivers (452) positioned such that distal staple driver (452) is cantilevered distally from driver cam (492). More particularly, this cantilever arrangement of distal driver cam (492) increases the distal most position of staple (444) cradled therein to effectively elongate triple driver assembly (492) to provide additional space for wedge sled (456). As such, staples pockets (442) and staples (444) may be positioned more closely to distal tip (432).

In use, FIG. 34 shows a top view of two pairs of exemplary triple driver assemblies (492) overlapped in the transverse direction and on opposing sides of centerline (430) to represent approximate positions within the plurality of staple pockets (442) as shown in FIG. 35A. In order to drive triple driver assemblies (492) upwardly toward anvil (424) for forming staples (444), translating knife member (419) forces wedge sled (456) distally to engage driver cam (494). Leading cam surface (460) of cam ramp (458) slides under driver cam (494) and lifts driver cam (494) vertically upwardly along the relatively steep angle of leading cam surface (460). Given the relatively steep angle of leading cam surface (460), the vertical movement is relatively large in view of the relatively small distance that cam ramps (458) slid along through cam slots (457).

As knife member (419) drives wedge sled (456) further distally, intermediate cam surfaces (462) of cam ramps (458) then slide under driver cams (494) and lift driver cams (494) further vertically upwardly along the relatively gradual angle of intermediate cam surface (460). The relatively gradual angle of intermediate cam surface (462) lifts triple driver assemblies (492) a relatively small vertical distance in view of the relatively large distance that cam ramps (458) slide through cam slots (457). Thereby, wedge sled (456) is configured to complete the work to form staple (444) within tissue with less force by taking advantage of the known principle that increasing distance over which a force is applied allows equivalent work to be done with less force.

Figure 35B:
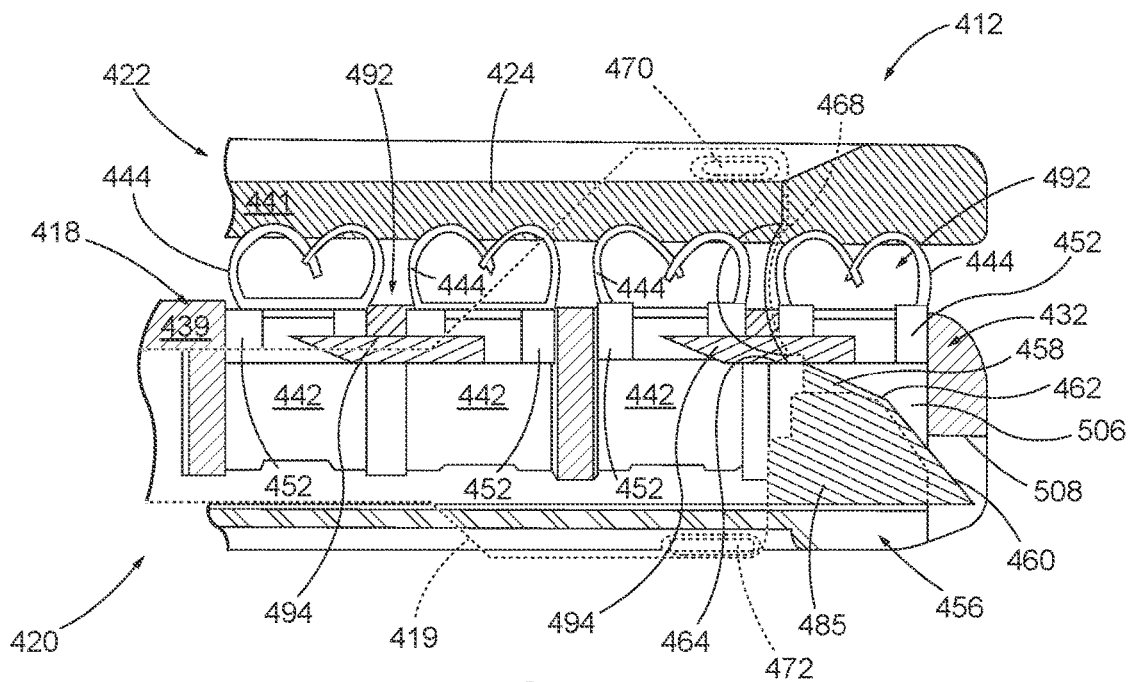
FIG. 35B depicts a side cross-sectional view of the wedge sled of FIG. 31 at a second longitudinal position, with the triple driver assemblies of FIG. 34 in an upper position, taken generally along a centerline of the lower jaw of FIG. 30.

With the staples (444) formed on each side of centerline (440) as shown in FIG. 35B, translating knife member (419) cuts tissue while simultaneously directing wedge sled (456) to continue to slide distally along centerline (440) such that trailing cam surfaces (464) provide any further upward force necessary to inhibit staples (444) and/or staple drivers (452) from recoiling vertically downwardly. In some versions, trailing cam surface (464) is generally horizontal. Wedge sled (456) continues to slide distally toward the distal position along track slot (486) and cam slots (457) to further drive upward movement of triple staple driver assemblies (492) throughout the remaining length of end effector (412).

2. Exemplary Shortened Distal End of Staple Cartridge

As shown in FIG. 35B and FIG. 36, wedge sled (456) slides distally until its translational movement along centerline (440) is blocked by distal tip (432) of staple cartridge (418). As such, wedge sled (456) effectively parks underneath terminal staple drivers (452), which in conjunction with tray (436) define a storage space (506) for wedge sled (456) therebetween. In other words, distal tip (432) inhibits distal movement of wedge sled (456) such that a majority of wedge sled (456) cannot slide distally beyond terminal staple drivers (452). Furthermore, a distal portion of cam ramps (458) of wedge sled (456) are received within a pair of lower apertures (508) of distal tip (432) that further defines storage space (506), such that only a minor distal portion of wedge sled (456) slides distally beyond staple drivers (452), as shown in FIG. 35B and FIG. 36. Moreover, cam surfaces (460, 462, 464) do not fully traverse the length of the crown of the distal-most staple (444).

Triple driver assembly (492), wedge sled (456), and distal tip (432) are thus collectively configured to reduce elongation of distal tip (432) of end effector (412) for improved access to tissue within patients. First, distal staple driver (452) is cantilevered distally beyond driver cam (494) to increase the distal most position of staple (444), while providing additional storage space (506) defined underneath. Second, wedge sled (456) includes multiple leading and intermediate cam surfaces (460, 462) to result in the shortened length of cam ramp (458). Third, lower apertures (508) within distal tip (432) provide for final translation along centerline (440) without further distal elongation of distal tip (432). Thereby, triple driver assembly (492), wedge sled (456), and distal tip (432) are each configured in part to reduce travel of wedge sled (456) and reduce elongation of distal tip (432) of end effector (412) for improved access. In addition, the very close longitudinal positioning of the distal-most staple pockets (446) to distal tip (432) will minimize the occurrence of tissue being severed by crush surfaces (414, 416) at regions that are distal to the distal-most staple (444).

3. Exemplary Upper and Lower Staple Usage Indicia of End Effector

Figure 37:
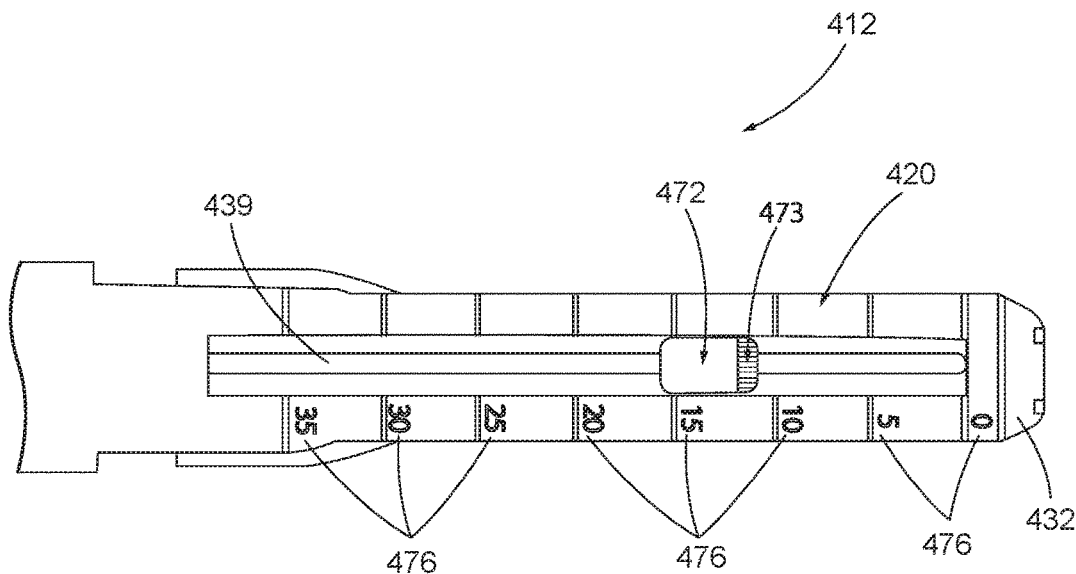
FIG. 37 depicts a bottom view of the end effector of FIG. 27.
Figure 38:
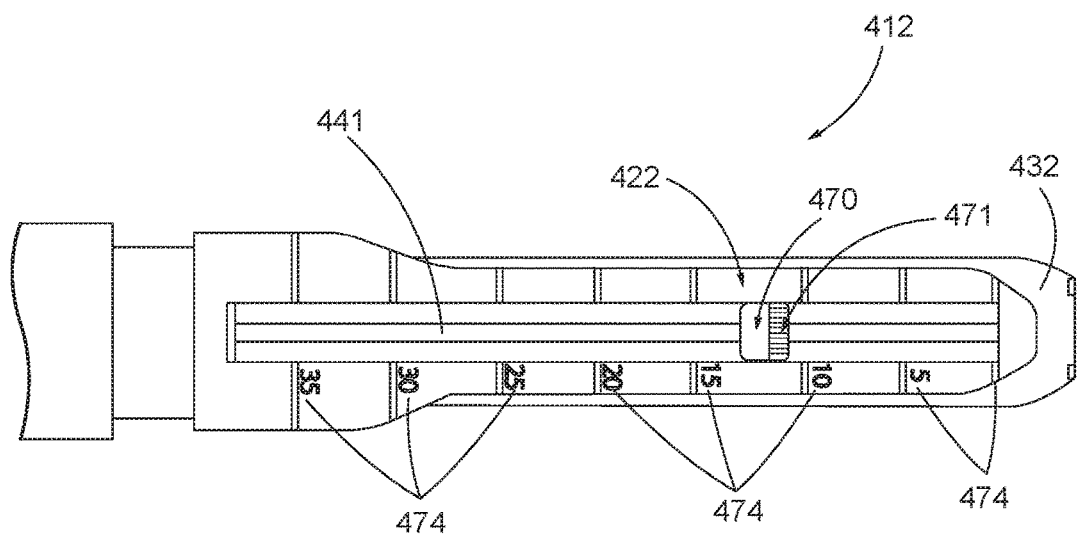
FIG. 38 depicts a top view of the end effector of FIG. 27.

As shown in FIG. 30 and FIGS. 37-38, lower and upper jaws (420, 422) have elongated channels (439, 441) extending through anvil (424) and staple cartridge (434), respectively. As discussed herein in greater detail, elongated channel (439) receives translating knife member (419) that is configured to push wedge sled (456) from the proximal position to the distal position for selectively forming staples (444) in the tissue of the patient. In addition, knife member (419) includes an upper flange (470) and a lower flange (472) that respectively project from channels (441, 439). Flanges (470, 472) extend transversely from the vertical plane defined by knife member (419). Upper flange (470) is configured to bear downwardly on the top side of upper jaw (422) as knife member (419) translates through end effector (412); and lower flange (472) is configured to bear upwardly on the bottom side of lower jaw (420) as knife member (419) translates through end effector (412). Flanges (470, 472) may thus cooperate to enhance compression that is already being applied by jaws (420, 422) as knife member (419) translates through end effector (412).

Knife member (419) further includes markings (471, 473) that are on and/or near flanges (470, 472). Markings (471, 473) are positioned such that markings (471) may be readily viewed by the user. Markings (471, 473) are configured to provide the operator with a visual indication of the longitudinal position of cutting edge (468), which may further indicate the location of the cut line in tissue. In some versions, the longitudinal position of cutting edge (468) is proximal to the longitudinal position of the distal edges of flanges (470, 472). Markings (471, 473) may thus provide the operator with enhanced visual feedback that is more useful than the visual feedback that would otherwise be provided through observation of the distal edges of flanges (470, 472) during translation of knife member (419). It should also be understood that markings (471, 473) may enable immediate visualization of the location of knife member (419) within end effector (412) from either the top or bottom view during use.

Figure 27:
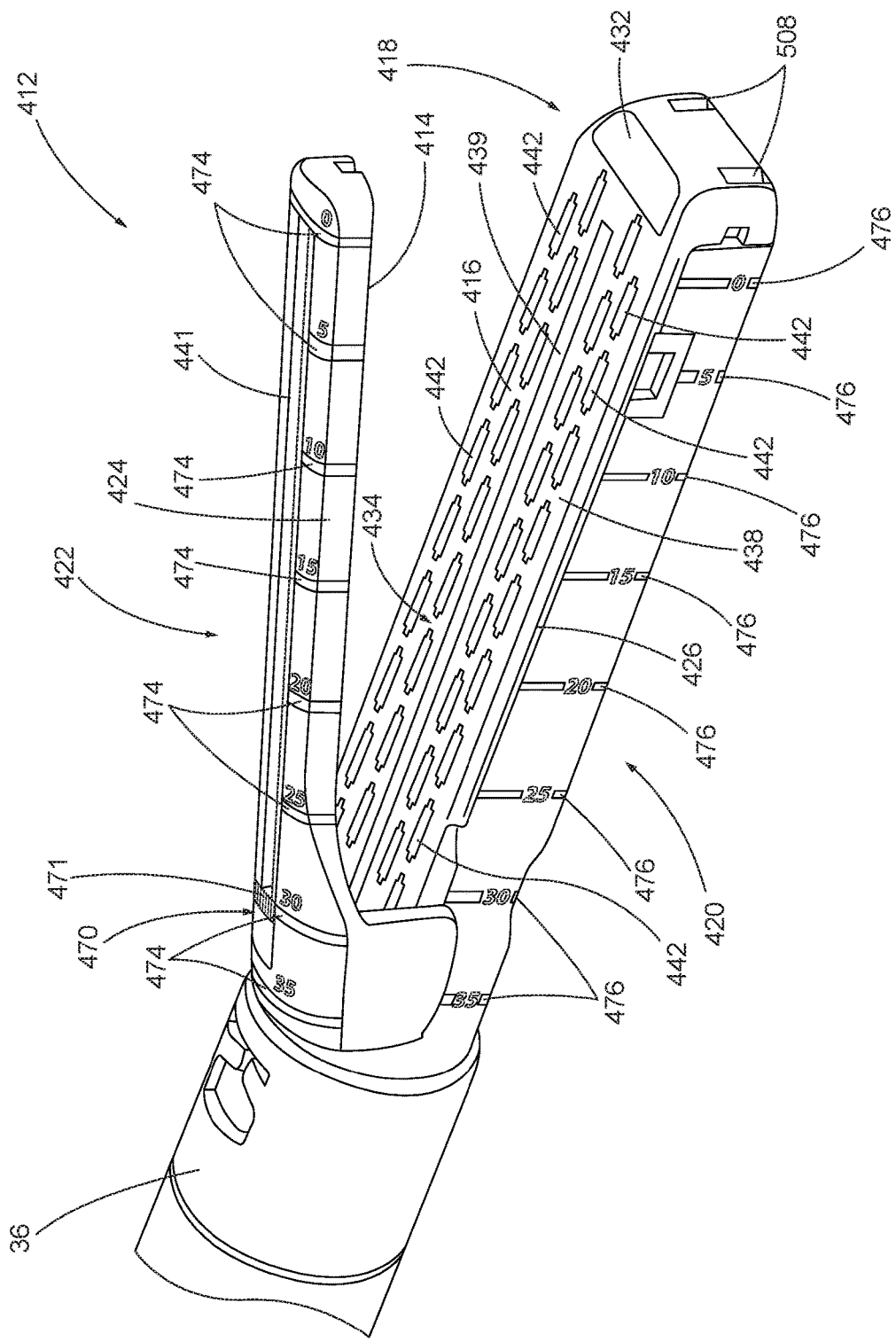
FIG. 27 depicts a perspective view of an end effector of the instrument of FIG. 26, with the end effector in an open configuration.

Furthermore, upper and lower jaws (422, 420) also include a plurality of upper indicia (474) and a plurality of lower indicia (476), respectively. As shown in FIGS. 27 and 38, upper indicia (474) are visible from the top of end effector (412) and from the sides of end effector (412). As shown in FIGS. 27 and 37, lower indicia (476) are visible from the bottom of end effector (412) and from the sides of end effector (412). Each upper indicia (474) is more particularly configured to indicate a remaining amount of staples (444) positioned distally from each respective upper indicia (474). Similarly, each lower indicia (476) is configured to indicate the remaining amount of staples (444) positioned distally from each respective lower indicia (476). In other words, the upper and lower indicia (474, 476) each provide usage indicia of staples (444). Thereby, upper and/or lower indicia (474, 476) in combination with markings (471, 473) are configured to indicate to the operator the remaining amount of staples (444) within staple cartridge (418) in real time during use. The operator may thus view the upper and lower usage indicia (474, 476) more effectively from the top or bottom views and, in turn, more effectively use remaining staples (444) during tissue resection.

In some versions, upper and lower usage indicia (474, 476) includes a countdown of remaining staples that extends distally, from "35" staples (444) at the proximal end to "0" staples at distal tip (432), in increments of five. Alternatively, any other suitable indicia configured to indicate usage may be so used. It will be appreciated that upper and lower usage indicia (474, 476) may also comprise an accumulation of used staples (444), such that upper and lower usage indicia (474, 476) indicate the number of staples (444) used rather than the number of staples (444) remaining in staple cartridge (418). As such, the term "usage indicia" is intended to be used broadly, rather than limit the invention to a particular countdown or accumulation of staples (444).

4. Exemplary Method of Tissue Resection

FIGS. 39A-39E show one example of using end effector (412) to resect tissue, such as a liver parenchyma tissue (310), and to ligate a vessel or duct (316) therein. As noted above, vessel or duct (316) may comprise a hepatic vein or a hepatic artery. It should also be understood that the method may further include the use of end effector (412) to ligate other vessels such as the portal vein and extrahepatic vessels, etc.

Figure 39A:
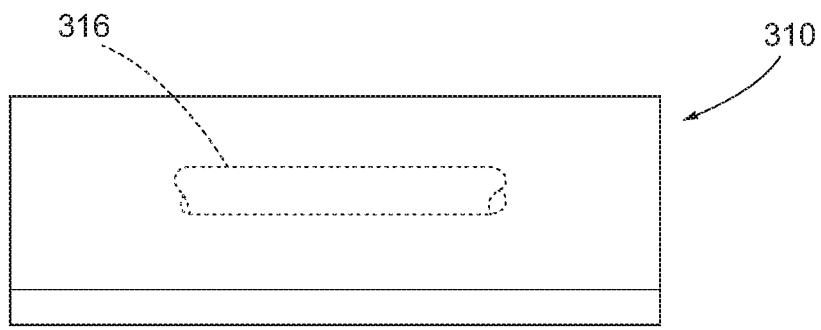
FIG. 39A depicts a schematic representation of a liver having a vessel extending through the liver tissue.
Figure 39B:
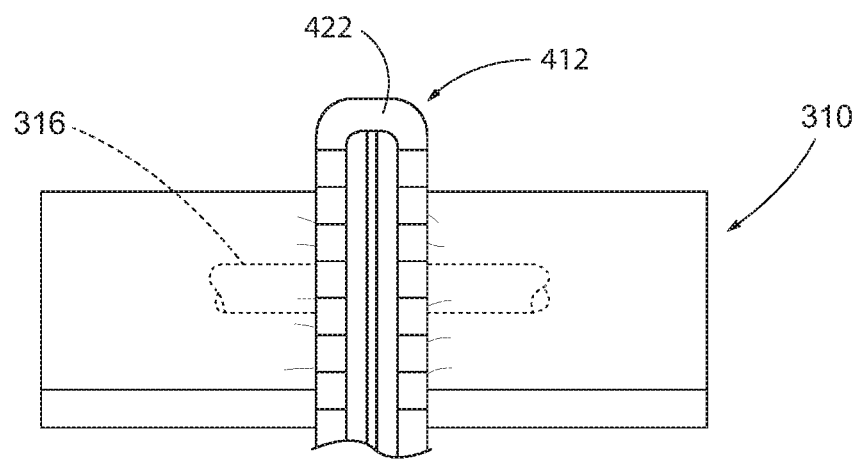
FIG. 39B depicts the schematic representation of the end effector of FIG. 27 severing the liver tissue of FIG. 39A.

As shown in FIG. 39B, the operator positions end effector (412) such that tissue (310), including vessel or duct (316), is located between lower and upper jaws (420, 422). The operator then compresses tissue (310) between upper and lower crush surfaces (414, 416) of upper and lower jaws (420, 422), respectively, to deliver the predetermined crush pressure to tissue (310). By way of example only, jaws (420, 422) may be actuated in this manner by pivoting trigger (24) toward pistol grip (22). It should be understood that jaws (420, 422) need not necessarily be actuated to a fully closed configuration. In some instances, the operator may rely on tactile feedback through trigger (24) and pistol grip (22) to determine whether the operator has achieved a desired gap between jaws (420, 422) to suitably crush tissue (310) without undesirably damaging vessel or duct (316). In addition or in the alternative, the operator may rely on visual feedback.

Figure 39C:
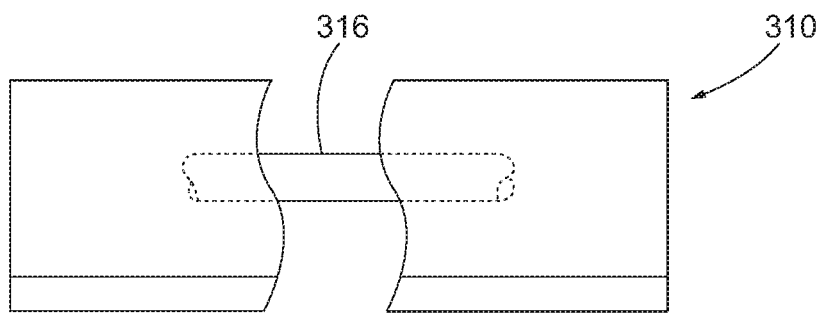
FIG. 39C depicts the schematic representation of the vessel of FIG. 39B exposed from the severed liver tissue of FIG. 39A.

In any case, the crush pressure applied by jaws (420, 422) effectively severs tissue (310), and the operator then removes end effector (412) from tissue (310) to view whether or not any vessels or ducts are present. As shown in FIG. 39C, vessel or duct (316) remains intact and is left exposed, extending between severed portions of tissue (310).

Figure 39D:
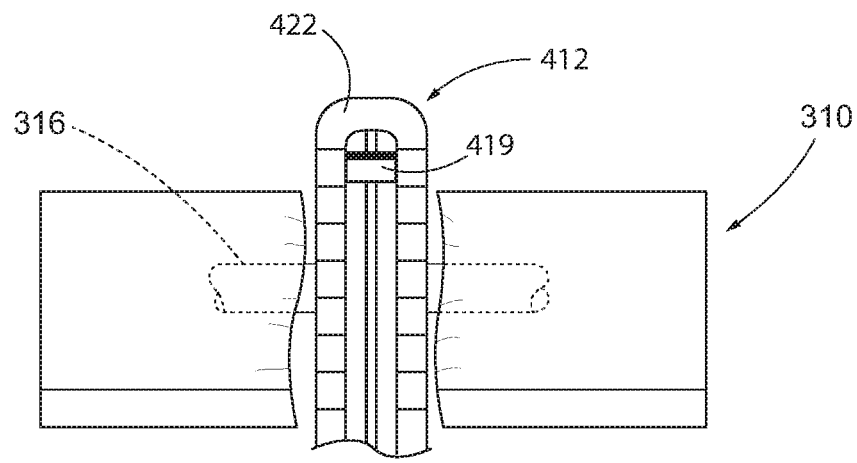
FIG. 39D depicts the schematic representation of the end effector of FIG. 27 stapling the exposed vessel of FIG. 39C.
Figure 39E:
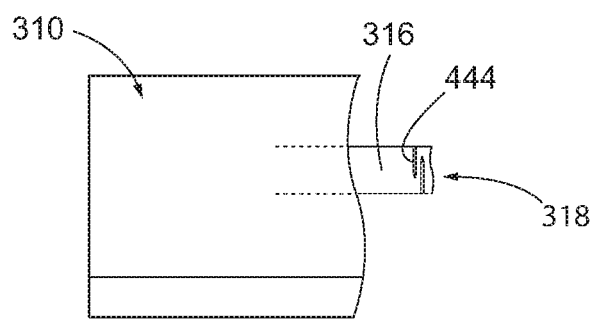
FIG. 39E depicts the schematic representation of the liver tissue of FIG. 39A having a portion of the liver tissue and the vessel resected therefrom.

In some instances, the operator may leave vessel or duct (316) intact. However, in the present example, the operator ligates vessel or duct (316) to complete the resection of a severed portion of tissue (310), as shown in FIG. 39D. Ligation includes placement of at least some of overlapping staples (444) within vessel or duct (316) as discussed above in greater detail. It should therefore be understood that the same end effector (412) may be used to crush (and thereby sever) tissue (310) of the liver and also ligate a vessel or duct (316) in the tissue (310). In the present example, the vessel or duct (316) is stapled and severed substantially simultaneously by end effector (412), resulting in the configuration shown in FIG. 39E. As shown, the severed end (318) of the vessel or duct (316) is sealed by staples (444). Thereby, the operator completes resection of a right portion of tissue (310) and the corresponding portion of the vessel or duct (316).

As described above, the operator removes end effector (412) for viewing vessel (316) as shown in FIG. 39C. Alternatively, the operator may apply the predetermined crush pressure (or as determined based on tactile and/or visual feedback as noted above), as shown in FIG. 39B, and immediately thereafter sever and ligate any tissue remaining therein, such as vessel or duct (316). As such, it is not necessary to view such tissue, but the operator may find such viewing desirable in one or more liver resection procedures. It will be appreciated that the above described resection is merely illustrative and not limited to liver tissue. Alternatively, tissue resection with end effector (412) may be performed on other tissues within the patient as desired by the user.

III. Exemplary Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

EXAMPLE 1

A method of operating on tissue, comprising: (a) positioning tissue between a first jaw and a second jaw of an end effector, wherein the first jaw comprises a plurality of staples, wherein the second jaw comprises a plurality of staple forming features, wherein the end effector is in an open configuration during the act of positioning tissue between the first jaw and the second jaw; (b) compressing the tissue between the first jaw and the second jaw, wherein the act of compressing the tissue provides dissection of at least some of the compressed tissue, wherein the dissected tissue reveals a vessel or duct; and (c) actuating the end effector to drive one or more of the staples through the revealed vessel or duct, thereby ligating the revealed vessel or duct.

EXAMPLE 2

The method of Example 1, further comprising severing the ligated vessel or duct.

EXAMPLE 3

The method of Example 2, wherein the act of severing the ligated vessel comprises actuating a cutting member through the end effector.

EXAMPLE 4

The method of Example 3, wherein the act of actuating the actuating the end effector to drive one or more of the staples comprises driving a cam distally with the cutting member, wherein the cam drives the staples toward the second jaw.

EXAMPLE 5

The method of any one or more of Examples 3 through 4, wherein the cutting member comprises an indicator visually indicating a longitudinal position of the cutting member, wherein the act of severing the ligated vessel further comprises observing the indicator to determine the longitudinal position of the cutting member.

EXAMPLE 6

The method of any one or more of Examples 1 through 5, further comprising transitioning the end effector to an open configuration after performing the act of compressing the tissue and before performing the act of actuating the end effector to drive one or more of the staples.

EXAMPLE 7

The method of any one or more of Examples 1 through 6, wherein the tissue comprises liver tissue.

EXAMPLE 8

The method of any one or more of Examples 1 through 7, wherein at least a portion of the end effector extends along a curved path.

EXAMPLE 9

The method of any one or more of Examples 1 through 8, wherein the first jaw comprises two longitudinally extending rows of staples.

EXAMPLE 10

The method of Example 9, wherein at least a portion of each row of staples extends along a curved path.

EXAMPLE 11

The method of Example 10, wherein a first portion of each row of staples extends along a curved path, wherein a second portion of each row of staples extends along a straight path.

EXAMPLE 12

The method of any one or more of Examples 1 through 11, wherein the end effector further comprises a plurality of staple drivers, wherein each staple driver of the plurality of staple drivers is operable to simultaneously drive at least two respective staples of the plurality of staples simultaneously toward the second jaw, wherein the act of actuating the end effector to drive one or more of the staples comprises driving the plurality of staple drivers toward the second jaw, thereby driving the plurality of staples toward the second jaw.

EXAMPLE 13

The method of Example 12, wherein each staple driver spans laterally across a plane that extends longitudinally along the lateral center of the first jaw.

EXAMPLE 14

The method of any one or more of Examples 12 through 13, wherein the plurality of staple drivers further comprises a distal-most staple driver, wherein the distal-most staple driver is operable to drive three staples of the plurality of staples simultaneously toward the second jaw.

EXAMPLE 15

The method of Example 14, wherein a distal-most staple of the three staples associated with the distal-most staple driver is oriented obliquely relative to the other two staples of the three staples associated with the distal-most staple driver.

EXAMPLE 16

The method of any one or more of Examples 1 through 15, wherein the first jaw further comprises a staple cartridge containing the plurality of staples, the method further comprising removing the staple cartridge from the second jaw after performing the act of actuating the end effector to drive one or more of the staples.

EXAMPLE 17

The method of any one or more of Examples 1 through 16, wherein the end effector comprises a plurality of staple drivers and a wedge sled, wherein each of the staple drivers comprises an underside having a cam surface, wherein the staple drivers are operable to drive the staples toward the second jaw, wherein the wedge sled comprises a cam surface operable to bear against the cam surface on the underside of each staple driver and thereby drive the staple drivers toward the second jaw in response to distal movement of the wedge sled, wherein the act of actuating the end effector to drive one or more of the staples comprises driving the wedge sled distally, thereby driving the staple drivers toward the second jaw, thereby driving the staples toward the second jaw.

EXAMPLE 18

The method of Example 17, wherein the plurality of staple drivers comprises a distal-most staple driver, wherein the act of driving the wedge sled distally comprises driving the wedge sled to a distal-most position, wherein a portion of the underside of the distal-most staple driver extends distally past at least a portion of the cam surface of the wedge sled.

EXAMPLE 19

A method of operating on tissue, comprising: (a) positioning liver tissue between a first jaw and a second jaw of an end effector, wherein the first jaw comprises a plurality of staples, wherein the second jaw comprises a plurality of staple forming features, wherein the end effector is in an open configuration during the act of positioning liver tissue between the first jaw and the second jaw; (b) compressing the liver tissue between the first jaw and the second jaw, wherein the act of compressing the liver tissue provides dissection of at least some of the compressed liver tissue; and (c) actuating the end effector to drive one or more of the staples through a vessel or duct associated with the liver, thereby ligating the vessel or duct.

EXAMPLE 20

A method of operating on tissue, comprising: (a) positioning liver tissue between a first jaw and a second jaw of an end effector, wherein the first jaw comprises a plurality of staples, wherein the second jaw comprises a plurality of staple forming features, wherein the end effector is in an open configuration during the act of positioning liver tissue between the first jaw and the second jaw; (b) compressing the liver tissue between the first jaw and the second jaw, wherein the act of compressing the liver tissue provides dissection of at least some of the compressed liver tissue; and (c) actuating the end effector, wherein the act of actuating the end effector comprises: (i) driving one or more of the staples through a vessel or duct associated with the liver, thereby ligating the vessel or duct, and (ii) driving a cutting member through the vessel or duct to thereby sever the vessel or duct, wherein the vessel or duct is severed adjacent to the staples in the vessel or duct.

EXAMPLE 21

A surgical instrument for treating a tissue of a patient, comprising: (a) a shaft assembly; (b) an end effector extending from the shaft assembly along a jaw centerline, the end effector comprising: (i) a first jaw having an anvil configured to form a plurality of staples pressed against the anvil, and (ii) a second jaw, wherein the first and second jaws are configured to transition between an open configuration and a closed configuration; and (c) a staple cartridge received within the second jaw, the staple cartridge comprising: (i) a deck facing the anvil, wherein the deck defines a plurality of staple openings, the plurality of staple openings comprising a first row of staple openings and a second row of staple openings, the first and second rows of staple openings defining a first row centerline therebetween, (ii) a plurality of staples positioned respectively within the plurality of staple openings, (iii) a first driver assembly positioned on the first row centerline, wherein the first driver is asymmetric about the first row centerline and is configured to drive a first portion of the plurality of staples, and (iv) a second driver assembly positioned on the first row centerline, wherein the second driver assembly is asymmetric about the first row centerline and is configured to drive a second portion of the plurality of staples; wherein the first and second driver assemblies alternate such that the first and second driver assemblies overlap in a direction transverse to the first row centerline for forming offset and overlapping staple rows in tissue.

EXAMPLE 22

The surgical instrument of Example 21, wherein the staple cartridge further comprises a wedge sled configured to slide proximate to the deck from a proximal sled position to a distal sled position such that the wedge sled is configured to progressively engage the first and second driver assemblies sliding toward the distal sled position and progressively force the first and second portions of the plurality of staples toward the anvil for formation in the tissue.

EXAMPLE 23

The surgical instrument of Example 22, wherein the wedge sled has a first cam ramp, wherein the first cam ramp is configured to progressively engage the first and second driver assemblies.

EXAMPLE 24

The surgical instrument of Example 23, wherein the plurality of staple openings include a third row of staple openings and a fourth row of staple openings, the third and fourth row of staple openings defining a second row centerline therebetween, wherein the first and second row centerlines are offset from each other and extending along opposing sides of the jaw centerline, wherein the staple cartridge further comprises: (i) a third driver assembly positioned on the second row centerline, wherein the third driver assembly is asymmetric about the second row centerline and is configured to drive a third portion of the plurality of staples, and (ii) a fourth driver assembly positioned on the row centerline and being asymmetric about the second row centerline and configured to drive a fourth portion of the plurality of staples; wherein the wedge sled has a second cam ramp, wherein the second cam ramp is configured to progressively engage the third and fourth driver assemblies.

EXAMPLE 25

The surgical instrument of any one or more of Examples 22 through 24, wherein the wedge sled has a distal nose, wherein the second jaw has a blocker wall distally positioned therein along the centerline, wherein the blocker wall is configured to receive the wedge sled thereagainst and inhibit movement of the wedge sled distally beyond the distal sled position, wherein the blocker wall defines a clearance hole configured to receive the distal nose of the wedge sled in the distal sled position.

EXAMPLE 26

The surgical instrument of Example 25, wherein the wedge sled has a first cam ramp configured to engage the first and second driver assemblies, wherein the second driver assembly is a distal-most driver assembly, wherein a majority of the first cam ramp in the distal sled position is below the distal-most driver assembly.

EXAMPLE 27

The surgical instrument of any one or more of Examples 21 through 26, wherein the first row centerline is offset from the jaw centerline.

EXAMPLE 28

The surgical instrument of Example 27, wherein the first row centerline is parallel with the jaw centerline.

EXAMPLE 29

The surgical instrument of any one or more of Examples 21 through 28, wherein the first driver assembly has a first distal driver, a first intermediate driver, and a first proximal driver; wherein the first distal driver, the first intermediate driver, and the first proximal drivers are operatively connected such that the first distal driver and the first proximal driver are longitudinally aligned and the first intermediate driver is transversely offset from each of the first distal driver and the first proximal driver; wherein the first distal driver, the first intermediate driver, and the first proximal driver respectively receive the first portion of the plurality of staples.

EXAMPLE 30

The surgical instrument of Example 29, wherein the second driver assembly has a second distal driver, a second intermediate driver, and a second proximal driver; wherein the second distal driver, the second intermediate driver, and the second proximal drivers are operatively connected such that the second distal driver and the second proximal driver are longitudinally aligned and the second intermediate driver is transversely offset from each of the second distal driver and the second proximal driver; wherein the second distal driver, the second intermediate driver, and the second proximal driver respectively receive the second portion of the plurality of staples.

EXAMPLE 31

The surgical instrument of Example 30, wherein the first and second driver assemblies alternate such that first and second intermediate drivers of the respective first and second driver assemblies are positioned on opposing sides of the first row centerline.

EXAMPLE 32

The surgical instrument of Example 31, wherein the first distal driver of the first driver assembly overlaps in the direction transverse to the first row centerline with the second proximal driver of the second driver assembly.

EXAMPLE 33

The surgical instrument of any one or more of Examples 29 through 32, wherein the first distal driver, the first intermediate driver, and the first proximal driver are connected by a first driver cam extending therebetween.

EXAMPLE 34

The surgical instrument of Example 33, wherein the staple cartridge further comprises a wedge sled configured to slide proximate to the deck from a proximal sled position to a distal sled position such that the wedge sled is configured to engage the first driver cam thereby forcing the first distal driver, the first intermediate driver, and the first proximal driver toward the anvil for forming the first portion of the plurality of staples against the anvil.

EXAMPLE 35

The surgical instrument of any one or more of Examples 21 through 34, wherein the first jaw has a first elongated channel extending therethrough and a first plurality of indicia, wherein the second jaw has a second elongated channel extending therethrough and a second plurality of indicia, the end effector further comprising a knife member received within the first and second channels, wherein the knife member is configured to slide distally along the first and second channels and engage a wedge sled for forming staples, wherein the knife member comprises an first indicator in the first channel and a second indicator in the first channel, and wherein the first and second indicators in conjunction with the first and second plurality of indicia are respectively configured to indicate a staple usage to an operator.

EXAMPLE 36

A surgical instrument for treating a tissue of a patient, comprising: (a) a shaft assembly; (b) an end effector extending from the shaft assembly along a jaw centerline, the end effector comprising: (i) a first jaw having an anvil configured to form a plurality of staples pressed against the anvil, and (ii) a second jaw, wherein the first and second jaws are configured to transition between an open configuration and a closed configuration; and (c) a staple cartridge received within the second jaw, the staple cartridge comprising: (i) a deck facing the anvil, (ii) a plurality of staple openings formed through the deck, wherein at least one of the staple openings obliquely crosses the centerline, and (iii) a plurality of staples positioned respectively within the plurality of staple openings.

EXAMPLE 37

The surgical instrument of Example 36, wherein the plurality of staple openings comprises a first row of staple openings and a second row of staple openings, wherein the first and second rows of staple openings are on respective sides of the centerline.

EXAMPLE 38

The surgical instrument of Example 37, wherein the at least one staple opening obliquely crossing the centerline extends from the first row of staple openings to the second row of staple openings.

EXAMPLE 39

The surgical instrument of Example 38, wherein the at least one staple opening that obliquely crosses the centerline is a distal-most staple opening in the deck.

EXAMPLE 40

The surgical instrument of Example 39, wherein the end effector extends to a distal tip, wherein the distal-most staple opening in the deck is adjacent to the distal tip.

EXAMPLE 41

The surgical instrument of any one or more of Examples 38 through 40, wherein the end effector, the staple cartridge, and the centerline having a straight portion extending to an arcuate portion, and the at least one staple opening that obliquely crosses the centerline is formed in the arcuate portion of the staple cartridge.

EXAMPLE 42

The surgical instrument of any one or more of Examples 36 through 41, wherein the end effector, the staple cartridge, and the centerline have the arcuate portion and a straight portion, wherein straight portion extends to the arcuate portion.

EXAMPLE 43

The surgical instrument of Example 42, wherein the plurality of staple openings comprises a first row of staple openings and a second row of staple openings, wherein the first and second rows of staple openings are located on respective sides of the centerline and are formed on the deck in the straight portion.

EXAMPLE 44

The surgical instrument of any one or more of Examples 37 through 43, wherein the first row of staple openings comprises an outer row of staple openings, wherein the second row of staple openings comprises an inner row of staple openings, wherein the outer row of staple openings is positioned radially outwardly from the centerline in the arcuate portion, wherein the inner row of staple openings is positioned radially inwardly from the centerline in the arcuate portion.

EXAMPLE 45

The surgical instrument of Example 44, wherein the outer row of staple openings defines a plurality of outer gaps between the adjacent staple openings of the plurality of staple openings, wherein the inner row of staple openings defines a plurality of inner gaps between adjacent staple openings of the plurality of staple openings, wherein the inner gaps and outer gaps have an equivalent length.

EXAMPLE 46

The surgical instrument of any one or more of Examples 36 through 45, wherein the staple cartridge further comprises a wedge sled configured to slide proximate to the deck from a proximal sled position to a distal sled position, wherein the distal sled position is below the at least one of the staple opening obliquely crossing the centerline.

EXAMPLE 47

The surgical instrument of Example 46, further comprising a wedge sled having a distal nose, wherein the second jaw has a blocker wall distally positioned therein along the centerline, wherein the blocker wall is configured to receive the wedge sled thereagainst and inhibit movement of the wedge sled distally beyond the distal sled position, wherein the blocker wall defines a clearance hole configured to receive the distal nose of the wedge sled in the distal sled position.

EXAMPLE 48

The surgical instrument of Example 12, wherein a majority of the wedge sled in the distal sled position is below the driver assembly.

EXAMPLE 49

The surgical instrument of any one or more of Examples 36 through 48, wherein the first jaw comprises a first crush surface extending generally parallel with the centerline, wherein the first crush surface is configured to receive tissue thereagainst, wherein the second jaw comprises a second crush surface extending generally parallel with the centerline, wherein the second crush surface is configured to receive tissue thereagainst, wherein the first and second crush surfaces are configured to compress tissue therebetween with a crush pressure configured to sever the tissue along the first and second crush surfaces.

EXAMPLE 50

The surgical instrument of Example 49, wherein the end effector, the staple cartridge, and the centerline have a straight portion extending to an arcuate portion, wherein the first and second crush surfaces extend along the straight and arcuate portions.

EXAMPLE 51

A surgical instrument for treating a tissue of a patient, comprising: (a) a shaft assembly; (b) an end effector extending from the shaft assembly along a jaw centerline, the end effector comprising: (i) a first jaw having an anvil configured to form a plurality of staples pressed against the anvil, and (ii) a second jaw, wherein the first and second jaws are configured to transition between an open configuration and a closed configuration; and (c) a staple cartridge received within the second jaw, the staple cartridge comprising: (i) a deck facing the anvil, wherein the deck defines a plurality of staple openings, wherein the plurality of staples are positioned respectively within the plurality of staple openings, (ii) a first terminal driver assembly positioned adjacent to a distal tip of the staple cartridge, wherein the first terminal driver assembly is configured to receive a first terminal portion of the plurality of staples, the first terminal driver assembly at least partially defining a storage space therebelow within the second jaw, and (iii) a wedge sled configured to slide proximate to the deck from a proximal sled position to a distal sled position and engage the first terminal driver assembly and force the terminal portion of the plurality of staples toward the anvil for formation in tissue, wherein at least a majority of the wedge sled is configured to fit within the storage space and not slide distally beyond the first terminal driver assembly when the wedge sled is in the distal sled position.

EXAMPLE 52

The surgical instrument of Example 51, wherein the wedge sled further comprises a first cam ramp, the first cam ramp being configured to engage the first terminal driver assembly and force the terminal portion of the plurality of staples toward the anvil for formation in the tissue, wherein a majority of the first cam ramp is configured to fit within the storage space when the wedge sled is in the distal sled position.

EXAMPLE 53

The surgical instrument of any one or more of Examples 51 through 52, wherein the wedge sled has a distal nose, wherein the second jaw has a blocker wall distally positioned therein along the centerline, wherein the blocker wall is configured to receive the wedge sled thereagainst and inhibit movement of the wedge sled distally beyond the distal sled position.

EXAMPLE 54

The surgical instrument of Example 53, wherein the blocker wall defines a clearance hole configured to receive the distal nose of the wedge sled in the distal sled position.

EXAMPLE 55

The surgical instrument of any one or more of Examples 51 through 54, wherein the wedge sled has a first cam ramp configured to engage the first terminal driver assembly, the first cam ramp further comprising: (A) a leading cam surface defining a steep angle slope, and (B) an intermediate cam surface defining a gradual angle slope, the gradual angle slope being angled less than the steep angle slope relative to the deck, wherein the driver cam is configured to be engaged by the leading cam surface to lift the driver assembly upward toward the first jaw over a relatively short distance for decreasing an elongation of the wedge sled, and wherein driver cam is further configured to be engaged by the intermediate cam surface to further lift the drive assembly upward toward the first jaw over a relatively long distance for providing enough force to compress the first and second staples against the anvil for use in tissue.

EXAMPLE 56

The surgical instrument of any one or more of Examples 51 through 55, wherein the first terminal driver assembly has a first terminal distal driver, a first terminal intermediate driver, and a first terminal proximal driver; wherein the first terminal distal driver, the first terminal intermediate driver, and the first terminal proximal drivers are operatively connected such that the first terminal distal driver is distally cantilevered relative to the first terminal intermediate driver and the first terminal intermediate driver for a maximum elongation of the storage space therebelow, wherein the first terminal distal driver is adjacent to the distal tip of the staple cartridge.

EXAMPLE 57

The surgical instrument of Example 56, wherein the first terminal distal driver, the first terminal intermediate driver, and the first terminal proximal driver are operatively connected such that the first terminal distal driver and the first terminal proximal driver are longitudinally aligned and the first terminal intermediate driver is transversely offset from each of the first terminal distal driver and the first terminal proximal driver, wherein the first terminal distal driver, the first terminal intermediate driver, and the first terminal proximal driver respectively receive the first terminal portion of the plurality of staples.

EXAMPLE 58

The surgical instrument of any one or more of Examples 51 through 57, wherein the staple cartridge further comprises a second terminal driver assembly positioned adjacent to the distal tip and configured to receive a second terminal portion of the plurality of staples, the second terminal driver assembly further defining the storage space therebelow within second jaw.

EXAMPLE 59

The surgical instrument of Example 58, wherein the second terminal driver assembly comprises a second terminal distal driver, a second terminal intermediate driver, and a second terminal proximal driver; wherein the second terminal distal driver, the second terminal intermediate driver, and the second terminal proximal drivers are operatively connected such that the second terminal distal driver is distally cantilevered relative to the second terminal intermediate driver and the second terminal intermediate driver for a maximum elongation of the storage space therebelow, wherein the second terminal distal driver is adjacent to the distal tip.

EXAMPLE 60

The surgical instrument of Example 59,wherein the first and second terminal distal driver assemblies are positioned on opposing sides of the centerline.

EXAMPLE 61

The surgical instrument of Example 60, wherein the first and second terminal distal driver assemblies are positioned such that the second terminal distal driver assembly mirrors the first terminal distal driver assembly about the centerline.

EXAMPLE 62

The surgical instrument of any one or more of Examples 60 through 61, wherein the wedge sled has a first cam ramp and a second cam ramp, wherein the first cam ramp is configured to engage the first terminal distal driver assembly, wherein the second cam ramp is configured to engage the second terminal distal driver assembly.

EXAMPLE 63

The surgical instrument of Example 62, wherein the first cam ramp has a first distal nose, wherein the second cam ramp has a second distal nose, wherein the second jaw has a second jaw having a blocker wall distally positioned therein along the centerline, wherein the blocker wall is configured to receive the wedge sled thereagainst and inhibit movement of the wedge sled distally beyond the distal sled position, wherein the blocker wall defines at least one clearance hole configured to receive the first and second distal noses of the wedge sled in the distal sled position.

EXAMPLE 64

The surgical instrument of any one or more of Examples 51 through 63, wherein the first jaw has a first elongated channel extending therethrough and a first plurality of indicia, wherein the second jaw has a second elongated channel extending therethrough and a second plurality of indicia, the instrument further comprising a knife member received within the first and second channels, wherien the knife member is configured to slide distally the first and second channels and engage the wedge sled for forming staples, wherein the knife member comprises a first indicator in the first channel and a second indicator in the second channel, and wherein the first and second indicators in conjunction with the first and second plurality of indicia are respectively configured to indicate a staple usage to an operator.

EXAMPLE 65

A surgical instrument for treating a tissue of a patient, comprising: (a) a shaft assembly; (b) an end effector extending from the shaft assembly along a jaw centerline, the end effector comprising: (i) a first jaw having an anvil configured to form a plurality of staples pressed against the anvil, and (ii) a second jaw, wherein the first and second jaws are configured to transition between an open configuration and a closed configuration; and (c) a staple cartridge received within the second jaw, wherein the staple cartridge and the end effector have an arcuate portion, the staple cartridge comprising: (i) a deck facing the anvil, wherein the deck defines a plurality of staple openings, wherein the plurality of staple openings comprises an outer row of staple openings positioned radially outward from the centerline in the arcuate portion and an inner row of staple openings positioned radially inward from the centerline in the arcuate portion, and (ii) a plurality of staples positioned respectively within the plurality of staple openings, wherein the plurality of staples include an outer set of staples and an inner set of staples for respective receipt within the outer and inner rows of staple openings, wherein at least one staple of the outer set of staples has an elongated crown relative to the inner set of staples such that the outer set of staples are configured to overlap with the inner set of staples in a direction transverse to the centerline.

EXAMPLE 66

The surgical instrument of Example 65, wherein the end effector, the staple cartridge, and the centerline have a straight portion, wherein the straight portion extends to the arcuate portion.

EXAMPLE 67

The surgical instrument of Example 66, wherein the plurality of staple openings comprises a first row of staple openings and a second row of staple openings, wherein the first and second rows of staple openings are positioned on respective sides of centerline and are formed on the deck in the straight portion.

EXAMPLE 68

The surgical instrument of any one or more of Examples 65 through 67, wherein the outer row of staple openings defines a plurality of outer gaps between the plurality of staple openings, wherein the inner row of staple openings defines a plurality of inner gaps between the plurality of staple openings, wherein the inner gaps and outer gaps have an equivalent elongation.

EXAMPLE 69

The surgical instrument of any one or more of Examples 65 through 68, wherein the plurality of staple openings further include at least one staple opening extending between the outer and inner rows of staple openings, wherein the at least one staple opening extending between the outer and inner rows of staple opening straddles the centerline.

EXAMPLE 70

The surgical instrument of Example 69, wherein the at least one staple opening that straddles the centerline is a distal-most staple opening in the deck.

EXAMPLE 71

The surgical instrument of any one or more of Examples 65 through 70, wherein the first jaw comprises a first crush surface extending generally parallel with the centerline, wherein the first crush surface is configured to receive tissue thereagainst, wherein the second jaw comprises a second crush surface extending generally parallel with the centerline, wherein the second crush surface is configured to receive the tissue thereagainst, wherein the first and second crush surfaces are configured to compress tissue therebetween with a crush pressure configured to sever the tissue along the first and second crush surfaces.

EXAMPLE 72

The surgical instrument of Example 71, wherein the end effector, the staple cartridge, and the centerline have a straight portion, wherein the straight portion extends to the arcuate portion, and wherein the first and second crush surfaces extend along the straight and arcuate portions.

EXAMPLE 73

The surgical instrument of Example 72, wherein the second crush surface is formed on the deck of the staple cartridge.

EXAMPLE 74

The surgical instrument of any one or more of Examples 65 through 73, wherein the arcuate portion extends to a distal tip of the end effector, and wherein at least a portion of the end effector tapers inwardly toward the distal tip.

EXAMPLE 75

The surgical instrument of any one or more of Examples 65 through 74, wherein staple cartridge further comprises a wedge sled configured to slide proximate to the deck from a proximal sled position to a distal sled position, and wherein the wherein the distal sled position is in the arcuate portion of the end effector.

EXAMPLE 76

The surgical instrument of Example 75, wherein the staple cartridge further comprises a slot positioned below the deck, wherein the slot extends along the centerline at least partially through the arcuate portion.

EXAMPLE 77

The surgical instrument of Example 76, wherein the staple cartridge further comprises a driver assembly having a first driver and a second driver, the first driver receiving a first staple of the plurality of staples, and the second driver receiving a second staple of the plurality of staples, wherein the driver assembly is configured to be engaged by the wedge sled sliding toward the distal sled position and forced toward the first jaw, thereby forcing the first and second staples toward the anvil for formation in tissue.

EXAMPLE 78

The surgical instrument of Example 77, wherein the wedge sled comprises a cam ramp, the cam ramp being positioned on the centerline within the slot and configured to engage the driver assembly and force the driver assembly toward the first jaw.

EXAMPLE 79

The surgical instrument of Example 78, further comprising a translating member engaged with wedge sled and configured to be actuated to drive the wedge sled from the proximal sled position toward the distal sled position, wherein translating member and wedge sled are configured to follow the centerline along the slot through the arcuate portion.

EXAMPLE 80

A surgical instrument for treating a tissue of a patient, comprising: (a) a shaft assembly; (b) an end effector extending from the shaft assembly along a jaw centerline, the end effector comprising: (i) a first jaw having an anvil configured to form a plurality of staples pressed against the anvil, and (ii) a second jaw, wherein the first and second jaws are configured to transition between an open configuration and a closed configuration, wherein the first jaw and the second jaw define a straight portion of the end effector and an arcuate portion of the end effector, the arcuate portion extending distally from the straight portion such that the arcuate portion of the end effector is configured to provide access to tissue within a patient for treatment.

EXAMPLE 81

The surgical instrument of Example 80, wherein the straight portion defines a proximal transverse width generally perpendicular to the centerline, wherein the arcuate portion defines a distal transverse width generally perpendicular centerline, wherein the end effector tapers inwardly from the straight portion toward the arcuate portion such that the distal transverse width is narrower than the proximal transverse width.

EXAMPLE 82

The surgical instrument of Example 81, wherein the distal transverse width of the arcuate portion tapers inwardly toward the centerline distally along the centerline from the straight portion.

EXAMPLE 83

The surgical instrument of Example 82, wherein the end effector comprises a distal tip, wherein the arcuate portion tapers inwardly toward the centerline from the straight portion to the distal tip.

EXAMPLE 84

The surgical instrument of any one or more of Examples 80 through 83, further comprising a staple cartridge received within the second jaw, the staple cartridge comprising: (i) a deck facing the anvil, (ii) a plurality of staple openings formed through the deck, and (iii) a plurality of staple positioned respectively within the plurality of staple openings.

EXAMPLE 85

The surgical instrument of Example 84, wherein the plurality of staple openings comprises a first row of staple openings and a second row of staple openings, wherein the first and second rows of staple openings are positioned on respective sides of centerline and are formed on the deck in each of the straight and the arcuate portions.

EXAMPLE 86

The surgical instrument of Example 85, wherein the first row of staple openings comprises an outer row of staple openings, wherein the second row of staple openings comprises an inner row of staple openings, wherein the outer row of staple openings is positioned radially outwardly from the centerline in the arcuate portion, wherein the inner row of staple openings is positioned radially inwardly from the centerline in the arcuate portion.

EXAMPLE 87

The surgical instrument of Example 86, wherein the outer row of staple openings defines a plurality of outer gaps between the plurality of staple openings, wherein the inner row of staple openings defines a plurality of inner gaps between the plurality of staple openings, wherein the inner gaps and outer gaps have an equivalent elongation.

EXAMPLE 88

The surgical instrument of any one or more of Examples 85 through 87, wherein the plurality of staple openings further comprises at least one staple opening extending between the first and second rows of staple openings, wherein the at least one staple opening straddles the centerline.

EXAMPLE 89

The surgical instrument of Example 88, wherein the at least one staple opening that straddles the centerline is a distal-most staple opening in the deck.

EXAMPLE 90

The surgical instrument of any one or more of Examples 84 through 89, wherein the staple cartridge further comprises a wedge sled configured to slide proximate to the deck from a proximal sled position to a distal sled position, wherein the proximal sled position is in the straight portion of the end effector, wherein the distal sled position is in the arcuate portion of the end effector.

EXAMPLE 91

The surgical instrument of Example 90, wherein the staple cartridge further comprises a slot positioned below the deck, wherein the slot extends along the centerline at least partially through each of the straight and arcuate portions.

EXAMPLE 92

The surgical instrument of Example 91, wherein the staple cartridge further comprises a driver assembly having a first driver and a second driver, the first driver receiving a first staple of the plurality of staples, the second driver receiving a second staple of the plurality of staples, wherein the driver assembly is configured to be engaged by the wedge sled sliding toward the distal sled position and forced toward the first jaw, thereby forcing the first and second staples toward the anvil for formation in the tissue.

EXAMPLE 93

The surgical instrument of Example 92, wherein the wedge sled comprises a cam ramp, the cam ramp being positioned on the centerline within the slot and configured to engage the driver assembly and force the driver assembly toward the first jaw.

EXAMPLE 94

The surgical instrument of any one or more of Examples 80 through 93, wherein the first jaw comprises a first crush surface extending generally parallel with the centerline, wherein the first crush surface is configured to receive tissue thereagainst, wherein the second jaw comprises a second crush surface extending generally parallel with the centerline, wherein the second crush surface is configured to receive tissue thereagainst, wherein the first and second crush surfaces are configured to compress tissue therebetween with a crush pressure configured to sever the tissue along the first and second crush surfaces.

EXAMPLE 95

A surgical instrument for treating a tissue of a patient, comprising: (a) a shaft assembly; and (b) an end effector extending from the shaft assembly along a jaw centerline, the end effector comprising: (i) a first jaw, wherein the first jaw comprises: (A) an anvil configured to form a plurality of staples pressed thereagainst, (B) an upper elongated channel extending therethrough, and (C) a first plurality of indicia positioned proximate to the first elongated channel, (ii) a second jaw, wherein the first and second jaws are configured to transition between an open configuration and a closed configuration, wherein the second jaw comprises: (A) a second elongated channel extending therethrough, and (B) a second plurality of indicia positioned proximate to the second elongated channel, and (iii) a translating member received within the first and second channels, wherein the translating member is configured to slide distally along the first and second channels and engage the wedge sled for forming staples, wherein the translating member comprises a first indicator and a second indicator, wherein the first and second indicators in conjunction with the first and lower plurality of indicia are respectively configured to indicate one or both of staple usage or a cut position to an operator.

EXAMPLE 96

The surgical instrument of Example 95, wherein the indicated staple usage represents an amount of the plurality of staples remaining in the staple cartridge.

EXAMPLE 97

The surgical instrument of any one or more of Examples 95 through 96, wherein the plurality of first indicia is in the form of a numerical countdown extending distally along the first jaw, and wherein the plurality of second indicia is in the form of another numerical countdown extending distally along the second jaw.

EXAMPLE 98

The surgical instrument of any one or more of Examples 95 through 97, further comprising a staple cartridge received within the second jaw.

EXAMPLE 99

The surgical instrument of any one or more of Examples 95 through 98, wherein the translating member is in the form of a knife member configured to cut the tissue.

EXAMPLE 100

The surgical instrument of any one or more of Examples 95 through 99, wherein the translating member comprises a first flange and a second flange, wherein the first flange extends through the first elongated channel and is engaged with the first jaw, wherein the second flange extends through the second elongated channel and engages the second jaw.

EXAMPLE 101

The surgical instrument of Example 100, wherein the first indicator is on the first flange, wherein the second indicator is on the second flange.

EXAMPLE 102

The surgical instrument of any one or more of Examples 95 through 101, wherein the first and second elongated channels extend parallel to the centerline.

EXAMPLE 103

The surgical instrument of Example 102, wherein the first elongated channel extends along the centerline.

EXAMPLE 104

The surgical instrument of Example 103, wherein the second channel extends along the centerline.

EXAMPLE 105

A surgical instrument for treating a tissue of a patient, comprising: (a) a shaft assembly; (b) an end effector extending from the shaft assembly along a jaw centerline, the end effector comprising: (i) a first jaw having an anvil configured to form a plurality of staples pressed against the anvil, and (ii) a second jaw, wherein the first and second jaws are configured to transition between an open configuration and a closed configuration; and (c) a staple cartridge received within the second jaw, the staple cartridge comprising: (i) a deck facing the anvil, wherein the deck defines a plurality of staple openings, (ii) a plurality of staples positioned respectively within the plurality of staple openings, (iii) a wedge sled configured to slide proximate to the deck from a proximal sled position to a distal sled position, and (iv) a driver assembly having a first driver and a second driver, the first driver receiving a first staple of the plurality of staples, and the second driver receiving a second staple of the plurality of staples, wherein the driver assembly is configured to be engaged by the wedge sled sliding toward the distal sled position and thereby be forced toward the first jaw, thereby forcing the first and second staples toward the anvil for formation in the tissue, and wherein the driver assembly is positioned along the centerline.

EXAMPLE 106

The surgical instrument of Example 105, wherein the driver assembly comprises a driver cam configured to be engaged by the wedge sled, wherein the first and second drivers are connected by the driver cam extending therebetween, wherein the driver cam is positioned along the centerline.

EXAMPLE 107

The surgical instrument of Example 106, wherein the driver cam has a first side and an opposing second side, wherein the first driver is connected to the first side of the driver cam, wherein the second driver is connected to the opposing second side of the driver cam, wherein the driver cam straddles the centerline such that the first and second drivers are on opposing sides of the centerline.

EXAMPLE 108

The surgical instrument of any one or more of Examples 105 through 107, wherein the wedge sled is configured to slide proximate to the deck from the proximal sled position to the distal sled position along the centerline.

EXAMPLE 109

The surgical instrument of any one or more of Examples 105 through 108, wherein the wedge sled comprises a cam ramp, the cam ramp being positioned on the centerline and configured to engage the driver assembly and force the driver assembly toward the first jaw.

EXAMPLE 110

The surgical instrument of claim 105, wherein the end effector, the staple cartridge, and the centerline have a straight portion extending to an arcuate portion, wherein the staple cartridge comprises another driver assembly, wherein the driver assemblies are positioned respectively in the straight and arcuate portions along the centerline.

EXAMPLE 111

The surgical instrument of any one or more of Examples 105 through 110, wherein at least one of the first and second drivers is positioned along the centerline.

EXAMPLE 112

The surgical instrument of any one or more of Examples 105 through 111, wherein the driver assembly further comprises a third driver, wherein the third driver is positioned along the centerline.

EXAMPLE 113

The surgical instrument of any one or more of Examples 105 through 112, wherein the first jaw comprises a first crush surface extending generally parallel with the centerline, wherein the first crush surface is configured to receive tissue thereagainst, wherein the second jaw comprises a second crush surface extending generally parallel with the centerline, wherein the second crush surface is configured to receive the tissue thereagainst, wherein the first and second crush surfaces are configured to compress the tissue therebetween with a crush pressure configured to sever the tissue along the first and second crush surfaces.

EXAMPLE 114

The surgical instrument of Example 113, wherein the second crush surface is formed on the deck of the staple cartridge.

EXAMPLE 115

The surgical instrument of any one or more of Examples 105 through 114, wherein the end effector, the staple cartridge, and the centerline have a straight portion extending to an arcuate portion, wherein the first and second crush surfaces extend along the straight and arcuate portions.

EXAMPLE 116

The surgical instrument of Example 115, wherein the arcuate portion extends to a distal tip of the end effector, wherein the end effector tapers inwardly toward the distal tip.

EXAMPLE 117

The surgical instrument of any one or more of Examples 105 through 116, wherein the wedge sled has a distal nose, wherein the second jaw has a blocker wall distally positioned therein along the centerline, wherein the blocker wall is configured to receive the wedge sled thereagainst and inhibit movement of the wedge sled distally beyond the distal sled position, wherein the blocker wall defines a clearance hole configured to receive the distal nose of the wedge sled in the distal sled position.

EXAMPLE 118

The surgical instrument of Example 117, wherein a majority of the wedge sled is configured to be positioned below the driver assembly when the wedge sled is in the distal sled position.

IV. Miscellaneous

It should be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCI™ system by Intuitive Surgical, Inc., of Sunnyvale, Calif. Similarly, those of ordinary skill in the art will recognize that various teachings herein may be readily combined with various teachings of any of the following: U.S. Pat. No. 5,792,135, entitled "Articulated Surgical Instrument For Performing Minimally Invasive Surgery With Enhanced Dexterity and Sensitivity," issued Aug. 11, 1998, the disclosure of which is incorporated by reference herein; U.S. Pat. No. 5,817,084, entitled "Remote Center Positioning Device with Flexible Drive," issued Oct. 6, 1998, the disclosure of which is incorporated by reference herein; U.S. Pat. No. 5,878,193, entitled "Automated Endoscope System for Optimal Positioning," issued Mar. 2, 1999, the disclosure of which is incorporated by reference herein; U.S. Pat. No. 6,231,565, entitled "Robotic Arm DLUS for Performing Surgical Tasks," issued May 15, 2001, the disclosure of which is incorporated by reference herein; U.S. Pat. No. 6,783,524, entitled "Robotic Surgical Tool with Ultrasound Cauterizing and Cutting Instrument," issued Aug. 31, 2004, the disclosure of which is incorporated by reference herein; U.S. Pat. No. 6,364,888, entitled "Alignment of Master and Slave in a Minimally Invasive Surgical Apparatus," issued Apr. 2, 2002, the disclosure of which is incorporated by reference herein; U.S. Pat. No. 7,524,320, entitled "Mechanical Actuator Interface System for Robotic Surgical Tools," issued Apr. 28, 2009, the disclosure of which is incorporated by reference herein; U.S. Pat. No. 7,691,098, entitled "Platform Link Wrist Mechanism," issued Apr. 6, 2010, the disclosure of which is incorporated by reference herein; U.S. Pat. No. 7,806,891, entitled "Repositioning and Reorientation of Master/Slave Relationship in Minimally Invasive Telesurgery," issued Oct. 5, 2010, the disclosure of which is incorporated by reference herein; U.S. Pub. No. 2013/0012957, entitled "Automated End Effector Component Reloading System for Use with a Robotic System, published Jan. 10, 2013, issued as U.S. Pat. No. 8,844,789 on Sep. 30, 2014, the disclosure of which is incorporated by reference herein; U.S. Pub. No. 2012/0199630, entitled "Robotically-Controlled Surgical Instrument with Force-Feedback Capabilities," published Aug. 9, 2012, issued as U.S. Pat. No. 8,820,605 on Sep. 2, 2014, the disclosure of which is incorporated by reference herein; U.S. Pub. No. 2012/0132450, entitled "Shiftable Drive Interface for Robotically-Controlled Surgical Tool," published May 31, 2012, issued as U.S. Pat. No. 8,616,431 on Dec. 31, 2013, the disclosure of which is incorporated by reference herein; U.S. Pub. No. 2012/0199633, entitled "Surgical Stapling Instruments with Cam-Driven Staple Deployment Arrangements," published Aug. 9, 2012, issued as U.S. Pat. No. 8,573,461 on Nov. 5, 2013, the disclosure of which is incorporated by reference herein; U.S. Pub. No. 2012/0199631, entitled "Robotically-Controlled Motorized Surgical End Effector System with Rotary Actuated Closure Systems Having Variable Actuation Speeds," published Aug. 9, 2012, issued as U.S. Pat. No. 8,602,288 on Dec. 10, 2013, the disclosure of which is incorporated by reference herein; U.S. Pub. No. 2012/0199632, entitled "Robotically-Controlled Surgical Instrument with Selectively Articulatable End Effector," published Aug. 9, 2012, issued as U.S. Pat. No. 9,301,759 on Apr. 5, 2016, the disclosure of which is incorporated by reference herein; U.S. Pub. No. 2012/0203247, entitled "Robotically-Controlled Surgical End Effector System," published Aug. 9, 2012, issued as U.S. Pat. 8,783,541 on Jul. 22, 2014, the disclosure of which is incorporated by reference herein; U.S. Pub. No. 2012/0211546, entitled "Drive Interface for Operably Coupling a Manipulatable Surgical Tool to a Robot," published Aug. 23, 2012, issued as U.S. Pat. No. 8,479,969 on Jul. 9, 2013; U.S. Pub. No. 2012/0138660, entitled "Robotically-Controlled Cable-Based Surgical End Effectors," published Jun. 7, 2012, issued as U.S. Pat. No. 8,800,838 on Aug. 12, 2014, the disclosure of which is incorporated by reference herein; and/or U.S. Pub. No. 2012/0205421, entitled "Robotically-Controlled Surgical End Effector System with Rotary Actuated Closure Systems," published Aug. 16, 2012, issued as U.S. Pat. No. 8,573,465 on Nov. 5, 2013, the disclosure of which is incorporated by reference herein.

Versions of the devices described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a operator immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometries, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. A method of operating on tissue, comprising:
(a) positioning tissue between a first jaw and a second jaw of an end effector, wherein the first jaw comprises a plurality of staples and a first crush surface, wherein the plurality of staples includes a distal-most staple defining a crown length and the first crush surface includes a distal-most first crush surface portion such that the distal-most first crush surface portion distally terminates less than or equal to half of the crown length to the distal-most staple, wherein the second jaw comprises a plurality of staple forming features and a second crush surface facing toward the first crush surface, wherein the end effector is in an open configuration during the act of positioning tissue between the first jaw and the second jaw;
(b) compressing the tissue between the first crush surface of the first jaw and the second crush surface of the second jaw, wherein the act of compressing the tissue provides dissection of at least some of the compressed tissue, wherein the dissection of the at least some of the compressed tissue distally terminates at the distal-most first crush surface less than or equal to half of the crown length to the distal-most staple and the dissected tissue reveals a vessel or duct; and
(c) actuating the end effector to drive one or more of the staples through the revealed vessel or duct, thereby ligating the revealed vessel or duct.

2. The method of claim 1, further comprising severing the ligated vessel or duct.

3. The method of claim 2, wherein the act of severing the ligated vessel comprises actuating a cutting member through the end effector.

4. The method of claim 3, wherein the act of actuating the end effector to drive one or more of the staples comprises driving a cam distally with the cutting member, wherein the cam drives the staples toward the second jaw.

5. The method of claim 3, wherein the cutting member comprises an indicator visually indicating a longitudinal position of the cutting member, wherein the act of severing the ligated vessel further comprises observing the indicator to determine the longitudinal position of the cutting member.

6. The method of claim 5, wherein the indicator is configured to extend through the second jaw, and observing the indicator further includes observing the indicator on the second jaw to determine the longitudinal position of the cutting member.

7. The method of claim 1, further comprising transitioning the end effector to an open configuration after performing the act of compressing the tissue and before performing the act of actuating the end effector to drive one or more of the staples.

8. The method of claim 1, wherein the tissue comprises liver tissue.

9. The method of claim 1, wherein the plurality of staples of the first jaw comprises at least two longitudinally extending rows of staples.

10. The method of claim 1, wherein the end effector further comprises a plurality of staple drivers, wherein each staple driver of the plurality of staple drivers is operable to simultaneously drive at least two respective staples of the plurality of staples simultaneously toward the second jaw, wherein the act of actuating the end effector to drive one or more of the staples comprises driving the plurality of staple drivers toward the second jaw, thereby driving the plurality of staples toward the second jaw.

11. The method of claim 1, wherein the first jaw further comprises a staple cartridge containing the plurality of staples, the method further comprising removing the staple cartridge from the first jaw after performing the act of actuating the end effector to drive one or more of the staples.

12. The method of claim 1, wherein the end effector comprises a plurality of staple drivers and a wedge sled, wherein each of the staple drivers comprises an underside having a cam surface, wherein the staple drivers are operable to drive the staples toward the second jaw, wherein the wedge sled comprises a cam surface operable to bear against the cam surface on the underside of each staple driver and thereby drive the staple drivers toward the second jaw in response to distal movement of the wedge sled, wherein the act of actuating the end effector to drive one or more of the staples comprises driving the wedge sled distally, thereby driving the staple drivers toward the second jaw, thereby driving the staples toward the second jaw.

13. The method of claim 12, wherein the plurality of staple drivers comprises a distal-most staple driver, wherein the wedge sled defines a distal length component dimension, wherein the act of driving the wedge sled distally comprises driving the wedge sled to a distal-most position, and wherein at least a majority of the distal length component dimension is configured to be positioned directly under the distal-most staple driver when the wedge sled is in the distal-most position.

14. The method of claim 1, wherein the first jaw extends to a planar distal tip, wherein the planar distal tip has a distal-most surface that is proximate and perpendicular to the first crush surface.

15. A method of operating on tissue, comprising:
(a) positioning liver tissue between a first jaw and a second jaw of an end effector, wherein the first jaw comprises a plurality of staples and a first crush surface extending toward a planar distal tip, wherein the planar distal tip has a distal-most surface that is proximate and perpendicular to the first crush surface, wherein the second jaw comprises a plurality of staple forming features and a second crush surface facing toward the first crush surface, wherein the end effector is in an open configuration during the act of positioning liver tissue between the first jaw and the second jaw;
(b) compressing the liver tissue between the first crush surface of the first jaw and the second crush surface of the second jaw, wherein the act of compressing the liver tissue provides dissection of at least some of the compressed liver tissue; and
(c) actuating the end effector to drive one or more of the staples through a vessel or duct associated with the liver, thereby ligating the vessel or duct.

16. The method of claim 15, wherein the plurality of staples includes a distal-most staple defining a crown length and the first crush surface includes a distal-most first crush surface portion such that the distal-most first crush surface portion distally terminates less than or equal to half of the crown length to the distal-most staple, and wherein the dissection of the at least some of the compressed tissue distally terminates at the distal-most first crush surface less than or equal to half of the crown length to the distal-most staple.

17. The method of claim 15, further comprising:
(a) actuating a cutting member through the end effector, wherein the cutting member includes an indicator extending through the second jaw; and
(b) observing the indicator on the second jaw to determine a longitudinal position of the cutting member in the end effector.

18. A method of operating on tissue, comprising:
(a) positioning liver tissue between a first jaw and a second jaw of an end effector, wherein the first jaw comprises a plurality of staples and a first crush surface, wherein the first jaw extends to a planar distal tip, wherein the planar distal tip has a distal-most surface that is proximate and perpendicular to the crush surface, wherein the second jaw comprises a plurality of staple forming features and a second crush surface facing toward the first crush surface, wherein the end effector is in an open configuration during the act of positioning liver tissue between the first jaw and the second jaw;
(b) compressing the liver tissue between the first crush surface of the first jaw and the second crush surface of the second jaw, wherein the act of compressing the liver tissue provides dissection of at least some of the compressed liver tissue; and
(c) actuating the end effector, wherein the act of actuating the end effector comprises:
(i) driving one or more of the staples through a vessel or duct associated with the liver, thereby ligating the vessel or duct,
(ii) actuating a cutting member through the end effector, wherein the cutting member includes an indicator extending therefrom and through the second jaw,
(iii) driving the cutting member through the vessel or duct to thereby sever the vessel or duct while simultaneously moving the indicator along the second jaw, wherein the vessel or duct is severed adjacent to the staples in the vessel or duct, and
(iv) observing the indicator on the second jaw to determine a longitudinal position of the cutting member in the end effector.

19. The method of claim 18, wherein the plurality of staples includes a distal-most staple defining a crown length and the first crush surface includes a distal-most first crush surface portion such that the distal-most first crush surface portion distally terminates less than or equal to half of the crown length to the distal-most staple, and wherein the dissection of the at least some of the compressed tissue distally terminates at the distal-most first crush surface less than or equal to half of the crown length to the distal-most staple.

* * * * *